(12) United States Patent
Murthi et al.

(10) Patent No.: US 7,230,101 B1
(45) Date of Patent: Jun. 12, 2007

(54) SYNTHESIS OF METHOTREXATE-CONTAINING HETERODIMERIC MOLECULES

(75) Inventors: Krishna K. Murthi, Cambridge, MA (US); Chase C. Smith, Rutland, MA (US)

(73) Assignee: GPC Biotech, Inc., Waltham, MA (US)

( * ) Notice: Subject to any disclaimer, the term of this patent is extended or adjusted under 35 U.S.C. 154(b) by 132 days.

(21) Appl. No.: 10/651,340

(22) Filed: Aug. 28, 2003

Related U.S. Application Data

(60) Provisional application No. 60/407,131, filed on Aug. 28, 2002.

(51) Int. Cl.
C07D 475/00 (2006.01)
A01N 43/58 (2006.01)

(52) U.S. Cl. ...................... 544/260; 514/250
(58) Field of Classification Search ................. 544/260
See application file for complete search history.

(56) References Cited

U.S. PATENT DOCUMENTS

| | | | |
|---|---|---|---|
| 2003/0165873 A1* | 9/2003 | Come et al. ............... | 435/6 |
| 2004/0043388 A1* | 3/2004 | Come et al. ............... | 435/6 |
| 2004/0266854 A1* | 12/2004 | Becker et al. ............. | 514/406 |

FOREIGN PATENT DOCUMENTS

| | | |
|---|---|---|
| WO | WO-01/017614 | 3/2001 |
| WO | WO-02/020715 | 3/2002 |

OTHER PUBLICATIONS

Piper, J. R.; Montgomery, J. A.; Sirotnak, F. M.; Chello, P. L., Journal of Medicinal Chemistry, 25(2), 182-7 (English) 1982.*

(Continued)

*Primary Examiner*—Deepak Rao
*Assistant Examiner*—Cecilia Jaisle
(74) *Attorney, Agent, or Firm*—Fish & Neave IP Group Rones & Gray LLP

(57) ABSTRACT

The present invention relates to novel compositions of methotrexate-containing heterodimeric probe molecules, also known as chemical inducers of dimerization (CID), useful in three-hybrid assays. The invention further relates to synthesis of said compositions and their intermediates. Another aspect of the invention is a method for using the heterodimeric probe molecules described herein in drug screens to identify potential protein targets to a given ligand, optimize protein-ligand interactions, or identify potential ligands for a given protein target. In certain embodiments, the invention contemplates the synthesis of the following methotrexate-containing heterodimeric probe:

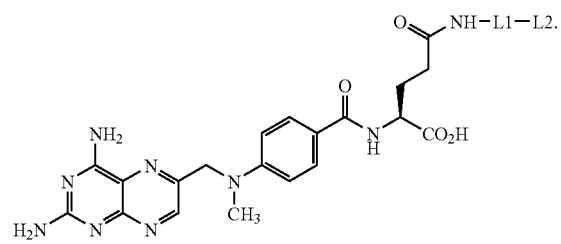

5 Claims, 1 Drawing Sheet

OTHER PUBLICATIONS

Knepper, T.; Przybylski, M.; Ahlers, M.; Ringsdorf, H. Chem. Biol. Pteridines, 1989 Proc. Int. Symp. Pteridines Folic Acid Deriv., 9th, Meeting Date 1989, 1280-3. Editor(s): Curtius, Hans-Christoph et al de Gruyter: Berlin, Fed. Rep. Ger. (English) 1990.*

Liu, Jianquan; Wooley, Karen L. Polymeric Materials Science and Engineering, 84, 967-968 (English) 2001.*

Antonjuk, David J.; Boadle, Deborah K.; Cheung, H. T. Andrew; Tran, Trung Q., Journal of the Chemical Society, Perkin Transactions,1: Organic and Bio-Organic Chemistry (1972-1999) (9), 1989-2003 (English) 1984.*

Kevin Davies, "Counting the Cost of Drug Discovery", BIO-IT World [online] Jul. 11, 2002, [retrieved on Oct. 13, 2005]. Retrieved from the internet, <http://www.bio-itworld.com/archive/071102/firstbase.html>.*

Anomalous, "Drug Development: The Short Story 8. Combining the Figures and 6.", Network Sci. [online] 2004, [retrieved on Oct. 13, 2005]. Retrieved from the Internet, <http://www.netsci.org/scgi-bin/Courseware/projector.pl?Course_num=course1&Filename=sli=.*

Cheung et al., "N-(L-α-Aminoacyl) Derivatives of Methotrexate," Heterocycles 28(2):751-758 (1989).

* cited by examiner

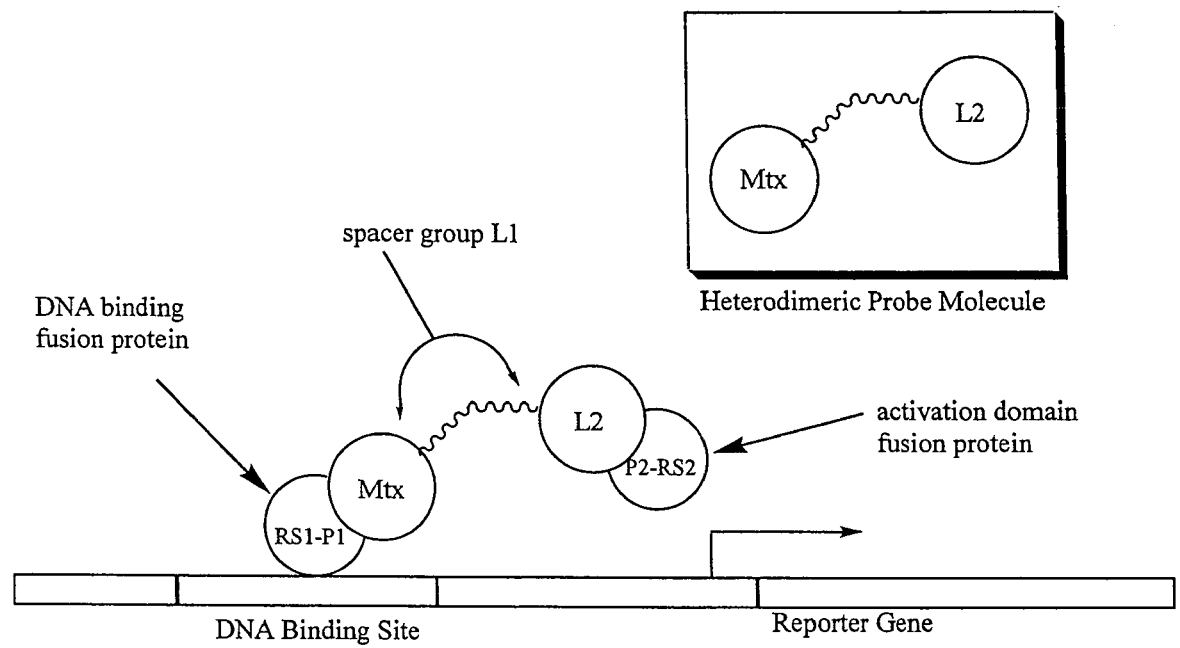
Figure I

SYNTHESIS OF METHOTREXATE-CONTAINING HETERODIMERIC MOLECULES

RELATED APPLICATION

This application claims priority from U.S. provisional application Ser. No. 60/407,131, filed on Aug. 28, 2002. The specification of which is incorporated by reference herein.

BACKGROUND OF THE INVENTION

A fundamental goal of pharmacology and medicine is to determine the cellular and molecular mechanisms of ligand-receptor interactions. At the cellular level, drug action is quite often the consequence of non-covalent interactions between therapeutically relevant small organic molecules and high-affinity binding proteins within a specific cell type. These small organic ligands may function as agonists or antagonists of key regulatory events which orchestrate both normal and abnormal cellular functions. For years, the pharmaceutical industry's approach to discovering such ligands has focused on random screenings of thousands of small molecules in specific in vitro and in vivo assays to determine potent lead compounds for their drug discovery efforts. Using these screenings, a lead compound may be found to exert well-defined effects with regard to a function at the cellular level (e.g., inhibition of cytokine production or DNA replication in a particular cancer cell line). However, such results may give little indication as to the mechanism of action at the molecular level (e.g., ligand-protein interaction).

Furthermore, screening for a compound's activity in one cellular function may not reveal its potential for cross-reactivities or its undesired side-effects. Such cross-reactivities and side-effects are often caused, for example, by proteins having closely similar structures to protein(s) under study, or by a single protein fulfilling different functions when expressed in different cell types or when localized to different sub-cellular compartments. Therefore, identifying possible protein targets for a pharmacological agent is challenging but highly desirable. There is an unmet need for a general and efficient method to identify the cellular targets for such pharmacological agents so as to accelerate the search for novel drugs at both the basic and applied levels of research.

Similarly, there is a need for a general approach to identifying a small molecule capable of binding any selected cellular target regardless of the target's biological function. Fowlkes et al. and Broach et al. describe a screening assay for identifying molecules capable of binding cell surface receptors so as to activate a selected signal transduction pathway. These references describe the modification of selected yeast signaling pathways so as to mimic steps in the mammalian signaling pathway. This approach is applicable only to certain signaling pathways and has limited utility for broader applications, such as discovering small molecules that interact with any cellular target. Thus, there is also need for general screening methods to determine the interaction between small molecules and target proteins so as to identify agonists and antagonists that may interfere or compete with the binding of the small molecules for these targets, and to identify new drugs that are capable of specific therapeutic effects in a variety of disease states.

Currently, few efficient methodologies exist for rapidly identifying a biological target such as a protein for a particular small molecule ligand. Existing approaches include the use of affinity chromatography, radio-labeled ligand binding and photoaffinity labeling in combination with protein purification methods to detect and isolate putative target proteins. This is followed by cloning of the gene encoding the target protein based on the peptide sequence of the isolated target. These approaches depend on the abundance of the putative target protein in the sample and are laborious and painstaking.

Crabtree et al. (WO 94/18317) describes a method to activate a target gene in cells comprising (a) the provision of cells containing and capable of expressing (i) at least one DNA construct comprising at least one receptor domain, capable of binding to a selected ligand, fused to a heterologous additional protein capable of initiating a biological process upon exposure of the fusion construct to the ligand, wherein the biological process comprises the expression of the target gene, wherein the ligand is capable of binding to two or more fusion proteins, and wherein the biological process is only initiated upon binding of the ligand to two or more fusion proteins, the two fusion proteins being the same or different, and (ii) the target gene under the expression control of a control element which is transcriptionally responsive to the initiation of said biological process; and (b) exposing said cells to said ligand in an amount effective to result in expression of the reporter gene. Further described are DNA constructs, ligands and kits useful for performing such method. In related documents, Crabtree et al. show these and other embodiments; specifically, Holt et al. describes the synthesis of hybrid ligands for use with the subject methods. The purpose envisaged for these methods and compositions is restricted to the investigation of cellular processes, the regulation of the synthesis of proteins of therapeutic or agricultural importance and the regulation of cellular processes in gene therapy. Nothing therein suggests the use of these methods and compositions to study the interaction of proteins with small molecules, particularly in its application to pharmaceutical research and drug development.

Licitra et al. describes a "three-hybrid screen assay" that implements the basic yeast two-hybrid assay system. (See Fields & Song, Fields et al., Gyuris et al., and Yang et al., for a description of the "two-hybrid assay") The significant difference is that instead of depending on the interaction between a so-called "bait" and a so-called "prey" protein, the transcription of the reporter gene is conditioned on the proximity of the two proteins, each of which can bind specifically to one of the two moieties of a small hybrid ligand. The small hybrid ligand constitutes the "third" component of the hybrid assay system. In that system, one known moiety of the hybrid ligand will bind to the "bait" protein, while the interaction between the other moiety and the "prey" protein can be exploited to screen for either a protein that can bind a known moiety, or a small moiety (pharmaceutical compound or drug) that can bind a known protein target. Licitra et al. used such an approach to targets for FK506 by fusing a rat glucocorticoid receptor (GR) gene to a lexA-based vector and screened a cDNA library from human leukemia Jurkat cells for proteins to induce reporter gene expression in the presence of a synthetic heterodimeric compound dexamethasone-FK506. Clones expressing a FK506-binding protein (FKBP12) were identified as a mediating partner of the interaction.

Weak affinity between FK506 and FKBP was a limitation of the three-hybrid system disclosed by Licitra et al. The FK506-FKBP interaction utilized by Licitra et al. provided only micromolar affinity. Higher affinity between bait protein and its binding partner is desired for improving system performance. Lin et al. improved upon the Licitra's dexamethasone-FK506 pair by synthesizing a methotrexate-dexamethasone heterodimeric probe molecule, also known as a chemical inducer of dimerization (CID). Lin et al.'s three-hybrid system consisted of a DNA binding protein-dihydrofolate reductase chimera (LexA-DHFR), a transcription activation protein-glucocorticoid binding protein chimera (B42-GR), and a heterodimeric probe molecule consisting of analogs of methotrexate and dexamethasone linked via a biphenyl linker. Dexamethasone and methotrexate have low nanomolar and picomolar affinities to their protein receptors GR and DHFR respectively. This system provided a significant improvement of system performance over Licitra et al.

There is a need to develop and synthesize heterodimeric probe molecules that have improved cell permeability, and toxicity, and are efficient chemical dimerizers of proteins in vivo.

SUMMARY OF THE INVENTION

The yeast three-hybrid system offers an attractive method for studying protein-ligand interactions in vivo. Heterodimeric probe molecules are an integral part of the system. Facile syntheses of these probe molecules allow for preparation of molecules with optimal membrane permeabilities, low toxicity, and dimerization efficiencies. The instant invention provides methotrexate-containing heterodimeric probe molecules and methods for preparing their intermediates. In certain embodiments the disclosed methods provide convergent synthetic steps. In certain embodiments the intermediates in the synthetic steps are soluble in standard organic solvents, making possible a more efficient isolation and purification of the intermediates and final products.

Accordingly, one aspect of the instant invention is a methotrexate-containing heterodimeric probe represented by the general structure shown in Formula I:

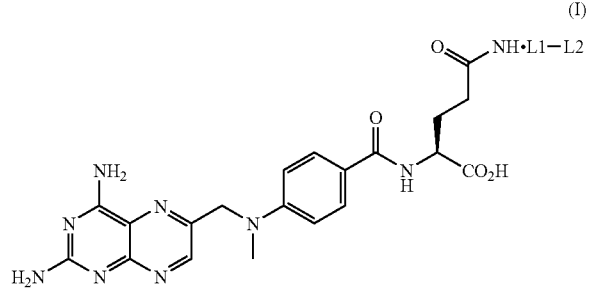

(I)

wherein L1 represents a spacer-linking group and L2 represents a putative or unknown small-molecule protein ligand.

The spacer-linking group is a hydrocarbylene group wherein one or more methylene groups is optionally replaced by a group Y (provided that none of the Y groups are adjacent to each other), wherein each Y, independently for each occurrence, is selected from substituted or unsubstituted aryl, heteroaryl, cycloalkyl, heterocycloalkyl, C(=X) (wherein X is $NR_1$, O or S), —O—, —OC(O)—, —$NR_1$—, —$NR_1CO$—, —$C(O)NR_1$—, —$S(O)_n$— (wherein n is 0, 1, or 2), —OC(O)—$NR_1$, —$NR_1$—C(O)—$NR_1$—, —$NR_1$—$C(NR_1)$—$NR_1$—, and —$B(OR_1)$—;

$R_1$, independently for each occurrence, represents H or a lower alkyl; and

L2 is a small molecule ligand for a protein receptor covalently attached to L1 via an alkyl, alkenyl, alkynyl, —O—, C(=X) (wherein X is $NR_1$, O or S), —OC(O)—, —$NR_1$—, —$NR_1CO$—, —$C(O)NR_1$—, —$S(O)_n$— (wherein n is 0, 1, 2, or 3), —$S(O)_2$—$NR_1$—, —$NR_1$—$S(O)_2$—, —OC(O)—$NR_1$, —$NR_1$—C(O)—$NR_1$—, —$NR_1$—$C(=NR_1)$—$NR_1$—, —$B(OR_1)_m$— (wherein m is 1 or 2), or —$P(O)_k$— (wherein k is 2 or 3) group.

In one embodiment, L1 comprises —$CH_2$—($CH_2$—W—$CH_2)_p$—$CH_2$—, wherein W represents N, O, or S, and p is an integer in the range of 1 to 8. Preferably, L1 consists essentially of such a moiety, or even more preferably represents a polyethylene glycol chain. Another aspect of the instant invention is a compound as shown in Formula II, which is an intermediate in the synthesis of the structure shown in Formula I.

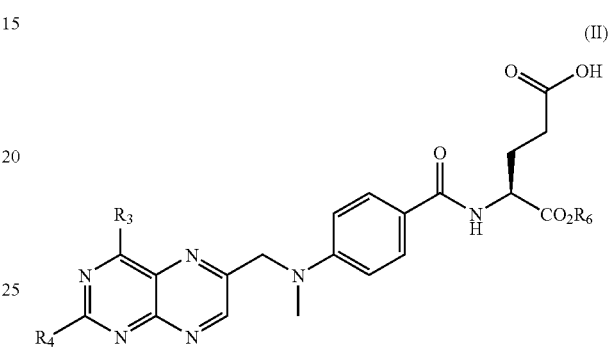

(II)

wherein,
$R_3$ and $R_4$ each represent $NR_5Z$;
$R_5$ is absent or represents hydrogen or lower alkyl;
Z represents t-Boc, Fmoc, Cbz, trialkylsilyl,

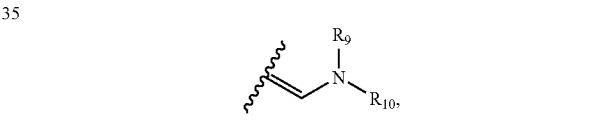

or an acid-labile amino-protecting group in exactly one occurrence, and for all other occurrences represents hydrogen;

$R_6$ represents an alkyl, aryl, trialkylsilylalkyl, or an acid-labile carboxy-protecting group; and $R_9$ and $R_{10}$, independently for each occurrence, represent hydrogen or (un)substituted alkyl, (un)substituted alkenyl, (un)substituted alkynyl, (un)substituted heteroalkyl, (un)substituted aryl, or (un)substituted heteroaryl.

Another aspect of the instant invention is a method for synthesizing the structure shown in Formula I:

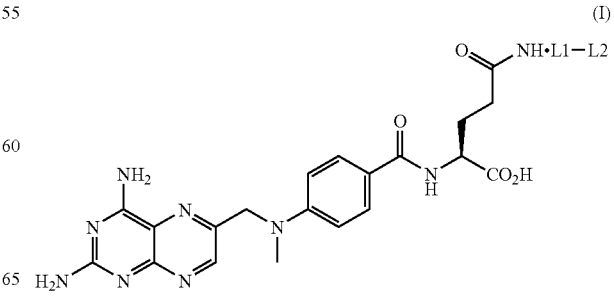

(I)

wherein,
L1 and L2 are as defined above;

comprising,
a. coupling the structure represented by Formula II with $H_2N$-L1-L2 to form an amide linkage;

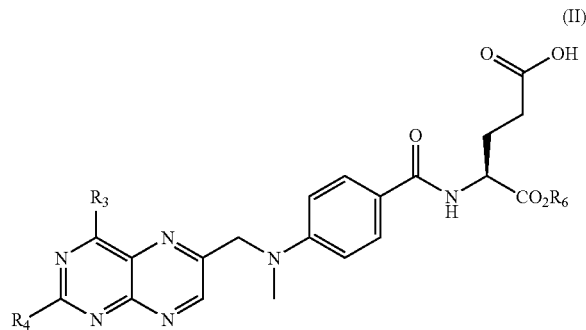

(II)

wherein, $R_3$, $R_4$ and $R_6$ are as defined above; and
b. removing protecting groups at the $R_3/R_4$ and $R_6$ positions.

In certain embodiments the amide linkage is formed using coupling reagents employed in peptide coupling reactions known in the art. (See Bodansky, Principles of Peptide Synthesis, $2^{nd}$ ed., Berlin; New York: Springer-Verlag, c1993; Bodansky, Peptide Chemistry: A practical textbook, $2^{nd}$ ed., Berlin; New York: Springer-Verlag, c1993) In preferred embodiments, the coupling reagents comprise N-ethyl-N-(3-dimethyl aminopropyl)-carbodiimide hydrochloride (EDC), N-Hydroxybenzotriazole Monohydrate (HOBT), and an alkyl amine such as diisopropylethylamine (DIEA).

In certain embodiments the $R_3$ or $R_4$ represent $NR_5Z$ wherein $R_5$ is hydrogen, and Z represents t-Boc in exactly one occurrence, and for all other occurrences represents hydrogen, and $R_6$ represents a t-butyl group. In certain embodiments, the protecting groups at $R_3/R_4$ and $R_6$ groups are removed using the same deprotecting reagent in a one-pot process. In certain embodiments, the deprotecting reagent is trifluoroacetic acid in an aqueous or halogenated hydrocarbon solvent such as dichloromethane. In certain preferred embodiments, the deprotecting agent is 90% TFA/ 10% $H_2O$. In other embodiments, the protecting groups at $R_3/R_4$ and $R_6$ are removed sequentially using two different deprotecting conditions.

Another aspect of the instant invention is a method for synthesizing the structure shown in Formula II:

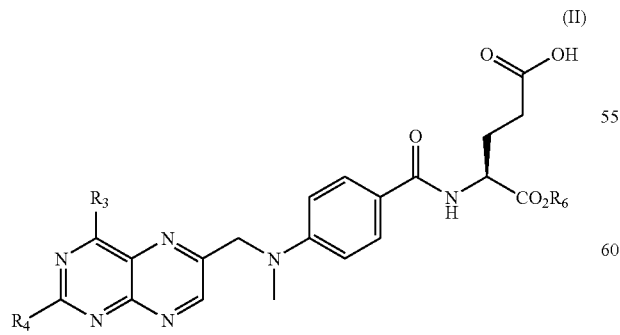

(II)

wherein
$R_3$ and $R_4$ each represent $NR_5Z$;
$R_5$ is absent or represents hydrogen or lower alkyl;

Z represents t-Boc, Fmoc, Cbz, trialkylsilyl,

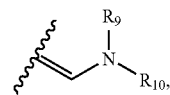

or an acid-labile amino-protecting group in exactly one occurrence, and for all other occurrences represents hydrogen;
$R_6$ represents an alkyl, aryl, trialkylsilylalkyl, or an acid-labile carboxy-protecting group; and
$R_9$ and $R_{10}$, independently for each occurrence, represent hydrogen or (un)substituted alkyl, (un)substituted alkenyl, (un)substituted alkynyl, (un)substituted heteroalkyl, (un)substituted aryl, or (un)substituted heteroaryl;

comprising
a. Reacting the structure represented by Formula IIa with $Boc_2O$ (1 equiv), an alkyl amine base such as diisopropylethylamine (DIEA), and a nucleophilic catalyst such as dimethylaminopyridine (DMAP) in a suitable organic solvent (preferably a halogenated hydrocarbon);

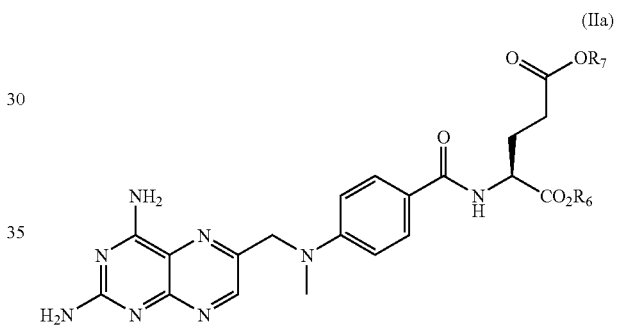

(IIa)

wherein $R_7$ represents an alkyl, aryl, trialkylsilylalkyl, or an acid-labile carboxy-protecting group; and
b. Removing $R_7$ to yield the structure represented by Formula II.

BRIEF DESCRIPTION OF THE FIGURE

FIG. 1 shows a schematic of a candidate small molecule ("L2") linked to a known small molecule ("MTX") via a spacer group ("L1").

DETAILED DESCRIPTION OF THE INVENTION

A. Overview

In general the invention provides a three-hybrid assay system and reagents for the identification of the protein binding partner of a predetermined small organic molecule. Likewise, the invention also provides methods and reagents for the identification of small organic molecule binding partners of a predetermined protein. Once such partner is detected, the invention further provides methods for monitoring the interaction of the pharmaceutical agent and its protein binding partner that can be used to detect competitors of the interaction.

According to one aspect of the invention, a compound binding to a known target polypeptide can be selected from a pool/library of candidate compounds. Preferably, the compound is a small molecule (see definition below). In this aspect of the invention, each candidate small molecule (designated "L2" hereafter) is linked to a known small molecule (designated "MTX" hereafter) via a linker sequence (designated "L1" hereafter) as shown in FIG. 1. The resulting MTX-L1-L2 compound is then allowed to contact a fusion polypeptide P1-RS1, comprising the known polypeptide binding partner of MTX, P1, fused to a first part of a reporter system (RS), RS1, and the target polypeptide (designated "P2" hereafter) fused to a second part of RS, RS2, in a suitable environment (such as a cell). The RS is designed such that when RS1 and RS2 are brought into spatial proximity in a suitable environment, the RS is activated and triggers a biologically detectable event. If L2 interacts with P2 with strong enough affinity, then RS1 is brought into close vicinity with RS2 via the bridging effect of the MTX-L1-L2 hybrid, thereby triggering the activation of RS. Hence, contacting the environment (i.e., a cell) containing the RS, the P1-RS1-hybrid and the P2-RS2-hybrid with a pool/library of MTX-L1-L2-hybrids and observing activation of RS facilitates the isolation of MTX-L1-L2-hybrids, wherein R2 is able to specifically bind to P2.

In one embodiment, the L2 is a transcription-based reporter system, such as a yeast two-hybrid system. In one embodiment, the linker sequence is particularly suitable for in vivo use of the chemical compound due to its increased solubility and enhanced membrane permeability.

In one embodiment, the P1-MTX interaction is a non-covalent interaction. In an alternative embodiment, the P1-MTX interaction results in a covalent bond. In one embodiment, the chemical library is synthesized. In another embodiment, the chemical library is derived or isolated from natural sources.

According to another aspect of the invention, a polypeptide binding to a predetermined target small molecule L2 can be selected from a library/libraries of test polypeptides. In this aspect, the target small molecule L2 is linked by a linker sequence L1 to a known small molecule MTX to form an MTX-L1-L2 hybrid compound, which is then allowed to contact polypeptide P1, the known binding partner of known small molecule MTX, fused to RS1, in a suitable environment. A library or libraries of test polypeptides P2, each fused to RS2, are translationally provided to the same environment. Binding between the target small molecule L2 and any member polypeptide P2 of the library/libraries will bring the P2-RS2 hybrid into the vicinity of the P1-RS1-hybrid, thereby triggering the activation of a reporter system RS. Hence, contacting cells containing the RS, the P1-RS1-hybrid and a pool/library of P2-RS2-hybrids with the MTX-L1-L2-hybrid and observing activation of RS facilitates the isolation of P2-RS2-hybrids, wherein P2 is able to specifically bind to L2.

In one embodiment, the RS2 is a transcription-based reporter system, such as yeast two-hybrid system.

In one embodiment, the linker sequence is particularly suitable for in vivo use of the chemical compound due to its increased solubility and enhanced membrane permeability.

In one embodiment, the P1-MTX interaction is a non-covalent interaction. In a related embodiment, the P1-MTX interaction results in a covalent bond. In one embodiment, the polypeptide library is a cDNA library or genomic DNA library. In another embodiment, the polypeptide library is synthesized randomly or semi-randomly. The library may contain different number of members, preferably from 2 to 10 members, or 10 to 500 members, 500 to 10,000 members or more than 10,000 members. The above described methods are not only suitable to identify an unknown member of a polypeptide ligand pair (screen method), but also suitable to determine if a given polypeptide binds a given ligand (assay or test method).

According to yet another aspect of the invention, there is provided a kit for detecting and/or selecting interactions between polypeptides and small molecules using either one of the above-mentioned methods.

According to another aspect of the invention, there is provided a method for pharmaceutical research wherein interactions between polypeptides and small molecules are monitored to facilitate further characterization and/or optimization of binding of at least one of the identified binding partners. This can be useful in a variety of situations. For example, many drugs or chemical compounds have noticeable, sometimes even severe, undesirable side-effects. This is likely caused by the fact that the drug may non-discriminately bind proteins other than the intended target. The instant invention provides a method to identify all potential binding partners of a given drug or chemical compound, thereby providing a basis to design other related drugs that do not bind these non-intended targets to avoid the nondesirable side-effects. In other cases, a drug may have some efficacy for certain conditions, but the mechanism of action of the drug is unknown, making it difficult to optimize the drug for a better efficacy. The instant invention provides a method to identify the target of the drug, thereby offering a means to further study the biology and the related signaling pathways so that drug optimization can be achieved based on knowledge gained through research on those signaling pathways.

Furthermore, information on the binding of ligands to polypeptide ligand binding domains that is collected by practicing the methods of the invention may be used to better understand the function or side effects of a ligand in a biological or therapeutic setting. Information thus collected may for example, be used to provide more informed prescription of medicaments comprising the ligand or with appropriate additional medicaments to provide more effective combination therapies. Thus, the instant invention can be used to optimize binding, or identify the target(s) of any one or more of the following: a compound with a known biological target, a compound with an unknown mechanism of action, a compound which binds to more than one polypeptide, a drug candidate compound, or a compound that binds to an unknown protein.

The instant invention also provides hybrid ligands which bind to or inhibit a kinase. For example, L2 can be a compound known to bind or inhibit kinases, or a derivative thereof with minor structural modifications. A typical kinase target can be a cyclin-dependent kinase.

Furthermore, the instant invention also provides a method to identify novel modulators of certain known proteins and a method to produce pharmaceutical formulations of such modulators.

Another aspect of the invention provides a method to identify a compound which inhibits the interaction between a ligand and a polypeptide, wherein the interaction is identified using any suitable method of the instant invention, comprising: 1) identifying, by any one of the suitable methods of the instant invention, a polypeptide that interacts with a predetermined ligand, or identifying a ligand that interacts with a predetermined polypeptide; 2) providing an environment wherein said interaction occurs; 3) contacting the environment with a test compound; 4) determining if said test compound inhibits said interaction, thereby identifying a compound which inhibits the interaction between a ligand and a polypeptide. In certain embodiments, the method further includes formulating the identified compound in a pharmaceutical preparation, and or administering the compound to a mammal, such as a human, in need of treatment.

In one embodiment, the ligand is a non-peptide ligand. In a preferred embodiment, the ligand is of the general structure MTX-L1-L2, wherein MTX, L1, and L2 are as defined above.

In one embodiment, the test compound is from a variegated library, which, for example, can be a nucleic acid library (cDNA, genomic DNA, EST, etc.) encoding polypeptides; a polypeptide library (synthetic, natural, random, semi-random, etc.); a small chemical library (natural, synthetic, etc.).

In one embodiment, the environment is a cell. In a related embodiment, the environment contains any one of the suitable hybrid ligand screening system of the instant invention (including reporter systems).

The inhibitory effect of the test compound can be assessed based on the change of status of the reporter system (see detailed descriptions below).

This method can be useful in a variety of situations. For example, if a small chemical compound is initially identified as possessing certain biological activity when administered to a cell, its protein target(s) can be identified. In case that multiple targets are present and only one target interaction is desired (for example, other target protein interactions lead to undesirable side effects), a test compound can be identified using this method so that it may specifically blocks those undesirable interactions while still allow the intended interaction to occur. In another scenario, after the identification of the polypeptide target of a known ligand, a compound can be identified using the subject method to block the interaction between such ligand and polypeptide, either to eliminate the undesirable effect of ligand-polypeptide interaction, or to reversibly control such interaction.

Another aspect of the invention provides a method to identify a polypeptide sequence that binds to a predetermined ligand, comprising: 1) providing a hybrid ligand with the general structure MTX-L1-L2, wherein L2 is a predetermined ligand and L1 is a linker, preferably a linker having the general formula $CH_2$—(—$CH_2$—W—$CH_2$—)$_p$—$CH_2$, wherein W and p are as defined above; 2) introducing the hybrid ligand into a population of cells, each cell containing a three-hybrid ligand screening system as defined above, wherein both P1 and P2 (as defined above) represent the same test polypeptide; 3) allowing the hybrid ligand to contact P1 and P2 in said ligand screening system, 4) identifying a positive ligand binding cell in which a detectable change in the status of the reporter system of the ligand screen system occurs; thereby identifying a nucleic acid encoding the test polypeptide.

In a related aspect of the invention, there is provided a method to determine if a ligand binds to a polypeptide, comprising: providing a hybrid ligand with the general structure MTX-L1-L2, wherein L2 is a predetermined ligand and L1 is a linker, preferably a linker having the general formula $CH_2$—(—$CH_2$—W—$CH_2$—)$_p$—$CH_2$, wherein W and p are as defined above; 2) introducing the hybrid ligand into an environment containing a test polypeptide, wherein multimerization (preferably dimerization) of the polypeptide lead to a detectable change; 3) determining if said detectable change occurs, thereby determining if the ligand binds to the test polypeptide.

In a related aspect, a similar method can be used to determine if a known polypeptide interacts with a test hybrid ligand.

In one embodiment, the detectable change is an enzymatic activity of the test polypeptide, which activity is only present when said polypeptide is multimerized (for example, dimerized). In a related embodiment, the polypeptide can be linked to any one of the suitable hybrid ligand screen systems described above so that multimerization of the polypeptide by the hybrid ligand leads to the activation of the reporter system.

In one embodiment, the polypeptide is an enzyme that is inactive as a monomer, and is only activated as a multimer, preferably a dimer. In this embodiment, it may suffice to use only a single polynucleotide in a method of the invention. For example, where one is searching for a new ligand for a polypeptide of interest for which a ligand is already known, one could use a polynucleotide encoding the polypeptide of interest fused to an enzyme that is active only as a multimer, preferably a dimer, and which does not dimerize spontaneously (e.g., a reduced affinity mutant). If this fusion polypeptide is contacted with a hybrid ligand MTX-L1-L2 of the invention, where R1 is the known ligand for the polypeptide of interest and R2 is a test ligand, activity of the enzyme will only be manifest if the test ligand binds the polypeptide of interest.

In one embodiment, the environment is a cell.

In one embodiment, the polypeptide comprises a receptor, preferably a receptor that requires multimerization to be functional or activated, such as a receptor that contains a cytoplasmic domain from one of the various cell surface membrane receptors as described in WO 94/18317. For example, many of these domains are tyrosine kinases or are complexed with tyrosine kinases, e.g., CD3 ζ, IL-2R, IL-3R, etc. For a review, see Cantley, et al., Cell (1991) 64, 281. Tyrosine kinase receptors which are activated by cross-linking, e.g., dimerization (based on nomenclature first proposed by Yarden and Ullrich, Annu. Rev. Biochem. (1988) 57, 443, include subclass 1: EGF-R, ATR2/neu, HER2/neu, HER3/c-erbB-3, Xmrk; subclass II: insulin-R, IGF R insulin-like growth factor receptor], IRR; subclass III: PDGF-R-A, PDGF-R-B, CSF R (M-CSF/c-Fms), c-kit, STK-1/Flk-2; and subclass IV: FGF-R, flg [acidic FGFJ, bek [basic FGF]); neurotrophic tyrosine kinases: Trk family, includes NGF-R, Ror1,2. Receptors which associate with tyrosine kinases upon cross-linking include the CD3ζ-family: CD3ζ and CD3η (found primarily in T cells, associates with Fyn) β and –γ chains of Fcε RI (found primarily in mast cells and basophils); γ chain of Fcγ RIII/CD16 (found primarily in macrophages, neutrophils and natural killer cells); CD3γ, δ, and ε (found primarily in T cells); Ig-a/MB-1 and Ig-P/B29 (found primarily in B cell). Alternatively, a cytokine-receptor may be utilized to detect ligand and receptor interactions as described in Eyckerman et al (Nature Cell Biology 2001; 3: 1114–1119).

B. Definitions (i) General Terms

The term "agonist", as used herein, is meant to refer to an agent that mimics or up-regulates (e.g., potentiates or supplements) the bioactivity of a protein of interest, or an agent that facilitates or promotes (e.g., potentiates or supplements) an interaction among polypeptides or between a polypeptide and another molecule (e.g., a steroid, hormone, nucleic acids, small molecules etc.). An agonist can be a wild-type protein or derivative thereof having at least one bioactivity of the wild-type protein. An agonist can also be a small molecule that up-regulates the expression of a gene or which increases at least one bioactivity of a protein. An agonist can also be a protein or small molecule which increases the interaction of a polypeptide of interest with another molecule, e.g., a target peptide or nucleic acid.

The term "amino-protecting group" as used herein refers to substituents of the amino group commonly employed to block or protect the amino functionality while reacting other functional groups of the molecule.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenyl-methoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, .alpha.-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical-so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference "Antagonist" as used herein is meant to refer to an agent that down-regulates (e.g., suppresses or inhibits) the bioactivity of a protein of interest, or an agent that inhibits/suppresses or reduces (e.g., destabilizes or decreases) interaction among polypeptides or other molecules (e.g., steroids, hormones, nucleic acids, etc.). An antagonist can also be a compound that down-regulates the expression of a gene of interest or which reduces the amount of the wild type protein present. An antagonist can also be a protein or small molecule which decreases or inhibits the interaction of a polypeptide of interest with another molecule, e.g., a target peptide or nucleic acid.

The term "biologically detectable event" is a general term used to describe any biological event that can be detected in an assay system, such as for example, without limitation, in a transcription-based yeast two-hybrid assay etc. A biologically detectable event means an event that changes a measurable property of a biological system, for example, without limitation, light absorbance at a certain wavelength, light emission after stimulation, presence/absence of a certain molecular moiety in the system, electrical resistance/capacitance, etc., which event is conditional on another, possibly non-measurable or less easily measurable property of interest of the biological system, for example, without limitation, the presence or absence of an interaction between two proteins.

Preferably, the change in the measurable property brought about by the biologically detectable event is large compared to natural variations in the measurable property of the system. Examples include the yellow color resultant from the action of β-galactosidase on o-nitrophenyl-β-D-galactopyranoside (ONPG) (J. H. Miller, Experiments in Molecular Genetics, 1972) triggered by transcriptional activation of the E. coli lacZ gene encoding β-galactosidase by reconstitution of a transcription factor upon binding of two proteins fused to the two functional domains of the transcription factor. Other examples of biologically detectable events are readily apparent to the person skilled in the art. Alternatively, other biological functions may be induced and detected following oligomerization, preferably dimerization, of the functional domains. For example, transcriptional regulation, secondary modification, cell localization, excocytosis, cell signaling, protein degradation or inactivation, cell viability, regulated apoptosis, growth rate, cell size. Such biological events may also be controlled by a variety of direct and indirect means including particular activities associated with individual proteins such as protein kinase or phosphatase activity, reductase activity, cyclooxygenase activity, protease activity or any other enzymatic reaction dependent on subunit association. Also, one may provide for association of G proteins with a receptor protein associated with the cell cycle, e.g., cyclins and cdc kinases, or multiunit detoxifying enzymes.

"Biological activity" or "bioactivity" or "activity" or "biological function", which are used interchangeably, for the purposes herein means a catalytic, effector, antigenic, molecular tagging or molecular interaction function that is directly or indirectly performed by a polypeptide (whether in its native or denatured conformation), or by any subsequence thereof.

The terms "cell death", "cell killing" or "necrosis" refer to the phenomenon of cells dying as a result of an extrinsically imposed loss of a particular cellular function essential for the survival of the cell.

"Cells," "host cells" or "recombinant host cells" are terms used interchangeably herein. It is understood that such terms refer not only to a particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Characterize" as used herein means a detailed study of a small molecule, a polypeptide or a nucleic acid (polynucleotide) encoding a polypeptide to reveal relevant chemical and biological information. This information generally includes one or more of, but is not limited to, the following: sequence information for protein and nucleic acid, primary, secondary, tertiary, and quarternary structure information, molecular weight, solubility in various solvents, enzymatic or other activity, isoelectric focusing point, binding affinity to other molecules, binding partners, stability, expression pattern, tissue distribution, subcellular localization, expression regulation, developmental roles, phenotypes of transgenic animals overexpressing or devoid of a polypeptide or nucleic acid, size of nucleic acid, and hybridization property of nucleic acid. A variety of standard chemistry, cell and molecular biology protocols and methodologies can be used, such as gel electrophoresis, capillary electrophoresis, cloning, restriction enzyme digestion, expression profiling by hybridization, affinity chromatography, HPLC, isoelectric focusing, mass spectrometry, automated sequencing, and the generation of transgenic animals, the details of which can be found in many standard chemistry and molecular biology laboratory manuals (see below). Techniques employing the hybridization of nucleic acids may, for example, utilize arrayed libraries of nucleic acids, such as oligonucleotides, cDNA or others (See, for example, U.S. Pat. No. 5,837,832).

The term "chemically similar" is used to refer to chemical compounds with similar chemical structures and/or chemical properties. Similarity can be judged by comparison between two compounds of several characteristics, such as electronic charge, steric size, stereochemistry, hydrogen bond donor/acceptor capability, and polarity (i.e., hydrophobicity/hydrophilicity). For example, chemically similar amino acids would have side chains which, judged by at least three, four, or preferably all five of these characteristics, are categorized in the same way. For example, under physiological conditions, glycine and alanine are similar judged by all five characteristics, glycine and phenylalanine differ only judged by steric size, glycine and tyrosine differ by steric size and hydrogen bond donor capability, and glycine and glutamic acid differ by steric size, charge, polarity, and hydrogen bond acceptor capability. For example, steroids are generally similar in terms of conformation, polarity, stereochemistry, charge, steric size, etc., although some steroids (individually or as subclasses) may differ slightly from "average" steroids (e.g., steroidal alkaloids are typically charged under physiological conditions).

In certain embodiments, chemically similar small molecule compounds share similar functional groups and/or ring systems and thus display a combination of structural elements disposed in similar orientations or conformations, thereby defining a structural class of compounds which differ slightly, e.g., by substituents appended to the structural core, or by slight variations in the structural core (such as changes in ring size, heteroatom substitutions, homologation, etc.). For example, beta-lactam antibiotics all share a four-membered lactam ring, macrolide antibiotics have a macrocyclic lactone (e.g., 10 to 18 members) substituted with multiple methyl and/or hydroxyl groups (some of the latter of which may be hydroxylated), peptides are chains of alpha-amino acids linked by amide bonds, etc., and each such group of compounds comprises chemically similar members.

The term "carboxy-protecting group" as used herein refers to a substituent which protects carboxy functionalities against undesirable reactions during synthetic procedures such as those carboxy-protecting groups disclosed in Greene, "Protective Groups in Organic Synthesis," (John Wiley & Sons, New York (1981)), which is incorporated herein by reference. Carboxy-protecting groups comprise 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-timethoxytrityl, 2-phenylprop-2-yl, trimethylsilyl, t-butyldimethylsilyl, 2,2,2-trichloroethyl, .beta.-(trimethylsilyl)ethyl, .beta.-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "deprotecting reagent" refers to a reagent which reacts with a protecting group to remove the group used to protect groups, carboxy or amino groups, against undesirable reactions during synthesis of the desired final product. Examples of deprotecting agents include but are not limited to n-tetrabutylammonium fluoride, acetic acid/THF/water, citric acid/methanol, Dowex resin/methanol, potassium carbonate/methanol, n-tetrabutylammonium chloride/potassium fluoride, hydrogen fluoride/acetonitrile, HCl, HBr, methanesulfonic acid, benzenesulfonic acid, trichloroacetic acid, trifluoroacetic acid, phosphoric acid and p-toluenesulfonic acid.

Further examples are disclosed in Greene, "Protective Groups in Organic Synthesis," (John Wiley & Sons, New York (1981)). The term "deprotecting conditions" refers to a reaction mixture wherein a deprotecting agent is present to remove a protecting group.

The term "derivative with minor modifications" with respect to a parent chemical compound, for example a small molecule, ligand, hybrid ligand, peptide or polypeptide, is used to refer to chemical compounds which are chemically similar to the parent chemical compound. Preferably, a derivative with minor modifications will have minor structural modifications and hence may be considered as "structural variants" of the original compound. Generally, such minor structural modifications are made in order to obtain a compound with overall similar properties as compared to the parent compound, but with a change with respect to a certain property of the parent compound that is disadvantageous or unwanted. For example, a hydrophilic side chain may be added to a certain chemical compound to increase its solubility, while retaining a desired biological activity as the side chain is added such as not to interfere with the binding between the compound and its biological target.

A "chimeric polypeptide", "fusion polypeptide" or "fusion protein" is a fusion of a first amino acid sequence encoding a first polypeptide with a second amino acid sequence defining a domain (e.g., polypeptide portion) foreign to and not substantially homologous with any domain of the first polypeptide. Such second amino acid sequence may present a domain which is found (albeit in a different polypeptide) in an organism which also expresses the first polypeptide, or it may be an "interspecies", "intergenic", etc. fusion of polypeptide structures expressed by different kinds of organisms. At least one of the first and the second polypeptides may also be partially or completely synthetic or random, i.e., not previously identified in any organism.

"To clone" as used herein, as will be apparent to skilled artisan, may be meant as obtaining exact copies of a given polynucleotide molecule using recombinant DNA technology. Furthermore, "to clone into" may be meant as inserting a given first polynucleotide sequence into a second polynucleotide sequence, preferably such that a functional unit combining the functions of the first and the second polynucleotides results, for example, without limitation, a polynucleotide from which a fusion protein may be translationally provided, which fusion protein comprises amino acid sequences encoded by the first and the second polynucleotide sequences. Details of molecular cloning can be found in a number of commonly used laboratory protocol books such as *Molecular Cloning: A Laboratory Manual*, 2nd. Ed., ed. by Sambrook, Fritsch and Maniatis (Cold Spring Harbor Laboratory Press: 1989).

"To clone" as used herein, as will be apparent to skilled artisan, may be also meant as obtaining identical or nearly identical population of cells possessing a common given property, such as the presence or absence of a fluorescent marker, or a positive or negative selectable marker. The population of identical or nearly identical cells obtained by cloning is also called a "clone." Cell cloning methods are well known in the art as described in many commonly available laboratory manuals (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999).

"Complementation screen" as used herein means genetic screening for one or several genes or source DNA that can confer a certain specified phenotype which will not exist without the presence of said one or several genes or source DNA. It is usually done in vivo, by introducing into cells lacking the specified phenotype a library of source DNA to be screened for, and identifying cells that have obtained a source DNA and now exhibit the specified phenotype. Alternatively, it could be done in vivo by randomly inactivating genes in the genome of the cell lacking the specified phenotype and identify cells that have lost the function of certain genes and exhibit the specified phenotype. However, a complementation screen can also be done in vitro in cell-free systems, either by testing each candidate individually or as pools of individuals.

"Recovering a clone of the cell . . . under conditions wherein a cell is selectable" as used herein is meant as selecting from a population of cells, a subpopulation or a single cell possessing a given property such as the presence or absence of fluorescent markers, or the presence or absence of positive or negative selectable markers, and obtaining a clone of each selected cell. The cells can be selected under conditions that will completely or nearly completely eliminate any cell that does not have the desired property of the cells to be selected. For example, by growing cells in selective media, only cells possessing a certain desired property will survive. The surviving cells can be cloned using standard cell and molecular biology protocols (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999). Alternatively, cells possessing a desired property can be selected from a population based on the observation of a certain discernable phenotype, such as the presence or absence of fluorescent markers. The selected cells can then be cloned using standard cell and molecular biology protocols (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999).

The term "equivalent" is understood to include polypeptides or nucleotide sequences that are functionally equivalent or possess an equivalent activity as compared to a given polypeptide or nucleotide sequence. Equivalent nucleotide sequences will include sequences that differ by one or more nucleotide substitutions, additions or deletions, such as allelic variants; and will, therefore, include sequences that differ from the nucleotide sequence of a particular gene, due to the degeneracy of the genetic code. Equivalent polypeptides will include polypeptides that differ by one or more amino acid substitutions, additions or deletions, which amino acid substitutions, additions or deletions leave the function and/or activity of the polypeptide substantially unaltered. A polypeptide equivalent to a given polypeptide could, for example, be the polypeptide that performs the same function in another species.

"Reporter moiety" as used herein means a feature that can be detected by certain means. For example, one routine assay for detection is achieved by western blot using antibody specific for a protein feature. Alternatively, the reporter moiety or a reporter moiety-containing moiety may be capable of capable exhibiting an intended detectable function. Particularly, the function may be suppressed or inhibited before a certain event occurs and the suppression or inhibition may be abolished after such event occurs. For example, without limitation, a transcription reporter moiety may be rendered non-functional when it is attached to a Cub moiety that is tethered to a membrane outside the nucleus of a target cell. It may become functional after cleavage of the reporter moiety from the Cub-moiety when it can freely translocate to the nucleus to exert its transcription activation/suppression function, which activity is in turn detectable by measuring the activity of a functionally linked reporter gene.

As used herein, the terms "gene", "recombinant gene" and "gene construct" refer to a nucleic acid comprising an open reading frame encoding a polypeptide, including both exon and (optionally) intron sequences. The term "intron" refers to a DNA sequence present in a given gene which is not translated into protein and is generally found between exons.

The term "high affinity" as used herein means strong binding affinity between molecules with a dissociation constant $K_D$ of no greater than 1 µM. In a preferred case, the $K_D$ is less than 100 nM, 10 nM, 1 µM, 100 pM, or even 10 pM or less. In a most preferred embodiment, the two molecules can be covalently linked ($K_D$ is essentially 0). "Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of structurally related amino acids at positions shared by the amino acid sequences. An "unrelated" or "non-homologous" sequence shares less than 40% identity, though preferably less than 25% identity with another sequence.

The term "interact" as used herein is meant to include all interactions (e.g., biochemical, chemical, or biophysical interactions) between molecules, such as protein—protein, protein-nucleic acid, nucleic acid-nucleic acid, protein-small molecule, nucleic acid-small molecule or small molecule-small molecule interactions.

The term "isolated" as used herein with respect to nucleic acids, such as DNA or RNA, refers to molecules separated from other DNAs or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Kit" as used herein means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

"Instruction(s)" as used herein means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

"Library" as used herein generally means a multiplicity of member components constituting the library which member components individually differ with respect to at least one property, for example, a chemical compound library. Particularly, as will be apparent to skilled artisan, "library" means a plurality of nucleic acids/polynucleotides, preferably in the form of vectors comprising functional elements (promoter, transcription factor binding sites, enhancer, etc.) necessary for expression of polypeptides, either in vitro or in vivo, which are functionally linked to coding sequences for polypeptides. The vector can be a plasmid or a viral-based vector suitable for expression in prokaryotes or eukaryotes or both, preferably for expression in mammalian cells. There should also be at least one, preferably multiple pairs of cloning sites for insertion of coding sequences into the library, and for subsequent recovery or cloning of those coding sequences. The cloning sites can be restriction endonuclease recognition sequences, or other recombination based recognition sequences such as loxP sequences for Cre recombinase, or the Gateway system (Life Technologies, Inc.) as described in U.S. Pat. No. 5,888,732, the contents of which are incorporated by reference herein. Coding sequences for polypeptides can be cDNA, genomic DNA fragments, or random/semi-random polynucleotides. The methods for cDNA or genomic DNA library construction are well-known in the art, which can be found in a number of commonly used laboratory molecular biology manuals (see below).

The term "modulation" as used herein refers to both upregulation (i.e., activation or stimulation, e.g., by agonizing or potentiating) and down-regulation (i.e., inhibition or suppression, e.g., by antagonizing, decreasing or inhibiting) of an activity.

The term "kinase" as used herein refers to an enzyme that transfers a phosphate group from a nucleoside triphosphate to another molecule. Preferably, the kinase is selected from the following list: AMP-PK (AMP-activated protein kinase, acetyl-CoA carboxylase kinase-3, HMG-CoA reductase kinase, hormone-sensitive lipase kinase), ACK2 (acetyl-CoA carboxylase kinase-2), AFK (actin-fragmin kinase), APL-A1 (Aplysia Californica cAMP-dependent PK 1), APL-A2 (Aplysia Californica cAMP-dependent PK 2), CAK (Cdk-activating kinase), CAMII (=CaM-II), beta-ARK1 (beta-adrenergic receptor kinase 1=GRK2), beta-ARK2 (beta-adrenergic receptor kinase 2=GRK3), c-Abl (cellular Abl), c-Raf (cellular Raf), c-Src (cellular Src), Cdk (cyclin dependent kinase), cdc2 (cell division cycle protein kinase), CK (casein kinase), CK-I or CKI (casein kinase I), CK-II or CKII (casein kinase II), CTD kinase ((RNA polymerase II) carboxy-terminal domain kinase), CaM-I (calmodulin-dependent protein kinase I), CaM-II (calmodulin-dependent protein kinase II, calmodulin-dependent multiprotein kinase, CaM-MPK), CaM-III (calmodulin-dependent protein kinase III, EF-2 kinase), DNA-PK (DNA-dependent protein kinase), ds-DNA kinase (double-stranded DNA-activated protein kinase), ds-RNA kinase (double stranded RNA-activated protein kinase, p68 kinase), EGF-R or EGFR (epidermal growth factor receptor), ERK (extracellular signal regulated kinase=MAPK), ERT PK (growth factor-regulated kinase), FAK (focal adhesion kinase), GRK1 (G protein-coupled receptor kinase 1=RK), GRK2 (G protein-coupled receptor kinase 2=beta-ARK1), GRK3 (G protein-coupled receptor kinase 3=beta-ARK2), GRK4 (G protein-coupled receptor kinase 4), GRK5 (G protein-coupled receptor kinase 5), GRK6 (G protein-coupled receptor kinase 5), GSK1 (glycogen synthase kinase 1=PKA), GSK2 (glycogen synthase kinase 2=PHK), GSK3 (glycogen synthase kinase 3), GSK4 (glycogen synthase kinase 4), GSK5 (glycogen synthase kinase 5=CKII), H1-HK (growth-associated H1 histone kinase (MPF), cdc2+/CDC28 protein kinase) H4-PK (histone-H4-specific, protease activated protein kinase), H4-PK-I (histone H4 kinase I), H4-PK-II (histone H4 kinase II), HCR (home-controlled repressor, heme-regulated eIF-2-alpha kinase), HKII (histone kinase II), INS-R or INSR (insulin receptor), Jak1 (Janus protein-tyrosine kinase 1), Jak2 (Janus protein-tyrosine kinase 2), LCK/FYN (LYMPHOCYTE-SPECIFIC PROTEIN TYROSINE KINASE P56LCK), MAPK (mitogen-activated protein kinase (MAP kinase)=ERK), MAPKAPK-1 (MAP kinase-activated protein kinase 1=S6K-II), MAPKAPK-2 (MAP kinase-activated protein kinase 2), MEK (MAP, Erk kinase, MAP kinase kinase), MFPK (multifunctional protein kinase), MHCK (myosin heavy chain kinase), mlCK (myosin light chain kinase), p135tyk2 (135 kD tyk2 tyrosine-protein kinase), p34cdc2 (34 kD cell division cycle protein kinase), p42cdc2 (42 kD cell division cycle protein kinase), p42mapk (42 kD MAP kinase isoform), p44 mpk (44 kD meiosis-activated myelin basic protein kinase=ERK1), p60-src (tyrosine-protein kinase src), p74raf-1 (74 kDa protein kinase Raf isoform), PDGF-R or PDGFR (platelet-derived growth factor receptor), PHK (phosphorylase kinase), PI-3 kinase (phosphatidylinositol 3' kinase), PKA (cAMP-dependent protein kinase, protein kinase A), PKC (protein kinase C), PKG (cGMP-dependent protein kinase), PRK1 (lipid-activated PKC-related kinase), Raf (protein kinase Raf), RK (rhodopsin kinase=GRK1), RS kinase (nuclear envelope-bound protein kinase), S6K (S6 kinase), S6K-II (S6-kinase 2=MAPKAPK-1), v-Src (viral Src). The term to "bind to or inhibit a kinase" refers to the ability of certain compounds to bind to kinases with high affinity, and the further property of certain compounds to lower the activity of a kinase. The "or" therein is not meant exclusive, i.e., a compound may both bind to a kinase and inhibit it, or it may only bind, or it may only inhibit such kinase, as the case may be.

(ii) Chemical Terms

An aliphatic chain comprises the classes of alkyl, alkenyl and alkynyl defined below. A straight aliphatic chain is limited to unbranched carbon chain radicals. As used herein, the term "aliphatic group" refers to a straight chain, branched-chain, or cyclic aliphatic hydrocarbon group and includes saturated and unsaturated aliphatic groups, such as an alkyl group, an alkenyl group, and an alkynyl group.

Alkyl refers to a fully saturated branched or unbranched carbon chain radical having the number of carbon atoms specified, or up to 30 carbon atoms if no specification is made. For example, alkyl of 1 to 8 carbon atoms refers to radicals such as methyl, ethyl, propyl, butyl, pentyl, hexyl, heptyl, and octyl, and those radicals which are positional isomers of these radicals. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, a cyano, a nitro, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxyls, alkylthios, aminoalkyls, carbonyl-substituted alkyls, —$CF_3$, —CN, and the like.

Unless the number of carbons is otherwise specified, "lower alkyl", as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

Alkenyl refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

Alkynyl refers to hydrocarbyl radicals of the scope of alkenyl, but having 1 or more triple bonds in the radical.

The terms "alkoxyl" or "alkoxy" as used herein refers to an alkyl group, as defined below, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "amine" and "amino" are art-recognized and refer to both unsubstituted and substituted amines, e.g., a moiety that can be represented by the general formulae:

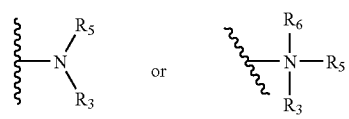

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In preferred embodiments, only one of $R_3$ or $R_5$ can be a carbonyl, e.g., $R_3$, $R_5$ and the nitrogen together do not form an imide. In even more preferred embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a $pK_a \geq 7.00$. The protonated forms of these functional groups have $pK_a$s relative to water above 7.00.

The term "carbonyl" is art-recognized and includes such moieties as can be represented by the general formula:

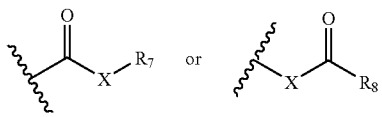

wherein X is a bond or represents an oxygen or a sulfur, and $R_7$ represents a hydrogen, an alkyl, an alkenyl, —$(CH_2)_m$—$R_1$ or a pharmaceutically acceptable salt, $R_8$ represents a hydrogen, an alkyl, an alkenyl or —$(CH_2)_m$—$R_1$, where in and $R_1$ are as defined above. Where X is an oxygen and $R_7$ or $R_8$ is not hydrogen, the formula represents an "ester". Where X is an oxygen, and $R_7$ is as defined above, the moiety is referred to herein as a carboxyl group, and particularly when $R_7$ is a hydrogen, the formula represents a "carboxylic acid". Where X is an oxygen, and $R_8$ is hydrogen, the formula represents a "formate". In general, where the oxygen atom of the above formula is replaced by sulfur, the formula represents a "thiocarbonyl" group. Where X is a sulfur and $R_7$ or $R_8$ is not hydrogen, the formula represents a "thioester" group. Where X is a sulfur and $R_7$ is hydrogen, the formula represents a "thiocarboxylic acid" group. Where X is a sulfur and $R_8$ is hydrogen, the formula represents a "thioformate" group. On the other hand, where X is a bond, and $R_7$ is not hydrogen, the above formula represents a "ketone" group. Where X is a bond, and $R_7$ is hydrogen, the above formula represents an "aldehyde" group.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, or the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "hydrocarbyl" refers to a monovalent hydrocarbon radical comprised of carbon chains or rings of up to 26 carbon atoms to which hydrogen atoms are attached. The term includes alkyl, cycloalkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "hydrocarbylene" refers to a divalent hydrocarbyl radical. Representative examples include alkylene, phenylene, or cyclohexylene. Preferably, the hydrocarbylene chain is fully saturated and/or has a chain of 1–10 carbon atoms.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

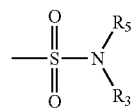

in which $R_3$ and $R_5$ are as defined above.

The term "sulfate" is art recognized and includes a moiety that can be represented by the general formula:

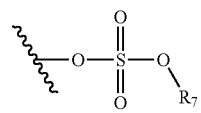

in which $R_7$ is as defined above.

The term "sulfonamido" is art recognized and includes a moiety that can be represented by the general formula:

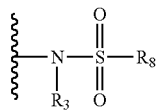

in which $R_2$ and $R_4$ are as defined above.

The term "sulfonate" is art-recognized and includes a moiety that can be represented by the general formula:

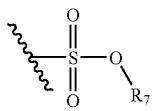

in which $R_7$ is an electron pair, hydrogen, alkyl, cycloalkyl, or aryl.

The terms "sulfoxido" or "sulfinyl", as used herein, refers to a moiety that can be represented by the general formula:

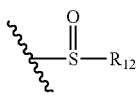

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

C. Exemplary Embodiments (i) Transcriptional and Reporter Systems

According to the invention, a reporter system is used to detect the proximity of two polypeptides P1 and P2 (as defined above) when a small molecule compound is present so that either the small molecule compound or one of the polypeptides can be identified and further characterized.

The following sections will describe a variety of reporter systems that can be used in the invention. It will be readily apparent to the skilled artisan that the immediate invention may also be used in conjunction with other reporter systems, even those that are developed in the future.

(i.a) Transcription-Based Reporter Systems

According to the invention, a transcription based reporter system can be used to detect whether P1 and P2 are within close range of each other. A typical transcription-based reporter system is yeast two-hybrid system, which is well-known in the art (see below). In that respect, P1 and P2 are both synthesized as fusion proteins, one fused to a DNA binding domain, the other fused to a transcription activation domain. The DNA binding domain will bind to the promoter region of a reporter gene. If P1 and P2 are with close range of each other (via binding to MTX-L1-L2), then the transcription activation domain will be able to activate the transcription of a reporter gene, which will facilitate the identification of either the test protein or the test small chemical compound. Due to the symmetric nature of the system, there shall be no limitation as to whether P1 or P2 is fused to the DNA binding domain or the transcription activation domain. In addition, both P1 and P2 can be synthesized as either N- or C-terminal fusion proteins.

Detailed description of various components of yeast two hybrid system can be readily found elsewhere. For example, *The Yeast Two-Hybrid System* (*Advances in Molecular Biology*), Ed. Paul L. Bartel and Stanley Fields, Oxford University Press, 1997, is a book devoted solely to the yeast two-hybrid system. Pioneers in the field provide detailed protocols, practical advice on troubleshooting, and suggestions for future development. In addition, they illustrate how to construct an activation domain hybrid library, how to identify mutations that disrupt an interaction, and how to use the system in mammalian cells. Chapter topics include characterizing hormone/receptor complexes; identifying peptide ligands; and analyzing interactions mediated by protein modifications. Equally valuable two-hybrid techniques and variations can also be found in *Yeast hybrid technologies* (Zhu, L., and Hannon, G. J., Eds., Biotechniques Press, Westborough, Mass., USA, 2000). A third book, *Two-Hybrid Systems, Methods and Protocols* (*Methods in Molecular Biology Vol.* 177), Ed. Paul MacDonald, Humana Press, 2001, provides some recent updates to the field of yeast two-hybrid assay.

Other versions of yeast two-hybrid systems are also described. For example, the reverse yeast two-hybrid system is described in U.S. Pat. Nos. 5,955,280 and 5,965,368, the contents of which are incorporated herein in their entirety. These patents disclosed methods for identifying molecular interactions (e.g., protein/protein, protein/DNA, protein/RNA, or RNA/RNA interactions), all of which employ selection and counter-selection and at least two hybrid molecules. Similar to the conventional yeast two-hybrid system, reverse two-hybrid systems also involve molecules which interact to reconstitute a transcription factor and direct expression of a reporter gene, the expression of which is then assayed. Also disclosed by these patents are genetic constructs which are useful in practicing the methods of the invention.

Licitra and Liu (WO 97/41255, and U.S. Pat. No. 5,928,868) also described a "three-hybrid screen assay" in which the basic yeast two-hybrid assay system is implemented. The significant difference is: instead of depending on the interaction between a so-called "bait" and a so-called "prey" protein, the transcription of the reporter gene is conditioned on the proximity of the two proteins, each of which can bind specifically to one of the two moieties of a small hybrid ligand. The small hybrid ligand constitutes the "third" component of the hybrid assay system. In that system, one known moiety of the hybrid ligand will bind to the "bait" protein, while the interaction between the other moiety and the "prey" protein can be exploited to screen for either a protein that can bind a known moiety, or a small moiety (pharmaceutical compound or drug) that can bind a known protein target.

For example, with respect to protein interaction technologies, Bartel and Fields summarize many different approaches/variations of the available two-hybrid systems in *The yeast-two-hybrid system* (Bartel, P. L., and Fields, S., Eds., Oxford University Press, New York, N.Y., USA, 1997). Equally valuable two-hybrid techniques and variations can also be found in *Yeast hybrid technologies* (Zhu, L., and Hannon, G. J., Eds., Biotechniques Press, Westborough, Mass., USA, 2000).

Further systems include WO 96/02561 (The General Hospital Corporation; Brent et al, Two hybrid system using conformationally constrained proteins as one of the hybrids); EP 0646644 (Bristol Myers Squibb, Menzel, periplasmic membrane bound interaction system); WO 9825947 (Bristol Myers Squibb, Kornacker, prokaryotic two-hybrid system using *E. coli* and other cells); WO 98/07845 (Dove, an interaction trap system or "ITS" which is derived using recombinantly engineered prokaryotic cells); WO 98/34120 (Michnick, describe a strategy for designing and implementing protein-fragment complementation assays (PCAs) to detect biomolecular interactions in vivo and in vitro—the DHFR protein interaction screening system. The design, implementation and broad applications of this strategy are illustrated with a large number of enzymes with particular detail provided for the example of murine dihydrofolate reductase (DHFR). Fusion peptides consisting of N- and C-terminal fragments of murine DHFR fused to GCN4 leucine zipper sequences were coexpressed in *Escherichia coli* grown in minimal medium, where the endogenous DHFR activity was inhibited with trimethoprim. Coexpression of the complementary fusion products restored colony formation. Survival only occurred when both DHFR fragments were present and contained leucine-zipper forming sequences, demonstrating that reconstitution of enzyme activity requires assistance of leucine zipper formation. DHFR fragment-interface point mutants of increasing severity (Ile to Val, Ala and Gly) resulted in a sequential increase in *E. coli* doubling times illustrating the successful DHFR fragment reassembly rather that non-specific interactions between fragments. This assay could be used to study equilibrium and kinetic aspects of molecular interactions including protein—protein, protein-DNA, protein-RNA, protein-carbohydrate and protein-small molecule interactions, for screening cDNA libraries for binding of a target protein with unknown proteins or libraries of small organic molecules for biological activity. The selection and design criteria applied here is developed for numerous examples of clonal selection, colorometric, fluorometric and other assays based on enzymes whose products can be measured. The development of such assay systems is shown to be simple, and provides for a diverse set of protein fragment complementation applications); WO 98/39483 (Ventana, Alexander Kamb, methods for identifying nucleic acid sequences that affect a cellular phenotype are disclosed. The method uses a reporter gene whose level of expression correlates with the phenotype in conjunction with a method or device for measuring the level of reporter expression); WO 98/44350 (Helen Blau, enzyme complementation assay in which methods and compositions for detecting molecular interactions, particularly protein—protein interactions, are provided. The invention allows detection of such interactions in living cells or in vitro. Detection of molecular interactions in living cells is not limited to the nuclear compartment, but can be accomplished in the cytoplasm, cell surface, organelles, or between these entities. In one embodiment, the method utilizes novel compositions comprising fusion proteins between the molecules of interest and two or more inactive, weakly-complementing β-galactosidase mutants. Association between the molecules of interest brings the complementing β-galactosidase mutants into proximity so that complementation occurs and active P-galactosidase is produced. The active β-galactosidase may be detected by methods well-known in the art); Van Ostade et al., J. Interf.

Cytok. Res. 20, 79–87 (2000) and WO 00/06722, WO 01/90188 (A bioassay for ligands that signal through receptor clustering, called MAPPIT. Specifically, the invention relates to a recombinant receptor, comprising an extracellular ligand-binding domain and a cytoplasmic domain that comprises a heterologous bait polypeptide, which receptor is activated by binding of a ligand to said ligand-binding domain and by binding of a prey polypeptide to said heterologous bait peptide. The invention also relates to a method to detect compound—compound binding using said recombinant receptor); WO 94/18317, WO 96/13613, WO 99/41258 (Schreiber, methods to induce a biological event by compound induced dimerization), and Ghosh et al., J. Am. Chem. Soc., 2000, 122: 5658–9 (reconstitution of fluorescence from a split green fluorescent protein).

Systems for studying protein—protein interactions in mammalian cells have also be described. For example, Fearon et al. (Karyoplasmic interaction selection strategy: A general strategy to detect protein—protein interactions in mammalian cells, Proc. Natl. Acad. Sci. USA 89: 7958–7962, 1992) describe a strategy and reagents for study of protein—protein interactions in mammalian cells, termed the karyoplasmic interaction selection strategy (KISS). With this strategy, specific protein—protein interactions are identified by reconstitution of the functional activity of the yeast transcriptional activator GAL4 and the resultant transcription of a GAL4-regulated reporter gene. Reconstitution of GAL4 function results from specific interaction between two fusion proteins: one contains the DNA-binding domain of GAL4; the other contains a transcriptional activation domain. Transcription of the reporter gene occurs if the two fusion proteins can form a complex that reconstitutes the DNA-binding and transcriptional activation functions of GAL4. Using the KISS system, Fearon et al. demonstrate specific interactions for sequences from three different pairs of proteins that complex in the cytoplasm. In addition, they demonstrate that reporter genes encoding cell surface or drug-resistance markers can be specifically activated as a result of protein—protein interactions. With these selectable markers, the KISS system can be used to screen specialized cDNA libraries to identify novel protein interactions.

A skilled artisan will be able to identify the suitable yeast two-hybrid system components for use with the instant invention without undue experimentation. These will include, but are not limited to expression vectors for reporter genes and their assay/detection methods, expression vectors for expression of fusion protein comprising DNA binding protein and P1/P2, and expression vectors for expression of fusion protein comprising transcription activation domain and P1/P2. In certain embodiments, P2 is from a polypeptide library or libraries, so the vector chosen for the expression of the P2 fusion shall be appropriate for library construction. A skilled artisan will be able to utilize any of the technologies/methods described above, or combination thereof, or modification thereof, to practice the instant invention. The contents of all these references are incorporated by reference herein.

(i.b) Reporter Genes

In a reporter system based on the transcriptional activation of a reporter gene, one has to choose a reporter gene appropriate for the host cell type and assay format envisaged. The host cell of choice needs to provide the appropriate transcriptional machinery, the choice of reporter gene will depend on the method chosen to detect and potentially quantify the transcription of the reporter gene, for example, by Western Blot, calorimetric or fluorimetric methods or a growth inhibition assay on selective or counterselective media, or a cell surface marker.

A wide range of reporter genes suitable for use in the methods of the present invention will be known to the skilled artisan, and he will be readily able to choose the appropriate reporter gene for a given assay format. Such reporter gene may be a positive selectable marker gene which can be selected for under appropriate conditions. In principle, any non-redundant gene in a synthetic pathway that is essential to the survival of the cell can be used for the construction of an auxotrophic positive selectable marker, but frequently used such makers include, without limitation, HIS3, LYS2, LEU2, TRP2, ADE2. Usually, a cell line is constructed that is deficient in the marker gene, and that can only grow on media supplemented with the corresponding metabolic product, i.e., histidine, lysine, leucine, tryptophan or adenine. When used for selection, a desirable phenotype, i.e., expression of a desired recombinant gene, is linked to the expression of the gene the cell is deficient in. Other positive selectable markers include antibiotic resistance markers, e.g., Hygromycin resistance (HygR), neomycin resistance (neo$^R$), puromycin resistance (PAC$^R$) or Blasticidin S resistance (BlaS$^R$), or any other antibiotic resistance marker. Here, expression of a desired recombinant gene is linked to the expression of the antibiotic resistance marker by transforming cells with gene constructs comprising both the desired recombinant gene and a recombinant form of the antibiotic resistance marker gene. Selection is then carried out on media containing the antibiotic, e.g., Hygromycin, neomycin, puromycin or Blasticidin S.

In addition, the reporter gene may encode a detectable protein that, upon transcriptional activation of said reporter gene, allows host cells to be visually differentiated from host cells in which said reporter gene has not been activated. Such a detectable protein is preferably encoded by at least one of the genes lacZ, gfp, yfp, bfp, cat, luxAB, HPRT or a cell surface marker gene. Other similar genes exist and the person skilled in the art will readily identify other such genes that can be employed according to this embodiment. WO 98/25947 describes a prokaryotic two-hybrid assay system, which also provides details about bacterial reporter genes that can be used with the instant invention. The contents of WO 98/25947 are incorporated by reference herein. Selectable markers for use in bacterial cells include antibiotic resistance markers, e.g., bla (beta-lactamase resistance gene), cam (chloramphenicol acetyl transferase gene) or kan (kanamycin phosphoryl transferase gene), luminescence markers such as gfp, color-inducing markers, for example lacZ, auxotrophic markers (any amino acid biosynthesis gene) and heavy metal resistance markers. Further selectable markers may be found in: *Escherichia coli* and *Salmonella: Cellular and molecular biology, Second edition*, F. C. Neidhardt, et al. (Edrs.), 1996. ASM Press, Washington, D.C., USA Furthermore, negative selectable reporter genes which can be used in a cell, and which can be selected against under appropriate conditions, may be employed. In preferred applications, the reporter is a selectable marker which is capable of both positive and negative selection. For example, the reporter gene may be chosen from the list of URA3, HIS3, LYS2, HygTk, Tkneo, TKBSD, PACTk, HygCoda, Codaneo, CodaBSD, PACCoda, Tk, codA, and GPT2. The reporter moiety may also be TRP1, CYH2, CAN1, HPRT.

A preferred example of a negative selectable marker gene for use in yeast is the URA3 gene which can be both selected for (positive selection) by growing ura3 auxotrophic yeast strains in the absence of uracil, and selected against (negatively selection) by growing cells on media containing 5-fluoroorotic acid (5-FOA) (Boeke, et al., 1987, Methods Enzymol 154: 164–75). The concentration of 5-FOA can be optimized by titration so as to maximally select for cells in which the URA3 reporter is inactivated by proteolytic degradation to some preferred extent. For example, relatively high concentrations of 5-FOA can be used which allow only cells expressing very low steady-state levels of URA3 reporter to survive. In contrast, lower concentrations of 5-FOA can be used to select for binding partners with relatively weak affinities for one another. In addition, proline can be used in the media as a nitrogen source to make the cells hypersensitive to the toxic affects of the 5-FOA (McCusker & Davis (1991) Yeast 7: 607–8). Accordingly, proline concentrations, as well as 5-FOA concentrations can be titrated so as to obtain an optimal selection for URA3 reporter-deficient cells. Therefore the use of URA3 as a negative selectable marker allows a broad range of selective stringencies which can be adapted to minimize false positive background noise and/or to optimize selection for high affinity binding interactions. Other negative selectable markers which can be adapted to the methods of the invention are included within the scope of the invention.

Another example of a negative selectable marker gene for use in yeast is the TRP1 gene which can be both selected for (positive selection) by growing trp1 auxotrophic yeast strains in the absence of tryptophan, and selected against (negative selection) by growing cells on media containing 5-fluoroanthranilic acid (5-FAA) (Toyn et al., 2000, Yeast, 16: 553–560).

Two other negative selectable marker genes for use in yeast are CYH2 and CAN1 both of which can be selected against (negative selection) by growing cells on media containing cycloheximide or canavanine (*The Yeast Two-Hybrid System (Advances in Molecular Biology)*, Ed. Paul L. Bartel and Stanley Fields, Oxford University Press, 1997). Counter-selectable markers for use in bacteria include sacB (*B. subtilis* gene encoding levansucrase that converts sucrose to levans, which is harmful to the bacteria), rpsL (strA) (encodes the ribosomal subunit protein (S12) target of streptomycin), tetA$^R$ (confers resistance to tetracycline but sensitivity to lipophilic compounds, e.g., fusaric and quinalic acids), phe$^S$ (encodes the subunits of Phe-tRNA synthetase, which renders bacteria sensitive to p-chlorophenylalanine, a phenylalanine analog), thyA Encodes thymidilate synthetase, which confers sensitivity to trimethoprim and related compounds, lacY (encodes lactose permease, which renders bacteria sensitive to o-nitrophenyl-D-galactopyranoside), gata-1 (encodes a zinc finger DNA-binding protein which inhibits the initiation of bacterial replication), ccdB (encodes a cell-killing protein which is a potent poison of bacterial gyrase). Further counter-selectable markers may be found in: *Escherichia coli and Salmonella: Cellular and molecular biology, Second edition*, F. C. Neidhardt, et al. (Edrs.), 1996, ASM Press, Washington, D.C., USA Numerous selectable markers which operate in mammalian cells are known in the art and can be adapted to the method of the invention so as to allow direct negative selection of interacting proteins in mammalian cells. Examples of mammalian negative selectable markers include Thymidine kinase (Tk) (Wigler et al., 1977, Cell 11: 223–32; Borrelli et al., 1988, Proc. Natl. Acad. Sci. USA 85: 7572–76) of the Herpes Simplex virus, the human gene for hypoxanthine phosphoriboxyl transferase (HPRT) (Lester et al., 1980, Somatic Cell Genet. 6: 241–59; Albertini et al., 1985, Nature 316: 369–71) and Cytidine deaminase (codA) from *E. coli* (Mullen et al., 1992, Proc. Natl. Acad. Sci. USA 89: 33–37; Wei and Huber, 1996, J. Biol. Chem. 271: 3812–16). For example: the Tk gene can be selected against using Gancyclovir (GANC) (e.g., using a 1 µM concentration) and codA gene can be selected against using 5-Fluorocytidine (5-FIC) (e.g., using a 0.1–1.0 mg/ml concentration). In addition, certain chimeric selectable markers have been reported (Karreman, 1998, Gene 218: 57–61) in which a functional mammalian negative selectable marker is fused to a functional mammalian positive selectable marker such as Hygromycin resistance (Hyg$^R$, neomycin resistance (neo$^R$), puromycin resistance (PAC$^R$) or Blasticidin S resistance (BlaS$^R$). These produce various Tk-based positive/negative selectable markers for mammalian cells such as HygTk, Tkneo, TKBSD, and PACTk, as well as various codA-based positive/negative selectable markers for mammalian cells such as HygCoda, Codaneo, CodaBSD, and PACCoda. Tk-neo reporters which incorporate luciferase, green fluorescent protein and/or beta-galactosidase have also been recently reported (StratMtxee et al., 2000, BioTechniques 28: 210–14). These vectors have the advantage of allowing ready screening of the "positive" marker/reporter by fluorescent and/or immunofluorescent microscopy. The use of such positive/negative selectable markers affords the advantages mentioned above for URA3 as a reporter in yeast, inasmuch as they allow mammalian cells to be assessed by both positive and negative selection methods for the expression and relative steady-state level of the reporter fusion. For example, Rojo-Niersbach et al reported the use of GPT2 (Guanine Phosphoryl Transferase 2) in mammalian cells as a basis for the selection of protein interactions (Biochem. J. 348: 585–590, 2000).

The above listing of genes suitable for use as reporter genes in the methods of the present invention is not meant to be exhaustive nor limiting. The skilled artisan may know other or become aware of newly discovered or developed systems suitable for use as reporter genes in the methods of the present invention. The scope of the present invention is meant to include their use.

(ii) Hybrid Small Molecules

The preferred hybrid molecules of the present invention are represented by the structure shown in Formula I:

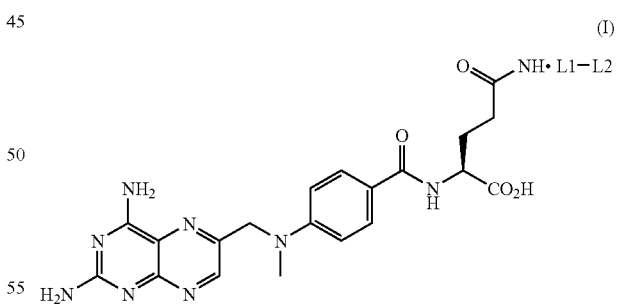

(I)

wherein, L1 and L2 are as defined above.

In order to pass cell membranes, a certain lipophilicity is desirable. However, in order to get to the membrane, such compound first has to cross an aqueous compartment by diffusion. If its water solubility is too low, too little compound can reach the membrane and exert its effect inside the cell. Accordingly, the present invention contemplates using various combinations of hydrophilic and hydrophobic groups for L1 to optimize the molecule's aqueous and cell membrane solubilities.

(ii.a) Linker Sequences

In certain embodiments, any chemical linker L1 (including synthetic polypeptides, see below) can be used to link MTX to L2, provided that the presence of the linker sequence will not significantly interfere with the reporter system when P1 binds to MTX and P2 binds to L2. In addition, the presence of the linker should not overly adversely affect the affinities between P1 and R1 or between P2 and L2.

As such, in order to confirm the suitability of a given hybrid ligand as a dimerizing compound of general structure MTX-L1-L2 for the uses proposed herein, it may be helpful to characterize the binding properties of such hybrid ligand to its binding partners P1 and P2, in as far as these are known, and to possibly compare these binding characteristics with those of the unlinked compounds MTX and L2, respectively.

Preferably, the hybrid ligand should exhibit binding properties similar to the binding properties of the unlinked compounds. However, the molecular weight increase brought about by the linking, as well as steric and electronic effects caused by the attachment of the linker to a functional group of the unlinked compounds may alter the binding characteristics. Therefore, while not being essential, it is preferable to perform such characterization on a newly synthesized hybrid ligand. This, however, should not be interpreted as limiting the scope of the invention.

The affinity of hybrid ligands to their corresponding binding partners may be determined, for example, using a BIACORE™ assay system (Biacore AB, Uppsala, SE). Other systems yielding a qualitatively similar result, for example, those developed by Affinity Sensors (Cambridge, UK), will be readily apparent to those skilled in the art.

Furthermore, other interaction methodologies that measure the binding affinities between a hybrid ligand and its binding proteins may be employed.

Linker moieties (L1) need not contain essential elements for binding to the P1 and/or P2 proteins, and for certain embodiments of the present invention may be selected from a very broad range of structural types. Preferred moieties include $C_2$–$C_{20}$ alkyl, aryl, or dialkylaryl structures where alkyl and 2,5-aryl are defined as above. Linker moieties may be conveniently joined to monomers R1 and R2 through functional groups such as ethers, amides, ureas, carbamates, and esters; or through alkyl—alkyl, alkyl-aryl, or aryl—aryl carbon—carbon bonds. Furthermore, linker moieties may be optimized (e.g., by modification of chain length and/or substituents) to enhance pharmacokinetic properties of the multimerizing agent. Holt et al. (WO 96/06097) and Kathryn et al. (J. Steroid Biochem. Molec. Biol., 49: 139–152) describe a number of linker moieties that can be used to construct the hybrid ligands of the instant invention (MTX-L1-L2), the contents of these references are incorporated by reference herein.

In other embodiments, linker sequences are specifically designed so that increased solubility and enhanced permeability results. This is important since the components of the hybrid molecule, MTX and L2, are organic molecules with potentially low water solubility. By linking two small molecules, the molecular weight is obviously increased, potentially further decreasing the water solubility and diffusion coefficient. By designing a linker that increases solubility and enhances permeability of the hybrid, the available MTX-L1-L2 hybrid in solution and ultimately inside the cell is effectively increased, so that significantly higher sensitivity of the whole system can be achieved. In one embodiment, from 2 to 25 repeats of polyethyleneglycol (PEG) groups of the general formula $CH_2WCH_2$ can be used, wherein W represents O, S, SO, or $SO_2$. The number of repeats is preferably in the range of 3–25, 5–25, 9–25, 2–15, 3–15, 5–15 or 9–15, and more specifically is preferably 25, 20, 15, 10, 9, 8, 7, 6, 5, 4, or 2. In a most preferred embodiment, three polyethyleneglycol groups are used as linker thereby offering significantly better solubility and membrane permeability. In other cases where an even more strongly increased solubility and/or membrane permeability is desired, five repeats may be used. Furthermore, it should be understood that modifications of the side-chains of the linker can be easily achieved without adversely affecting the solubility, membrane permeability, and/or overall biological activity of the compound, and therefore, such derivative linker sequence units are also within the scope of the invention.

Below are presented several examples for hybrid molecules as envisaged by the present invention. $(CH_2WCH_2)_p$-groups, wherein W represents O or S, p=3 or 5, were employed for these examples, without limitation. Increasing the length of the linker sequence appears to increase the effectiveness of the compound in at least some three-hybrid assays, which is most likely due to the increased solubility or membrane permeability or flexibility of the molecule, or a combination thereof. For example, the n-octanol-water partition coefficient (clogP) of the compound Mtx-mdbt-Dex is predicted by structure based calculations using the program Kowwin (Syracuse Research Corporation) to be 3.62, and it's water solubility to lie in the range of 0.00035 mg/l, while clogP for Compound #1 identical with Licitra et al.'s Mtx-mdbt-Dex except for the replaced linker, is estimated by the same method to be −1.71, and its solubility as 0.13 mg/l, corresponding to a factor of approximately 300 in increased solubility. Structure of Compound #1 (MTX=Methotrexate, L1=$(CH_2$—$CH_2$—$O)_5$, L2 is an active CDK-inhibitor)

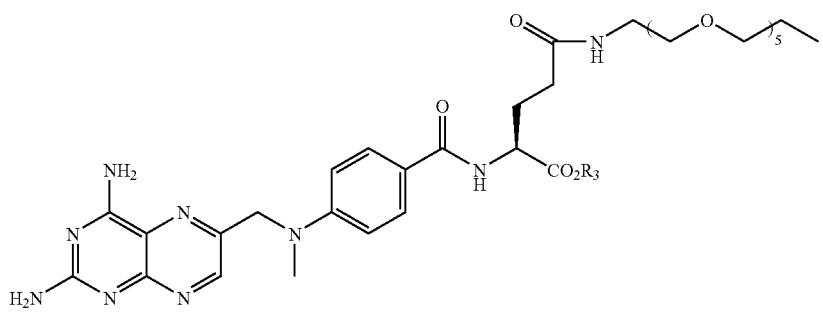

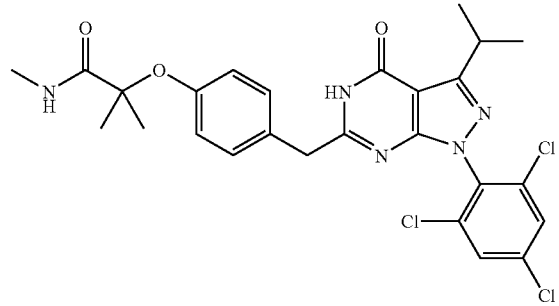

2-[(4-{[(2,4-diaminopteridin-6-yl)methyl]methylamino}phenyl)carbonylamino]-4-(2-{2-[2-(2-{2-[2-(4-{[3-isopropyl-4-oxo-1-(2,4,6-trichlorophenyl)-(4,5-dhydro-1H-pyrazolo[3,4-d]pyrimidin-6-ylmethyl]-phenoxy)-2-methyl-propanoylamino)-ethoxy]-ethoxy}-ethoxy)-ethoxy]-ethoxy}-ethylcarbamoyl)-butyric acid Structure of STI-571 probe molecule

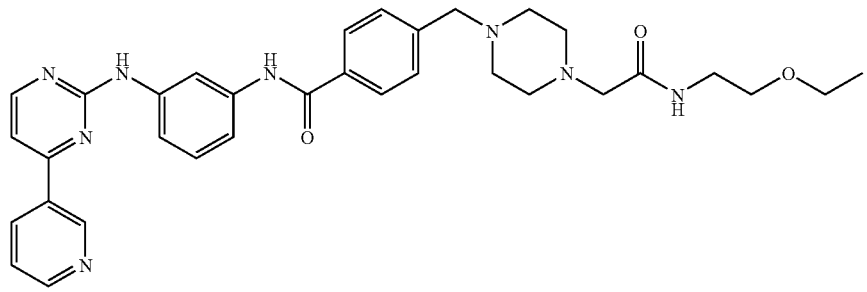

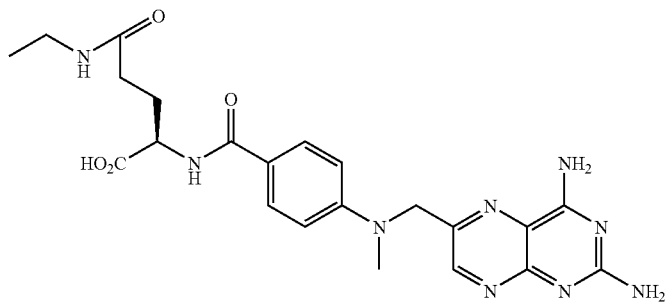

2-[(4-{[(2,4-diaminopteridin-6-yl)methyl]methylamino}phenyl)carbonylamino]-4-(2-{2-[2-(2-{2-[2-(4-{4-[3-(4-pyridin-3-yl-pyrimidin-2-ylamino)-phenylcarbamoyl]-benzyl}-piperazinyl-1-yl)-acetylamino)-ethoxy]-ethoxy}-ethoxy)-ethoxy]-ethoxy}-ethylcarbamoyl)-butyric acid (ii.b) High Affinity Ligands/Ligands and Binding Proteins According to the invention, two pairs of polypeptide/small chemical compound interactions have to be present for the three-hybrid system to activate a reporter system. One pair of interaction is between a known ligand and its known polypeptide binding partner. This essentially serves as an "adaptor" to create a L2::P2 interaction interface, and to provide the necessary second element of the reporter system, RS2. Therefore, the stronger the P1::MTX interaction, the better the overall performance of the system. There are at least two categories of P1::MTX interactions available for this purpose: covalent and non-covalent interactions. Covalent interactions are almost always stronger. For example, certain enzymes and their suicide inhibitors or suicide substrates can be exploited to constitute such covalent interaction pairs. Suicide inhibitors or suicide substrates bind to their prospective enzymes with high specificity and affinity. Once bound, a chemical reaction occurs, physically linking the inhibitor/substrate to the enzyme, usually at its active site, thereby irreversibly inactivates the enzyme. If such an enzyme is used as P1 and its suicide inhibitor/substrate used as MTX in the three-hybrid system, a covalent link between P1-MTX can be established. For example, beta-lactamase may covalently bind suicide inhibitors such as beta-lactam antibiotics. However, there are only limited selections of these enzyme—substrate/inhibitor pairs particularly when the substrate/inhibitor needs to be connected to another small compound L2 via a linker yet still retains solubility and membrane permeability in vivo. On the other hand, non-covalent P1::R1 interactions are more versatile. There are many known high affinity ligand-receptor interactions that can be employed in the three-hybrid system. For example, FK506 and FKBP (FK506 Binding Protein), FK506 and Rapamycin, biotin and streptavidin, DHFR and methotroxate (Mtx), glucocorticoid receptor and Dexamethasone (Dex), etc, represent binding pairs with affinities high enough to be potentially suitable as ligand receptor binding pairs. The DHFR-Mtx interaction offers pM affinity, and therefore is much better than FK506-FKBP interaction.

Any of a number of ligand/ligand binding protein pairs known in the art may be utilized. For example, the steroid molecule, dexamethasone, which binds the glucocorticoid receptor with high affinity may be employed. Dexamethasone is modular in nature; it can be covalently linked to another small molecule such as biotin without losing its affinity for the glucocorticoid receptor. The use of steroids such as dexamethasone is advantageous in that these molecules are highly membrane permeable and are small in size. The method of the invention may utilize other steroid molecules as well as small molecules other than steroids as ligand MTX. Other ligands such as cyclosporin (M.W. 1200) may also be used where the target or receptor to which the ligand is bound has been identified in the art. As another example, the small molecule FK506 (M.W. 850) which binds an FK binding protein (FKBP), and modified derivatives of FK506 (i.e., "bump" modified compounds) which bind to modified FK binding proteins (i.e., FKBP mutants which compensate for such "bump" modifications) are also adaptable for use as ligand/ligand-binding proteins of the invention (see e.g., U.S. Pat. No. 6,054,436, the contents of which are incorporated herein by reference).

Table 1 provides a list of ligands and ligand-binding pairs which are known in the art and adaptable to the compositions and methods of the invention. Particularly preferred ligand/ligand-binding protein pairs have strong binding affinities as reflected in low dissociation constants (e.g., methotrexate/DHFR at 52 pM; or dexamethasone/glucocorticoid receptor at 86 nM).

TABLE 1

List of Some High Affinity Ligand/Ligand Binding Proteins

| Ligand | Molecular weight (D) | Ligand Binding Protein | Affinity |
|---|---|---|---|
| Biotin | (244) | Avidin | 80 fM |
| Ni | (59) | 6 X His | 0.8 μM |
| Rapamycin | (914) | FKB12 | 12 μM |
| FK506 | (804) | FKB12 | 12 μM |
| Methotrexate | (454) | DHFR | 52 pM |
| Tetracyclin | (444) | Tet-R | 24 nM |
| Dexamathasone | (392) | Glucocorticoid receptor | 86 nM |
| Glutathione | (307) | Glutathione-S-Transferase | 24 μM |
| Maltose | (342) | Maltose Binding Protein | 40 nM |
| Novobiotin | (612) | GyrB | 123 μM |

In general, virtually any ligand/ligand-binding protein pair with sufficient affinity may be adapted to the compositions and methods of the invention. Particularly preferred embodiments utilize ligand-binding proteins which are known to function efficiently intracellularly. For example, steroid receptors occur intracellularly and bind with high affinities to their cognate steroid hormones under intracellular physiological conditions. Examples of such steroid receptors include the human estrogen receptor (e.g., GenBank Accession No. NM_000125), which is found in estrogen-sensitive animal cells, and human glucocorticoid receptor protein (e.g., GenBank Accession No. NM_004491), which is found in cells responsive to glucocorticoid hormones. Other steroids with suitable receptors for use in the invention include testosterone, progesterone, and cortisone.

It should be understood that the above mentioned ligands shall also include those derivatives and equivalents that share close structural relationship to those ligands. To illustrate, Mtx only uses its 2,4-diaminopteridine double-ring structure to bind DHFR. Therefore, 2,4-diaminopteridine shall be considered a derivative of Mtx that is also within the scope of the invention. A "derivative" generally shares the effective moiety with the original compound but may also have other non-essential structural elements for a given activity.

Still other preferred ligands for use in the invention are known in the art and may be adapted to the methods and compositions of the invention by skilled artisan without undue experimentation. For example, other preferred ligands which could be adapted to the invention include fat-soluble vitamins with cognate receptors such as Vitamin D and its various forms such as $D_1$, $D_2$ (9,10-secoergosta-5,7,10(19),22-tetraen-3-ol), $D_3$ (9,10 secocholeta-5,7,10 (19)-trien-3-ol) and $D_4$ (9,10-secoergosta-5,7,10(19)-trien-3-ol). Vitamin $D_3$ binds with affinity to the human nuclear vitamin D receptor protein (e.g., GenBank Accession No. NM_000376; see also Haussler et al. (1995) Bone 17: 33S–38S) and this ligand/ligand-binding protein pair may be adapted to the invention. Still other ligands with cognate ligand-binding proteins that may be adapted to the invention include thyroid hormone and retinoic acid. DeWolf and Brett ((2000) Pharmacol Rev. 52: 207–36) provides a summary of many useful ligand-binding proteins with cognate ligands including: biotin-binding proteins, lipid-binding protein, periplasmic binding proteins, lectins, serum albumins, immunoglobulins, various inactivated enzymes, insect pheromone binding proteins, odorant-binding proteins, immunosuppressant-binding proteins, phosphate- and sulfate-binding protein.

In addition, steroid, retinoic acid, beta-lactam antibiotic, cannabinoid, nucleic acid, polypeptide, FK506, FK506 derivatives, rapamycin, tetracycline, methotrexate, 2,4-diaminopteridine, novobiocin, maltose, glutathione, biotin, vitamin D, dexamethasone, estrogen, progesterone, cortisone, testosterone, cyclosporin and their natural or synthesized binding partners are all possible for use in the instant invention as a component of the above described high affinity ligand/ligand binding pair. In all those compounds mentioned above, it should be understood that basically equivalent compounds with only minor structural variations can also be used.

Other compounds may also be used with the present invention. For example, any of the compounds disclosed in U.S. patent application Ser. No. 10/321,284, filed Dec. 17, 2002, PCT application PCT/US02/21449, filed Jul. 6, 2002, and/or PCT application PCT/US02/21553, filed Jul. 10, 2002 may be used with the present invention. Additional suitable compounds are also shown in Table 2, attached herewith and incorporated herein.

On the other hand, a predetermined second ligand is linked to the above-described ligand to form a compound ligand. At least the following chemical groups and those basically equivalent compounds with only minor structural variations can be used as such predetermined ligands: a peptide, a nucleic acid, a carbohydrate, a polysaccharide, a lipid, a prostaglandin, an acyl halide, an alcohol, an aldehyde, an alkane, an alkene, an alkyne, an alkyl, an alkyl halide, an alkaloid, an amine, an aromatic hydrocarbon, a sulfonate ester, a carboxylate acid, an aryl halide, an ester, a phenol, an ether, a nitrile, a carboxylic acid anhydride, an amide, a quaternary ammonium salt, an imine, an enamine, an amine oxide, a cyanohydrin, an organocadmium, an aldol, an organometallic, an aromatic hydrocarbon, a nucleoside, a nucleotide. For example, in a recent publication (U.S. Pat. No. 6,326,155), a method is described that aids in selecting a ligand for a given target molecule.

(iii) Libraries and Screening Methods (iii.a) Variegated Peptide Display

One aspect of the invention provides a method to identify polypeptides that bind to a given small molecule/chemical compound. The polypeptides are usually provided in the form of a variegated library, which can contain different number of members, preferably from 2 to 10 members, or 10 to 500 members, 500 to 10,000 members or more than 10,000 members. The library can be a nucleic acid library (mRNA, cDNA, genomic DNA, EST, YAC, p1 clones, BAC/PAC libraries, etc.) which encodes polypeptides. Depending on the specific embodiments of the screens used, the nucleic acid library is usually constructed in vectors suitable for the chosen embodiment, using art-recognized techniques.

The variegated peptide libraries of the subject method can be generated by any of a number of methods, and, preferably, exploit recent trends in the preparation of chemical libraries. The library can be prepared, for example, by either synthetic or biosynthetic approaches. As used herein, "variegated" refers to the fact that a population of peptides is characterized by having a peptide sequence which differ from one member of the library to the next. For example, in a given peptide library of N amino acids in length, the total number of different peptide sequences in the library is given by the product of $(X_1 * X_2 * \ldots X_i)$, where each $X_i$ represents the number of different amino acid residues occurring at position X of the peptide. In a preferred embodiment of the present invention, the peptide display collectively produces a peptide library including at least 96 to $10^7$ different peptides, so that diverse peptides may be simultaneously assayed for the ability to interact with the small molecule/chemical compound.

The polypeptide libraries can be prescreened for interactions with the small molecule/chemical compound, for example using a phage display method. Peptide libraries are systems which simultaneously display, in a form which permits interaction with a target molecule, a highly diverse and numerous collection of peptides. These peptides may be presented in solution (Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. 5,223,409), plasmids (Cull et al. (1992) Proc Natl Acad Sci USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; Felici (1991) J. Mol. Biol. 222:301–310; and Ladner U.S. Pat. No. 5,223,409).

In one embodiment, the peptide library is derived to express a combinatorial library of peptides which are not based on any known sequence, nor derived from cDNA. That is, the sequences of the library are largely random. It will be evident that the peptides of the library may range in size from dipeptides to large proteins.

In another embodiment, the peptide library is derived to express a combinatorial library of peptides which are based at least in part on a known polypeptide sequence or a portion thereof (not a cDNA library). That is, the sequences of the library are semi-random, being derived by combinatorial mutagenesis of a known sequence(s). See, for example, Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461. Accordingly, polypeptide(s) which are known ligands for a target molecule can be mutagenized by standard techniques to derive a variegated library of polypeptide sequences which can further be screened for binding partners including agonists and/or antagonists.

In still another embodiment, the combinatorial polypeptides are produced from a cDNA library, a genomic DNA library. The source of DNA can be of human, non-human mammalian, fish, amphibian, insect, worm, yeast, plant, or bacteria.

Depending on size, the combinatorial peptides of the library can be generated as is, or can be incorporated into larger fusion proteins, such as library-reporter system fusions. The fusion protein may also provide, for example, stability against degradation or denaturation, as well as a secretion signal if secreted, or the reporter function necessary for screens. In an exemplary embodiment, the polypeptide library is provided as part of thioredoxin fusion proteins (see, for example, U.S. Pat. Nos. 5,270,181 and 5,292,646; and PCT publication WO94/02502). The combinatorial peptide can be attached on the terminus of the thioredoxin protein, or, for short peptide libraries, inserted into the so-called active loop. In another preferred embodiment, the fusion protein library can be provided as a fusion to either the DNA binding domain or the transcription activation domain of the transcription based yeast three-hybrid system.

In preferred embodiments, the combinatorial polypeptides are in the range of 3–1000 amino acids in length, more preferably at least 5–500, and even more preferably at least 3–100, 5–50, 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

Regardless of the nature of the peptide libraries, the same peptide libraries can also be provided as nucleic acid libraries encoding such peptide libraries. These nucleic acid libraries can be provided in suitable vectors for expression in various systems, including, but are not limited to mammalian, insect, yeast and bacteria expression systems. A skilled artisan shall be able to determine the appropriate vectors to use for various expression systems.

(iii.b) Biosynthetic Peptide Libraries

The harnessing of biological systems for the generation of peptide diversity is now a well established technique which can be exploited to generate the peptide libraries of the subject method. The source of diversity is the combinatorial chemical synthesis of mixtures of oligonucleotides. Oligonucleotide synthesis is a well-characterized chemistry that allows tight control of the composition of the mixtures created. Degenerate DNA sequences produced are subsequently placed into an appropriate genetic context for expression as peptides.

There are two principal ways in which to prepare the required degenerate mixture. In one method, the DNAs are synthesized a base at a time. When variation is desired at a base position dictated by the genetic code a suitable mixture of nucleotides is reacted with the nascent DNA, rather than the pure nucleotide reagent of conventional polynucleotide synthesis. The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the cell.

Whatever the method may be for generating diversity at the codon level, chemical synthesis of a degenerate gene sequence can be carried out in an automatic DNA synthesizer, and the synthetic genes can then be ligated into an appropriate gene or vector for expression. The purpose of a degenerate set of genes is to provide, in one mixture, all of the sequences encoding the desired set of potential test peptide sequences. The synthesis of degenerate oligonucleotides is well known in the art (see for example, Narang, S A (1983) Tetrahedron 39:3; Itakura et al. (1981) Recombinant DNA, Proc $3^{rd}$ Cleveland Sympos. Macromolecules, ed. A G Walton, Amsterdam: Elsevier pp 273–289; Itakura et al. (1984) Annu. Rev. Biochem. 53:323; Itakura et al. (1984) Science 198: 1056; Ike et al. (1983) Nucleic Acid Res. 11:477. Such techniques have been employed in the directed evolution of other proteins (See, for example, Scott et al. (1990) Science 249: 386–390; Roberts et al. (1992) PNAS 89: 2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Because the number of different peptides one can create by this combination approach can be huge, and because the expectation is that peptides with the appropriate structural characteristics to serve as ligands for a given target protein will be rare in the total population of the library, the need for methods capable of conveniently screening large numbers of clones is apparent. Several strategies for selecting peptide ligands from the library have been described in the art and are applicable to certain embodiments of the present method.

The number of possible peptides for a given library may, in certain instances, exceed $10^{12}$. To sample as many combinations as possible depends, in part, on the ability to recover large numbers of transformants. For phage with plasmid-like forms (as filamentous phage), electrotransformation provides an efficiency comparable to that of phage-transfection with in vitro packaging, in addition to a very high capacity for DNA input. This allows large amounts of vector DNA to be used to obtain very large numbers of transformants. The method described by Dower et al. (1988) Nucleic Acids Res., 16:6127–6145, for example, may be used to transform fd-tet derived recombinants at the rate of about $10^7$ transformants/μg of ligated vector into E. coli (such as strain MC1061), and libraries may be constructed in fd-tet B1 of up to about $3 \times 10^8$ members or more. Increasing DNA input and making modifications to the cloning protocol within the ability of the skilled artisan may produce increases of greater than about 10-fold in the recovery of transformants, providing libraries of up to $10^{10}$ or more recombinants.

(iii.c) Synthetic Peptide Libraries

In contrast to the recombinant methods, in vitro chemical synthesis provides a method for generating libraries of compounds, without the use of living organisms, that can be screened for ability to bind to a target molecule. Although in vitro methods have been used for quite some time in the pharmaceutical industry to identify potential drugs, recently developed methods have focused on rapidly and efficiently generating and screening large numbers of compounds and are particularly amenable to generating peptide libraries for use in the subject method.

One particularly useful features of the synthetic peptide library is that it can be used to supply libraries of L2 to be coupled to MTX-L1, in order to make the hybrid ligand. This can be used to screen for a synthetic polypeptide that can bind a predetermined polypeptide. For example, the synthetic polypeptide can be a potential peptide inhibitor of a predetermined enzyme or transcription factor, etc. Such screens can be a prescreen of large number of random polypeptides in an in vitro high-throughput setting, so that primary positive peptides can be selected, and its variants encoded by a nucleic acid library further screened in an in vivo embodiment.

Another use for the synthetic peptide library is to generate libraries of short peptide linkers to be inserted between MTX and L2 ligands. This is particularly useful since an optimal linker sequence may be generated for a particular MTX-L2 pair, so that the final hybrid ligand may possess the optimal chemical and/or structural characteristics such as solubility, membrane permeability, etc.

Both uses require coupling of a synthetic polypeptide, using knowledge well-known in the art (such as the ones described below or elsewhere), to another molecule (linker L1 or ligands MTX and L2), which may be peptide or non-peptide in nature. The various approaches to simultaneous preparation and analysis of large numbers of synthetic peptides (herein "multiple peptide synthesis" or "MPS") each rely on the fundamental concept of synthesis on a solid support introduced by Merrifield in 1963 (Merrifield, R. B. (1963) J Am Chem Soc 85:2149–2154; and references cited in section I above). Generally, these techniques are not dependent on the protecting group or activation chemistry employed, although most workers today avoid Merrifield's original tBoc/Bzl strategy in favor of the more mild Fmoc/tBu chemistry and efficient hydroxybenzotriazole-based coupling agents. Many types of solid matrices have been successfully used in MPS, and yields of individual peptides synthesized vary widely with the technique adopted (e.g., nanomoles to millimoles).

(iii.c.1) Multipin Synthesis

One form that the peptide library of the subject method can take is the multipin library format. Briefly, Geysen and co-workers (Geysen et al. (1984) PNAS 81:3998–4002) introduced a method for generating peptide by a parallel synthesis on polyacrylic acid-grated polyethylene pins arrayed in the microtitre plate format. In the original experiments, about 50 nmol of a single peptide sequence was covalently linked to the spherical head of each pin, and interactions of each peptide with receptor or antibody could be determined in a direct binding assay. The Geysen technique can be used to synthesize and screen thousands of peptides per week using the multipin method, and the tethered peptides may be reused in many assays. In subsequent work, the level of peptide loading on individual pins has been increased to as much as 2 μmol/pin by grafting greater amounts of functionalized acrylate derivatives to detachable pin heads, and the size of the peptide library has been increased (Valerio et al. (1993) Int. J. Pept. Protein Res. 42:1–9). Appropriate linker moieties have also been appended to the pins so that the peptides may be cleaved from the supports after synthesis for assessment of purity and evaluation in competition binding or functional bioassays (Bray et al. (1990) Tetrahedron Lett. 31:5811–5814; Valerio et al. (1991) Anal. Biochem. 197:168–177; Bray et al. (1991) Tetrahedron Lett. 32:6163–6166).

More recent applications of the multipin method of MPS have taken advantage of the cleavable linker strategy to prepare soluble peptides (Maeji et al. (1990) J. Immunol. Methods 134:23–33; Gammon et al. (1991) J Exp Med 173:609–617; Mutch et al. (1991) Pept Res 4:132–137).

(iii.c.2) Divide-Couple-Recombine

In yet another embodiment, a variegated library of peptides can provide on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into as many separate groups to correspond to the number of different amino acid residues to be added that position, the different residues coupled in separate reactions, and the beads recombined into one pool for the next step.

In one embodiment, the divide-couple-recombine strategy can be carried out using the so-called "tea bag" MPS method first developed by Houghten, peptide synthesis occurs on resin that is sealed inside porous polypropylene bags (Houghten et al. (1986) PNAS 82:5131–5135). Amino acids are coupled to the resins by placing the bags in solutions of the appropriate individual activated monomers, while all common steps such as resin washing and amino group deprotection are performed simultaneously in one reaction vessel. At the end of the synthesis, each bag contains a single peptide sequence, and the peptides may be liberated from the resins using a multiple cleavage apparatus (Houghten et al. (1986) Int J Pept Protein Res 27:673–678). This technique offers advantages of considerable synthetic flexibility and has been partially automated (Beck-Sickinger et al. (1991) Pept Res 4:88–94). Moreover, soluble peptides of greater than 15 amino acids in length can be produced in sufficient quantities (>0.5 mmol) for purification and complete characterization if desired.

Multiple peptide synthesis using the tea-bag approach is useful for the production of a peptide library, albeit of limited size, for screening the present method, as is illustrated by its use in a range of molecular recognition problems including antibody epitope analysis (Houghten et al. (1986) PNAS 82:5131–5135), peptide hormone structure-function studies (Beck-Sickinger et al. (1990) Int J Pept Protein Res 36:522–530; Beck-Sickinger et al. (1990) Eur J Biochem 194:449–456), and protein conformational mapping (Zimmerman et al. (1991) Eur J Biochem 200:519–528).

An exemplary synthesis of a set of mixed peptides having equimolar amounts of the twenty natural amino acid residues is as follows. Aliquots of 5 g (4.65 mmols) of p-methylbenzhydrylamine hydrochloride resin (MBHA) are placed into twenty porous polypropylene bags. These bags are placed into a common container and washed with 1.0 liter of $CH_2Cl_2$ three times (three minutes each time), then again washed three times (three minutes each time) with 1.0 liter of 5 percent $DIEA/CH_2Cl_2$ (DIEA=diisopropylethylamine; $CH_2Cl_2$=DCM). The bags are then rinsed with DCM and placed into separate reaction vessels each containing 50 ml (0.56 M) of the respective t-BOC-amino acid/DCM. N,N-Diisopropylcarbodiimide (DIPCDI; 25 ml; 1.12 M) is added to each container, as a coupling agent. Twenty amino acid derivatives are separately coupled to the resin in 50/50 (v/v) DMF/DCM. After one hour of vigorous shaking, Gisen's picric acid test (Gisen (1972) Anal. Chem. Acta 58:248–249) is performed to determine the completeness of the coupling reaction. On confirming completeness of reaction, all of the resin packets are then washed with 1.5 liters of DMF and washed two more times with 1.5 liters of $CH_2Cl_2$. After rinsing, the resins are removed from their separate packets and admixed together to form a pool in a common bag. The resulting resin mixture is then dried and weighed, divided again into 20 equal portions (aliquots), and placed into 20 further polypropylene bags (enclosed).

In a common reaction vessel the following steps are carried out: (1) deprotection is carried out on the enclosed aliquots for thirty minutes with 1.5 liters of 55% TFA/DCM; and 2) neutralization is carried out with three washes of 1.5 liters each of 5% DIEA/DCM. Each bag is placed in a separate solution of activated t-BOC-amino acid derivative and the coupling reaction carried out to completion as before. All coupling reactions are monitored using the above quantitative picric acid assay.

Next, the bags are opened and the resulting t-BOC-protected dipeptide resins are mixed together to form a pool, aliquots are made from the pool, the aliquots are enclosed, deprotected and further reactions are carried out. This process can be repeated any number of times yielding at each step an equimolar representation of the desired number of amino acid residues in the peptide chain. The principal process steps are conveniently referred to as a divide-couple-recombine synthesis.

After a desired number of such couplings and mixtures are carried out, the polypropylene bags are kept separated to here provide the twenty sets having the amino-terminal residue as the single, predetermined residue, with, for example, positions 2–4 being occupied by equimolar amounts of the twenty residues. To prepare sets having the single, predetermined amino acid residue at other than the amino-terminus, the contents of the bags are not mixed after adding a residue at the desired, predetermined position. Rather, the contents of each of the twenty bags are separated into 20 aliquots, deprotected and then separately reacted with the twenty amino acid derivatives. The contents of each set of twenty bags thus produced are thereafter mixed and treated as before-described until the desired oligopeptide length is achieved.

(iii.c.3) Multiple Peptide Synthesis Through Coupling of Amino Acid Mixtures

Simultaneous coupling of mixtures of activated amino acids to a single resin support has been used as a multiple peptide synthesis strategy on several occasions (Geysen et al. (1986) Mol: Immunol. 23:709–715; Tjoeng et al. (1990) Int. J. Pept. Protein Res. 35: 141–146; Rutter et al. (1991) U.S. Pat. No. 5,010,175; Birkett et al. (1991) Anal Biochem 196:137–143; Petithory et al. (1991) PNAS 88:11510–11514) and can have applications in the subject method. For example, four to seven analogs of the magainin 2 and angiotensinogen peptides were successfully synthesized and resolved in one HPLC purification after coupling a mixture of amino acids at a single position in each sequence (Tjoeng et al. (1990) Int. J. Pept. Protein Res. 35: 141–146). This approach has also been used to prepare degenerate peptide mixtures for defining the substrate specificity of endoproteolytic enzymes (Birkett et al. (1991) Anal Biochem 196:137–143; Petithory et al. (1991) PNAS 88:11510–11514). In these experiments, a series of amino acids was substituted at a single position within the substrate sequence. After proteolysis, Edman degradation was used to quantitate the yield of each amino acid component in the hydrolysis product and hence to evaluate the relative $k_{cat}/K_m$ values for each substrate in the mixture.

However, it is noted that the operational simplicity of synthesizing many peptides by coupling monomer mixtures is offset by the difficulty in controlling the composition of the products. The product distribution reflects the individual; rate constants for the competing coupling reactions, with activated derivatives of sterically hindered residues such as valine or isoleucine adding at a significantly slower rate than glycine or alanine for example. The nature of the resin-bound component of the acylation reaction also influences the addition rate, and the relative rate constants for the formation of 400 dipeptides form the 20 genetically coded amino acids have been determined by Rutter and Santi (Rutter et al. (1991) U.S. Pat. No. 5,010,175). These reaction rates can be used to guide the selection of appropriate relative concentrations of amino acids in the mixture to favor more closely equimolar coupling yields.

(iii.c.4) Multiple Peptide Synthesis on Nontraditional Solid Supports

The search for innovative methods of multiple peptide synthesis has led to the investigation of alternative polymeric supports to the polystyrene-divinylbenzene matrix originally popularized by Merrifield. Cellulose, either in the form of paper disks (Blankemeyer-Menge et al. (1988) Tetrahedron Lett 29-5871–5874; Frank et al. (1988) Tetrahedron 44: 6031–6040; Eichler et al. (1989) Collect Czech Chem Commun 54:1746–1752; Frank, R. (1993) Bioorg Med Chem Lett 3:425–430) or cotton fragments (Eichler et al. (1991) Pept Res 4: 296–307; Schmidt et al. (1993) Bioorg Med Chem Lett 3:441–446) has been successfully functionalized for peptide synthesis. Typical loadings attained with cellulose paper range from 1 to 3 mmol/cm$^2$, and HPLC analysis of material cleaved from these supports indicates a reasonable quality for the synthesized peptides. Alternatively, peptides may be synthesized on cellulose sheets via non-cleavable linkers and then used in ELISA-based binding studies (Frank, R. (1992) Tetrahedron 48:9217–9232). The porous, polar nature of this support may help suppress unwanted nonspecific protein binding effects. By controlling the volume of activated amino acids and other reagents spotted on the paper, the number of peptides synthesized at discrete locations on the support can be readily varied. In one convenient configuration spots are made in an 8×12 microtiter plate format. Frank has used this technique to map the dominant epitopes of an antiserum raised against a human cytomegalovirus protein, following the overlapping peptide screening (Pepscan) strategy of Geysen (Frank, R. (1992) Tetrahedron 48:9217–9232). Other membrane-like supports that may be used for multiple solid-phase synthesis include polystyrene-grafted polyethylene films (Berg et al. (1989) J. Am. Chem. Soc. 111:8024–8026).

(iii.c.5) Combinatorial Libraries by Light-Directed, Spatially Addressable Parallel Chemical Synthesis A scheme of combinatorial synthesis in which the identity of a compound is given by its locations on a synthesis substrate is termed a spatially addressable synthesis. In one embodiment, the combinatorial process is carried out by controlling the addition of a chemical reagent to specific locations on a solid support (Dower et al. (1991) Annu. Rep. Med. Chem. 26:271–280; Fodor, S. P. A. (1991) Science 251:767; Pirrung et al. (1992) U.S. Pat. No. 5,143,854; Jacobs et al. (1994) Trends Biotechnol 12:19–26). The technique combines two well-developed technologies: solid-phase peptide synthesis chemistry and photolithography. The high coupling yields of Merrifield chemistry allow efficient peptide synthesis, and the spatial resolution of photolithography affords miniaturization. The merging of these two technologies is done through the use of photo-labile amino protecting groups in the Merrifield synthetic procedure.

The key points of this technology are illustrated in Gallop et al. (1994) J Med Chem 37:1233–1251. A synthesis substrate is prepared for amino acid coupling through the covalent attachment of photolabile nitroveratryloxycarbonyl (NVOC) protected amino linkers. Light is used to selectively activate a specified region of the synthesis support for coupling. Removal of the photolabile protecting groups by lights (deprotection) results in activation of selected areas. After activation, the first of a set of amino acids, each bearing a photolabile protecting group on the amino terminus, is exposed to the entire surface. Amino acid coupling only occurs in regions that were addressed by light in the preceding step. The solution of amino acid is removed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed. The target protein can be labeled with a fluorescent reporter group to facilitate the identification of specific interactions with individual members of the matrix. In a light-directed chemical synthesis, the products depend on the pattern of illumination and on the order of addition of reactants. By varying the lithographic patterns, many different sets of test peptides can be synthesized in the same number of steps; this leads to the generated of many different masking strategies.

(iii.c.6) Encoded Combinatorial Libraries

In yet another embodiment, the subject method utilizes a peptide library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries above, where activity derives from expressed peptides, but the structures of the active peptides are deduced from the corresponding genomic DNA sequence. The first encoding of synthetic combinatorial libraries employed DNA as the code. Two forms of encoding have been reported: encoding with sequenceable bio-oligomers (e.g., oligonucleotides and peptides), and binary encoding with non-sequenceable tags.

(iii.c.6.a) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally 77 (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following these techniques, the peptide libraries can be derived for use in the subject method and screened using the D-enantiomer of the target protein.

It is noted that an alternative approach useful for generating nucleotide-encoded synthetic peptide libraries employs a branched linker containing selectively protected OH and $NH_2$ groups (Nielsen et al. (1993) J. Am. Chem. Soc 115:9812–9813; and Nielsen et al. (1994) Methods Compar. Methods Enzymol 6:361–371). This approach requires that equimolar quantities of test peptide and tag co-exist, though this may be a potential complication in assessing biological activity, especially with nucleic acid-based targets.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis on non-oligomeric libraries. In preferred embodiments, the libraries employ linkers permitting selective detachment of the test peptide library member for bioassay, in part (as described infra) because assays employing beads limit the choice of targets, and in part because the tags are potentially susceptible to biodegradation.

Peptides themselves have been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115: 2529–2531), orthogonality in synthesis is achieved by employing acid-labile protection for the coding strand and base-labile protection for the ligand strand.

In an alternative approach (Nikolaiev et al. (1993) Pept Res 6:161–170), branched linkers are employed so that the coding unit and the test peptide are both attached to the same functional group on the resin. In one embodiment, a linker can be placed between the branch point and the bead so that cleavage releases a molecule containing both code and ligand (Ptek et al. (1991) Tetrahedron Lett 32:3891–3894). In another embodiment, the linker can be placed so that the test peptide can be selectively separated from the bead, leaving the code behind. This last construct is particularly valuable because it permits screening of the test peptide without potential interference, or biodegradation, of the coding groups. Examples in the art of independent cleavage and sequencing of peptide library members and their corresponding tags have confirmed that the tags can accurately predict the peptide structure.

It is noted that peptide tags are more resistant to decomposition during ligand synthesis than are oligonucleotide tags, but they must be employed in molar ratios nearly equal to those of the ligand on typical 130 mm beads in order to be successfully sequenced. As with oligonucleotide encoding, the use of peptides as tags requires complex protection/deprotection chemistries.

(iii.c.6.b) Non-Sequenceable Tagging: Binary Encoding

An alternative form of encoding the test peptide library employs a set of non-sequenceable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode 240 (e.g., upwards of 1012) different molecules. In the original report (Ohlmeyer et al., supra) the tags were bound to about 1% of the available amine groups of a peptide library via a photocleavable O-nitrobenzyl linker. This approach is convenient when preparing combinatorial libraries of peptides or other amine-containing molecules. A more versatile system has, however, been developed that permits encoding of essentially any combinatorial library. Here, the ligand is attached to the solid support via the photocleavable linker and the tag is attached through a catechol ether linker via carbene insertion into the bead matrix (Nestler et al. (1994) J. Org. Chem. 59:4723–4724). This orthogonal attachment strategy permits the selective detachment of library members for bioassay in solution and subsequent decoding by ECGC after oxidative detachment of the tag sets.

Binary encoding with electrophoric tags has been particularly useful in defining selective interactions of substrates with synthetic receptors (Borchardt et al. (1994) J. Am. Chem. Soc. 116:373–374), and model systems for understanding the binding and catalysis of biomolecules. Even using detailed molecular modeling, the identification of the selectivity preferences for synthetic receptors has required the manual synthesis of dozens of potential substrates. The use of encoded libraries makes it possible to rapidly examine all the members of a potential binding set. The use of binary-encoded libraries has made the determination of binding selectivities so facile that structural selectivity has been reported for four novel synthetic macrobicyclic and tricyclic receptors in a single communication (Wennemers et al. (1995) J. Org. Chem. 60:1108–1109; and Yoon et al. (1994) Tetrahedron Lett 35:8557–8560) using the encoded library mentioned above.

Similar facility in defining specificity of interaction would be expected for many other biomolecules.

Although the several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject peptide library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays.

Successive photoelution also permits a very high throughput iterative screening strategy: first, multiple beads are placed in 96-well microtiter plates; second, ligands are partially detached and transferred to assay plates; third, a bioassay identifies the active wells; fourth, the corresponding beads are rearrayed singly into new microtiter plates; fifth, single active compounds are identified; and sixth, the structures are decoded.

The above approach was employed in screening for carbonic anhydrase (CA) binding and identified compounds which exhibited nanomolar affinities for CA. Unlike sequenceable tagging, a large number of structures can be rapidly decoded from binary-encoded libraries (a single ECGC apparatus can decode 50 structures per day). Thus, binary-encoded libraries can be used for the rapid analysis of structure-activity relationships and optimization of both potency and selectivity of an active series. The synthesis and screening of large unbiased binary encoded peptide libraries for lead identification, followed by preparation and analysis of smaller focused libraries for lead optimization, offers a particularly powerful approach to drug discovery using the subject method.

(iii.d) Nucleic Acid Libraries

In another embodiment, the library is comprised of a variegated pool of nucleic acids, e.g., single or double-stranded DNA or an RNA. A variety of techniques are known in the art for generating screenable nucleic acid libraries which may be exploited in the present invention. The libraries that can be used with the instant invention include libraries generated from: synthetic oligonucleotides, cDNA sequence, bacterial genomic DNA fragments, and eukaryotic genomic DNA fragments.

In particular, many of the techniques described above for synthetic peptide libraries can be used to generate nucleic acid libraries of a variety of formats. For example, divide-couple-recombine techniques can be used in conjugation with standard nucleic acid synthesis techniques to generate bead immobilized nucleic acid libraries.

In another embodiment, solution libraries of nucleic acids can be generated which rely on PCR techniques to amplify for sequencing those nucleic acid molecules which selectively bind the screening target. By such techniques, libraries approaching $10^{15}$ different nucleotide sequences have been generated in solution (see, for example, Bartel and Szostak (1993) Science 261: 1411–1418; Bock et al. (1992) Nature 355: 564; Ellington et al. (1992) Nature 355: 850–852; and Oliphant et al. (1989) Mol Cell Biol 9: 2944–2949). According to one embodiment of the subject method, the SELEX (systematic evolution of ligands by exponential enrichment) is employed with the enantiomeric screening target. See, for example, Tuerk et al. (1990) Science 249:505–510 for a review of SELEX. Briefly, in the first step of these experiments on a pool of variant nucleic acid sequences is created, e.g., as a random or semi-random library. In general, an invariant 3' and (optionally) 5' primer sequence are provided for use with PCR anchors or for permitting subcloning. The nucleic acid library is applied to screening a target, and nucleic acids which selectively bind (or otherwise act on the target) are isolated from the pool. The isolates are amplified by PCR and subcloned into, for example, phagemids. The phagemids are then transfected into bacterial cells, and individual isolates can be obtained and the sequence of the nucleic acid cloned from the screening pool can be determined.

When RNA is the test ligand, the RNA library can be directly synthesized by standard organic chemistry, or can be provided by in vitro translation as described by Tuerk et al., supra. Likewise, RNA isolated by binding to the screening target can be reverse transcribed and the resulting cDNA subcloned and sequenced as above.

Isolation of mRNA for cDNA synthesis and isolation of genomic DNA, either of prokaryotic or eukaryotic origin, are well-known in the art of molecular biology. Many standard laboratory manuals such as *Current Protocols in Molecular Biology*, John Wiley & Sons, N.Y. (1989 or later editions), or *Molecular Cloning: A Laboratory Manual*, Cold Spring Harbor press (1989 or later editions) have detailed description of these subjects. In addition, many companies offer commercial kits specifically designed for such purposes.

(iii.e) Small Molecule Libraries

Recent trends in the search for novel pharmacological agents have focused on the preparation of chemical libraries. Peptide libraries are described above. Nucleic acid libraries (including cDNA, genomic DNA and EST libraries) are well-known in the art. Saccharide libraries and their synthesis using combinatory chemistry have been described in WO 98/16536 and its related applications. However, the field of combinatorial chemistry has also provided large numbers of non-polymeric, small organic molecule libraries which can be employed in the subject method.

Exemplary combinatorial libraries include benzodiazepines, peptoids, biaryls and hydantoins. In general, the same techniques described above for the various formats of chemically synthesized peptide libraries may also be used to generate and (optionally) encode synthetic non-peptide libraries.

(iii.f) Selecting Compounds from the Library

As with the diversity contemplated for the compound library and form in which the compound library is provided, the subject method is envisaged to identify hybrid ligands with the general formula of MTX-L1-L2 which interacts with a polypeptide screening target or to identify inhibitors or antagonists of a certain interaction. In most embodiments, the screening programs test libraries of compounds/hybrid ligands suitable for high throughput analysis in order to maximize the number of compounds surveyed in a given period of time. However, as a general rule, the screening portion of the subject method involves contacting the screening target with the compound library and isolating those compounds from the library which interact with the screening target or causing a desired effect. Such interaction between the test compound/hybrid ligands and the screening target may be detected, for example, based on the change of status of any one of the suitable reporter system as described in section 3, or modulation of an enzymatic/catalytic activity of the screening target (for example, when the binding of a hybrid ligand for its potential dimerizable target is tested). The efficacy of the test compounds can be assessed by generating dose response curves from data obtained using various concentrations of the test compound. Moreover, a control assay can also be performed to provide a baseline for comparison.

In one embodiment, the variegated compound library is subjected to affinity enrichment in order to select for compounds which bind a preselected screening target. The term "affinity separation" or "affinity enrichment" includes, but is not limited to (1) affinity chromatography utilizing immobilizing screening targets, (2) precipitation using screening targets, (3) fluorescence activated cell sorting where the compound library is so amenable, (4) agglutination, and (5) plaque lifts. In each embodiment, the library of compounds are ultimately separated based on the ability of a particular compound to bind a screening target of interest. See, for example, the Ladner et al. U.S. Pat. No. 5,223,409; the Kang et al. International Publication No. WO 92/18619; the Dower et al. International Publication No. WO 91/17271; the Winter et al. International Publication WO 92/20791; the Markland et al. International Publication No. WO 92/15679; the Breitling et al. International Publication WO 93/01288; the McCafferty et al. International Publication No. WO 92/01047; the Garrard et al. International Publication No. WO 92/09690; and the Ladner et al. International Publication No. WO 90/02809.

It will be apparent that, in addition to utilizing binding as the separation criteria, compound libraries can be fractionated based on other activities of the target molecule, such as modulation of catalytic activity or certain biochemical properties.

In one embodiment, binding between a chemical compound and a target polypeptide can be measured by the activity of the reporter system as described above. The activity to be detected could be transcription activity, fluorescence, enzymatic activity, or any other biological or biochemical activity. If a transcription based reporter system is used for the detection, transcription activity of the reporter moiety can be monitored to screen for the compound or the polypeptide binding to their target. Those skilled in the art will readily appreciate and recognize other appropriate methods suitable for those screens.

(iv) Polypeptides of the Present Invention

The present invention provides methods to identify polypeptides that interact with a given ligand. Polypeptides identified through such methods can be produced in large quantity using any art-recognized methods, either as a purified polypeptide, or as a purified fusion polypeptide with other polypeptides. All forms of polypeptides can be formulated, with an acceptable pharmaceutical excipient, into a pharmaceutical composition using any art-recognized methods.

Such a purified polypeptide will be isolated from, or otherwise substantially free of other cellular proteins. The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned gene as described herein. Preferred subject polypeptides have an amino acid sequence which is at least about 60%, 65%, 66%, 67%, 68%, 69%, 70%, 71%, 72%, 73%, 74%, 75%, 76%, 77%, 78%, 79%, 80%, 85%, 90%, or 95% identical or homologous to an amino acid sequence. Even more preferred subject polypeptides comprise an amino acid sequence of at least 10, 20, 30, or 50 residues which is at least about 70, 80, 90, 95, 97, 98, or 99% homologous or identical to an amino acid sequence. Such proteins can be recombinant proteins, and can be, e.g., produced in vitro from nucleic acids comprising a nucleotide sequence identified by the methods of the invention or homologs thereof. For example, recombinant polypeptides preferred by the present invention can be encoded by a nucleic acid, which is at least 85% homologous and more preferably 90% homologous and most preferably 95% homologous with a nucleotide sequence identified by the methods of the invention-Polypeptides which are encoded by a nucleic acid that is at least about 98–99% homologous with the sequence identified by the methods of the invention are also within the scope of the invention.

The scope of the invention also includes isoforms of the subject polypeptides encoded by splice variants. Such isoforms may have identical or different biological activities. Such isoforms may arise, for example, by alternative splicing of one or more gene transcripts. Full length proteins or fragments corresponding to one or more particular motifs and/or domains or to arbitrary sizes, for example, at least 5, 10, 20, 25, 50, 75 or 100 amino acids in length are within the scope of the present invention.

For example, isolated polypeptides can be encoded by all or a portion of a nucleic acid sequence. Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a subject polypeptide may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") protein.

A polypeptide can be a membrane bound form or a soluble form. A preferred soluble polypeptide is a polypeptide which does not contain a hydrophobic signal sequence domain. Such proteins can be created by genetic engineering by methods known in the art. The solubility of a recombinant polypeptide may be increased by deletion of hydrophobic domains, such as predicted transmembrane domains, of the wild type protein.

In general, polypeptides referred to herein as having an activity (e.g., are "bioactive") of a protein are defined as polypeptides which include an amino acid sequence encoded by all or a portion of the nucleic acid sequences and which mimic or antagonize all or a portion of the biological/biochemical activities of a naturally occurring protein. Examples of such biological activity include a region of conserved structure referred to as the conserved domain.

Other biological activities of the subject proteins will be reasonably apparent to those skilled in the art. According to the present invention, a polypeptide has biological activity if it is a specific agonist or antagonist of a naturally occurring form of a protein.

In addition to utilizing fusion proteins to enhance immunogenicity, it is widely appreciated that fusion proteins can also facilitate the expression of proteins, and accordingly, can be used in the expression of the polypeptides of the present invention. For example, polypeptides can be generated as glutathione-S-transferase (GST-fusion) proteins. Such GST-fusion proteins can enable easy purification of the polypeptide, as for example by the rise of glutathione-derivatized matrices (see, for example, Current Protocols in Molecular Biology, eds, Ausubel et al. (N.Y.: John Wiley & Sons, 1991)). Additionally, fusion of polypeptides to small epitope tags, such as the FLAG or hemaglutinin tag sequences, can be used to simplify immunological purification of the resulting recombinant polypeptide or to facilitate immunological detection in a cell or tissue sample. Fusion to the green fluorescent protein, and recombinant versions thereof which are known in the art and available commercially, may further be used to localize polypeptides within living cells and tissue.

The subject polypeptides may be produced by any method known in the art. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In, a preferred embodiment, the recombinant polypeptide is a fusion protein containing a domain which facilitates its purification, such as GST fusion protein.

Moreover, it will be generally appreciated that, under certain circumstances, it may be advantageous to provide homologs of one of the subject polypeptides which function in a limited capacity as one of either an agonist (mimetic) or an antagonist in order to promote or inhibit only a subset of the biological activities of the naturally occurring form of the protein. Thus, specific biological effects can be elicited by treatment with a homolog of limited function, and with fewer side effects relative to treatment with agonists or antagonists which are directed to all of the biological activities of naturally occurring forms of proteins.

Homologs of each of the subject proteins can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the protein can be generated which are able to inhibit the function of the naturally occurring form of the protein, such as by competitively binding to a receptor.

The recombinant polypeptides of the present invention also include homologs of the wild-type proteins, such as versions of those proteins which are resistant to proteolytic cleavage, as for example, due to mutations which alter ubiquitination or other enzymatic targeting associated with the protein.

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N or C-terminus of the polypeptide.

Modification of the structure of the subject polypeptides can be for such purposes as enhancing therapeutic or prophylactic efficacy, stability (e.g., ex vivo shelf life and resistance to proteolytic degradation), or post-translational modifications (e.g., to alter the phosphorylation pattern of protein). Such modified peptides, when designed to retain at least one activity of the naturally occurring form of the protein, or to produce specific antagonists thereof, are considered functional equivalents of the polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e., isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed by L. Stryer, WFT Freeman and Co.: 1981). Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates the generation of sets of combinatorial mutants of the subject polypeptides as well as truncation mutants, and is especially useful for identifying potential variant sequences (e.g., homologs). The purpose of screening such combinatorial libraries is to generate, for example, novel homologs which can act as either agonists or antagonist, or alternatively, possess novel activities all together. Thus, combinatorially derived homologs can be generated to have an increased potency relative to a naturally occurring form of the protein.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g., for phage display) containing the set of sequences therein.

There are many ways by which such libraries of potential homologs can be generated from a degenerate oligonucleotide sequence. Chemical synthesis of a degenerate gene sequence can be carried out in an automatic DNA synthesizer, and the synthetic genes then ligated into all appropriate expression vector. The purpose of a degenerate set of genes is to provide, in one mixture, all of the sequences encoding the desired set of potential sequences. The synthesis of degenerate oligonucleotides is well known in the art (see for example, Narang, S A (1983) Tetrahedron 39:3; Itakura et al. (1981) Recombinant DNA, Proc 3d Cleveland Sympos. Macromolecules, ed: A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89: 2429–2433; Devlin et al. (1990)

Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for any clone in order to generate a variegated population of fragments for screening and subsequent selection of bioactive fragments. A variety of techniques are known in the art for generating such libraries, including chemical synthesis. In one embodiment, a library of coding sequence fragments can be generated by (i) treating a double-stranded PCR fragment of an coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with S1 nuclease; and (v) ligating the resulting fragment library into an expression vector. By this exemplary method, an expression library can be derived which codes for N-terminal, C-terminal, and internal fragments of various sizes.

The invention also provides for reduction of the proteins to generate mimetics, e.g., peptide or non-peptide agents, such as small molecules, which are able to disrupt binding of a subject polypeptide with a molecule, e.g., target peptide. Thus, such mutagenic techniques as described above are also useful to map the determinants of the proteins which participate in protein—protein interactions involved in, for example, binding of the subject polypeptide to a target peptide. To illustrate, the critical residues of a subject polypeptide which are involved in molecular recognition of its receptor can be determined and used to generate derived peptidomimetics or small molecules which competitively inhibit binding of the authentic protein with that moiety. By employing, for example, scanning mutagenesis to map the amino acid residues of the subject proteins which are involved in binding other proteins, peptidomimetic compounds can be generated which mimic those residues of the protein which facilitate the interaction. Such mimetics may then be used to interfere with the normal function of a protein. For instance, non-hydrolyzable peptide analogs of such residues can be generated using benzodiazepine (e.g., see Freidinger et al. in Peptides: Chemistry and Biology, G. R-Marshall ed., ESCOM Publisher: Leiden, Netherlands, 1988), azepine (e.g., see Huffman et al. in Peptides: Chemistry and Biology, G. R. Marshall ed., ESCOM Publisher. Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methyleue pseudopeptides (Ewenson et al. (1986) J Med Chem 29:295; and Ewenson et al. in Peptides: Structure and Function (Proceedings of the American Peptide Symposium) Pierce Chemical Co, Rockland, Ill., 1985), β-turn dipeptide cores (Nagai et al. (1985) Tetrahedron Lett 26:647; and Sato et al. (1986) J. Chem Soc Perkin Trans 1:1231), and β-aminoalcohols (Gordon et al. (1985) Biochem Biophys Res Commun 126:419; and Dann et al. (1986) Biochem Biophys Res Commun 134:71).

(v) Kits

The invention further provides kits for creating hybrid ligands which include a predetermined chemical ligand. The compound or agent can be packaged in a suitable container. The kit can further comprise instructions for using the kit to isolate binding proteins for the predetermined ligand of the hybrid ligand.

Thus, one aspect of the invention provides a kit comprising a polynucleotide encoding at least one ligand-binding domain and a functional domain heterologous to the ligand-binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure MTX-L1-L2, and 2) to test the binding between the hybrid ligand and the ligand-binding domain, wherein one of MTX and L2 binds to or inhibits a kinase.

Another aspect of the invention provides a kit comprising a polynucleotide encoding at least one ligand binding domain and a functional domain heterologous to the ligand-binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure MTX-L1-L2, and 2) to test the binding between the hybrid ligand and the ligand-binding domain, wherein Y is of the general structure $(CH_2-W-CH_2)_p$, where W represents O, S, SO, or $SO_2$, and p is an integer from 2 to 25.

Another aspect of the invention provides a kit comprising a polynucleotide encoding at least one ligand binding domain and a functional domain heterologous to the ligand-binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure MTX-L1-L2, and 2) to test the binding between the hybrid ligand and the ligand-binding domain, e.g., wherein the functional domain is Cub or Nux.

Another aspect of the invention provides a kit comprising: 1) a compound of general structure MTX-L1-L2, wherein Y is of the general structure $(CH_2-W-CH_2)_n$ and L2 is a chemical group that is easily substituted by a different chemical group, and 2) instructions to use the compound for the synthesis of a hybrid ligand MTX-L1-L2 where MTX is different from L2, and at least one of MTX and L2 is not a peptide.

(vi) Business Methods

Other aspects of the invention provides for certain methods of doing business. In particular, practicing the methods of the invention may identify certain hybrid ligands, inhibitors and polypeptides. This technical step, when combined with one of more additional steps, provides for novel approaches to conduct a pharmaceutical, agrochemical, biotechnological, or preferably a life-science business. For example, such compositions identified by the method of the invention may be tested for efficacy as therapeutics in a variety of disease models, the potential therapeutic compositions then tested for toxicity and other safety-profiling before formulating, packaging and subsequently marketing the resulting formulation for the treatment of disease. Alternatively, the rights to develop and market such formulations or to conduct such steps may be licensed to a third party for consideration. In certain other aspects of the invention, the hybrid ligands, inhibitors, and polypeptides thus identified may have utility in the form of information that can be provided to a third party for consideration such that an improved understanding of the function or side effects of said hybrid ligands, inhibitors, and polypeptides in a biological or therapeutic context.

By way of example, a particular preferably method of doing business comprises:
(i) identifying a polypeptides binding to a hybrid ligand of general formula MTX-L1-L2, wherein L1 is of the general structure $(CH_2-W-CH_2)_p$, MTX is different from L2, and at least one of MTX and L2 is not a peptide, W=O, S, SO or $SO_2$, n is an integer in the range of 2 to 5 and wherein said polypeptides were previously not known to bind to such hybrid ligand, and
(ii) providing access to data, nucleic acids or polypeptides obtained from such identification for use by another party.

The present invention further discloses novel compositions of methotrexate-containing heterodimeric probe molecules and facile syntheses of said probe molecules and their intermediates. The convergent approach of the syntheses, the solubility of the intermediates in standard organic media, and the increased hydrophobicity of the intermediates make possible an efficient isolation and purification of the target molecules and intermediates.

Accordingly, one aspect of the instant invention is a methotrexate-containing heterodimeric probe represented by the general structure shown in Formula I:

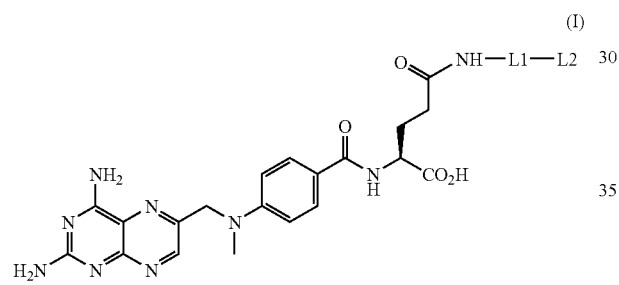

(I)

wherein
L1 represents a spacer-linking group and L2 represents a putative or unknown small-molecule protein ligand;
$R_1$, independently for each occurrence, represents H or a lower alkyl; and
L2 is a small molecule ligand for a protein receptor covalently attached to L1 via an alkyl, alkenyl, alkynyl, —O—, C(=X) (wherein X is $NR_1$, O or S), —OC(O)—, —$NR_1$—, —$NR_1$CO—, —C(O)$NR_1$—, —S(O)$_n$— (wherein n is 0, 1, 2, or 3), —S(O)$_2$—$NR_1$—, —$NR_1$—S(O)$_2$—, —OC(O)—$NR_1$, —$NR_1$—C(O)—$NR_1$—, —$NR_1$—C(=$NR_1$)—$NR_1$—, and —B(O$R_1$)$_m$— (wherein m is 1 or 2), or —P(O)$_k$— (wherein k is 2 or 3) group.

The spacer-linking group is a hydrocarbylene group wherein one or more methylene groups is optionally replaced by a group Y (provided that none of the Y groups are adjacent to each other), wherein each Y, independently for each occurrence, is selected from substituted or unsubstituted aryl, heteroaryl, cycloalkyl, heterocycloalkyl, C(=X) (wherein X is $NR_1$, O or S), —O—, —OC(O)—, —$NR_1$—, —$NR_1$CO—, —C(O)$NR_1$—, —S(O)$_n$— (wherein n is 0, 1, or 2), —OC(O)—$NR_1$, —$NR_1$—C(O)—$NR_1$—, —$NR_1$—C($NR_1$)—$NR_1$—, and —B(O$R_1$)—;

In one embodiment L1 comprises —$CH_2$—($CH_2$—W—$CH_2$)$_p$—$CH_2$— wherein W represents N, O, or S and p is an integer in the range of 1 to 8. Preferably L1 consists essentially of such liner, or even more preferably represents polyethylene glycol chain.

In certain embodiments, Y is absent. In other embodiments, Y represents at least one occurrence of C(=X) (wherein X is as defined above), —O—, —$NR_1$CO—, or —C(O)$NR_1$—, —S(O)$_n$— (wherein n is 0, 1, 2, or 3). In certain embodiments, Y represents at least one occurrence of —S(O)$_2$—$NR_1$—, —$NR_1$—S(O)$_2$—, —OC(O)—$NR_1$, —$NR_1$—C(O)—$NR_1$—, —$NR_1$—C($NR_1$)—$NR_1$—; and $R_1$ is hydrogen or a lower alkyl. In preferred embodiments, Y represents at least one occurrence —$NR_1$—S(O)$_2$—, —OC(O)—$NR_1$, or —$NR_1$—C(O)—$NR_1$—.

In some embodiments, L2 is covalently attached to L1 via an —O—, C(=X) (wherein X is as defined above), —OC(O)—, —$NR_1$—, —$NR_1$ CO—, —C(O)$NR_1$—, or —S(O)$_n$— (wherein n is 0, 1, or 2) linkage.

Another aspect of the instant invention is the compound shown in Formula II which is an intermediate in the synthesis of the structure shown in Formula I.

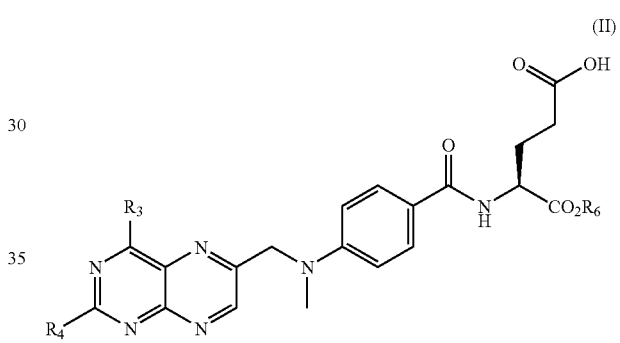

(II)

wherein,
$R_3$ and $R_4$ each represent $NR_5Z$;
$R_5$ is absent or represents hydrogen or lower alkyl;
Z represents t-Boc, Fmoc, Cbz, trialkylsilyl,

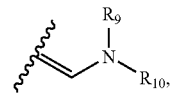

or an acid-labile amino-protecting group in exactly one occurrence, and for all other occurrences represents hydrogen;
$R_6$ represents an alkyl, aryl, trialkylsilylalkyl, or an acid-labile carboxy-protecting group; and
$R_9$ and $R_{10}$, independently for each occurrence, represent hydrogen or (un)substituted alkyl, (un)substituted alkenyl, (un)substituted alkynyl, (un)substituted heteroalkyl, (un)substituted aryl, or (un)substituted heteroaryl.

In certain embodiments $R_6$ is an acid-labile carboxy protecting group; Z is t-boc, and $R_5$ represents hydrogen or lower alkyl, preferably hydrogen.

Another aspect of the instant invention is a method for synthesizing the structure shown in Formula I:

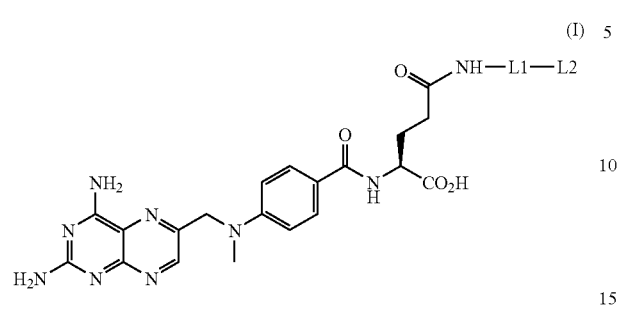

wherein,
L1 and L2 are as defined above;

comprising,
a. coupling the structure represented by Formula II with $H_2N$-L1-L2 to form an amide linkage;

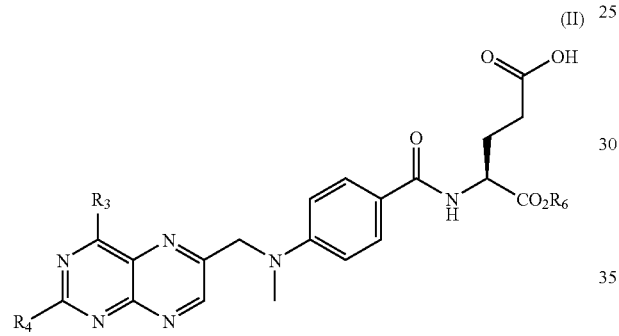

wherein, $R_3$, $R_4$ and $R_6$ are as defined above; and
b. removing protecting groups at the $R_3/R_4$ and $R_6$ positions.

In certain embodiments the amide linkage is formed using coupling reagents employed in peptide coupling reactions known in the art. (See Bodansky, Principles of Peptide Synthesis, $2^{nd}$ ed., Berlin; New York: Springer-Verlag, c1993; Bodansky, Peptide Chemistry: A practical textbook, $2^{nd}$ ed., Berlin; New York: Springer-Verlag, c1993) In preferred embodiments, the coupling reagents comprise N-ethyl-N'-(3-dimethyl aminopropyl)-carbodiimide hydrochloride (EDC), N-Hydroxybenzotriazole Monohydrate (HOBT), and an alkyl amine such as diisopropylethylamine (DIEA).

In certain embodiments the $R_3$ or $R_4$ represent $NR_5Z$ wherein $R_5$ is hydrogen, and Z represents t-Boc in exactly one occurrence, and for all other occurrences represents hydrogen, and $R_6$ represents a t-butyl group. For example, but without limitation, in certain embodiments $R_3$ is NHBoc and $R_4$ is $NH_2$ In certain embodiments, the protecting groups at $R_3$/and $R_6$ groups are removed using the same deprotecting reagent in a one-pot process. In certain embodiments, the deprotecting reagent is trifluoroacetic acid in an aqueous or halogenated hydrocarbon solvent such as dichloromethane. In certain preferred embodiments, the deprotecting agent is 90% TFA/10% $H_2O$. In other embodiments, the protecting groups at $R_3/R_4$ and $R_6$ are removed sequentially using two different deprotecting conditions.

Another aspect of the instant invention is a synthesis of the structure shown in Formula II:

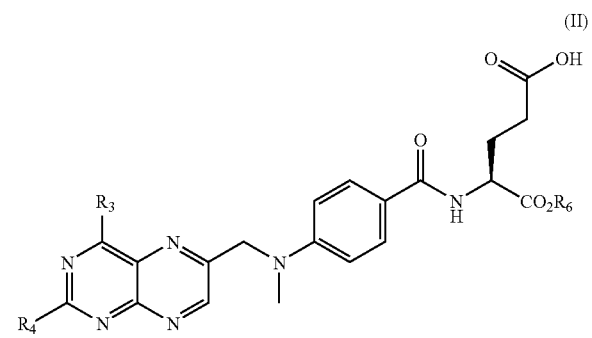

wherein
$R_3$ and $R_4$ each represent $NR_5Z$;
$R_5$ is absent or represents hydrogen or lower alkyl, (preferably hydrogen);
Z represents t-Boc, Fmoc, Cbz, trialkylsilyl,

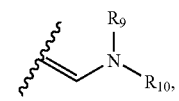

or an acid-labile amino-protecting group in exactly one occurrence, and for all other occurrences represents hydrogen;
$R_6$ represents an alkyl, aryl, trialkylsilylalkyl, or an acid-labile carboxy-protecting group; and
$R_9$ and $R_{10}$, independently for each occurrence, represent hydrogen or (un)substituted alkyl, (un)substituted alkenyl, (un)substituted alkynyl, (un)substituted heteroalkyl, (un)substituted aryl, or (un)substituted heteroaryl;

comprising
a. Reacting the structure represented by IIa with $Boc_2O$ (1 equiv), an alkyl amine base such as diisopropylethylamine (DIEA), and a nucleophilic catalyst such as dimethylaminopyridine (DMAP) in a suitable solvent (preferably a halogenated hydrocarbon);

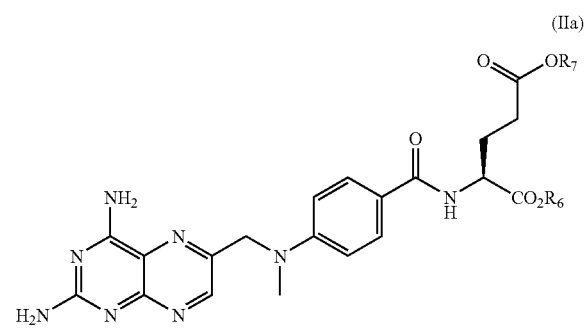

wherein $R_7$ represents an alkyl, aryl, trialkylsilylalkyl, or an acid-labile carboxy protecting group; and
b. Removing $R_7$ to yield the structure represented by Formula II.

In certain embodiments the halogenated hydrocarbon solvent is dichloromethane. In certain embodiments, $R_6$ represents CH₃, ᵗBu, Bn, CH₂—CH₂—SiMe₃. In preferred embodiments, $R_6$ represents ᵗBu.

In certain embodiments, $R_7$ represents hydrogen, CH₃, ᵗBu, Bn, CH₂—CH₂—SiMe₃. In preferred embodiments, $R_7$ represents a CH₃.

Another aspect of the present invention is a method for treating a disease, comprising administering to a patient compound identified in an assay comprising (a) forming a reaction mixture including:
  (i) a heterodimeric probe molecule represented by Formula I;
  (ii) a DNA binding fusion protein;
  (iii) a transcriptional activator fusion protein; and
(b) detecting interaction of the heterodimeric probe molecule with the DNA-binding fusion protein and activation-domain fusion protein by monitoring transcription of a reporter gene.

In certain embodiments, the assay is carried out in a yeast cell. In certain embodiments the compound is selected from a small molecule library. In certain embodiments, the DNA binding fusion protein is a DNA binding protein-DHFR fusion protein. In certain embodiments, the transcriptional activator is a yeast GAL4 system, or a mammalian karyoplasmic interaction selection strategy (KISS) system. In certain embodiments, the transcriptional activator is fused to a polypeptide selected from a cDNA library. In certain embodiments, the reporter gene is selected from lacZ, gfp, yfp, bfp, cat, luxAB, HPRT or a cell surface marker gene. In certain embodiments, the reporter gene imparts antibiotic sensitivity or resistance.

Another aspect of the invention is pharmaceutical composition of a ligand identified using a heterodimeric probe molecule as prepared herein. The ligand may be an agonist, antagonist, or inhibitor of a receptor or protein. For example, such a composition can be a pharmaceutical composition of a CDK inhibitor identified in a three-hybrid assay which uses a heterodimeric probe molecule containing methotrexate covalently linked to the CDK inhibitor as prepared herein.

Another aspect of the invention is a method of treating an animal using a pharmaceutical composition of a protein or receptor ligand identified using a heterodimeric probe molecule as prepared herein. Not intending to limit the scope of the treatment to the following examples, the treatment may be for prevention or cure of a pathogenic infection caused by a bacteria, mycobacteria, fungus, or virus; neurological diseases such as Alzheimer disease, Parkinson's disease; autoimmune diseases such as diabetes and multiple sclerosis; or uncontrolled cell growth as in breast, and prostate cancer. In certain embodiment, the treatment is for modulating the immune system of an animal, such as a mammal, e.g., a human.

Another aspect of the present invention is an assay for identifying a protein receptor for a known ligand comprising a DNA binding fusion protein, a heterodimeric probe molecule prepared as disclosed herein wherein L2 is a putative protein ligand, and an activation domain fusion protein, wherein the protein target is selected from a cDNA library of polypeptides. In certain embodiments, the assay is carried out in a yeast system.

An exemplary synthetic scheme for synthesizing a spacer linking group is shown in Scheme 1.

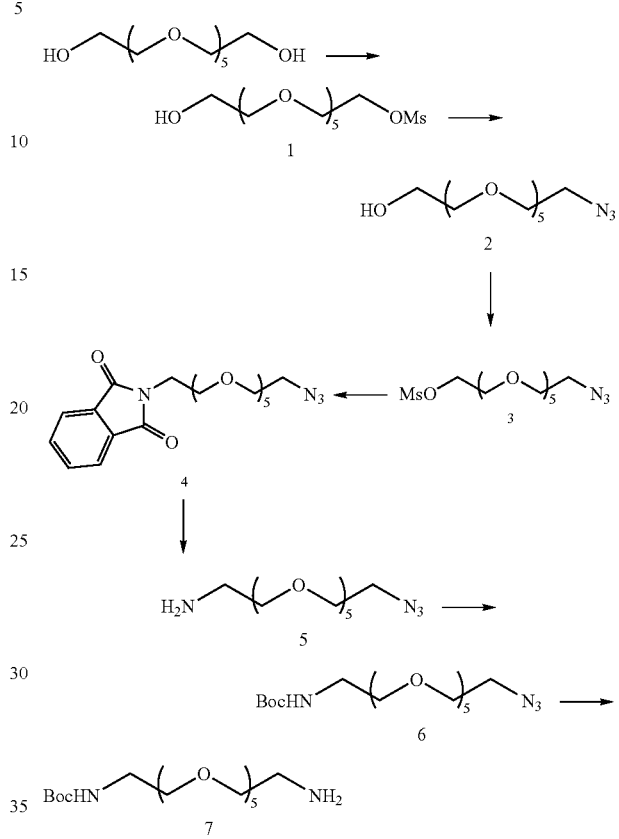

An exemplary synthetic scheme for synthesizing an intermediate in the synthesis of a methotrexate-containing heterodimeric probe molecule is shown in Scheme 2. Compound 12 may be further modified by covalently attaching a ligand at the free carboxylic acid site.

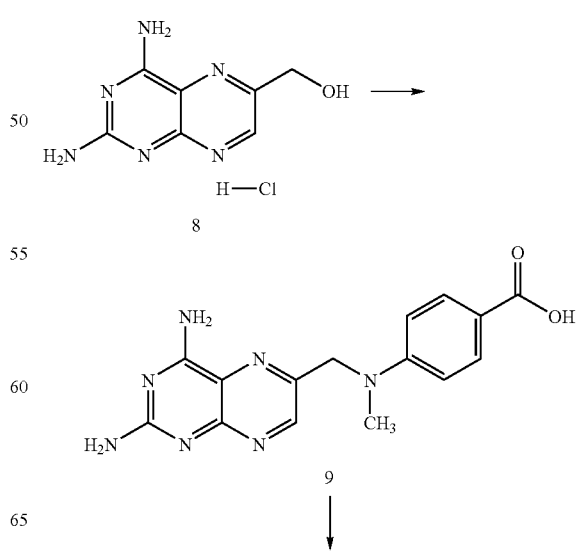

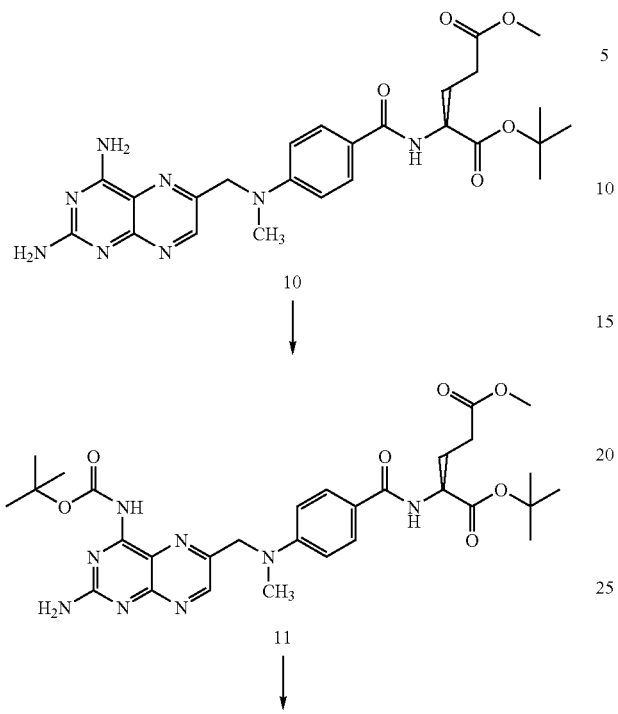
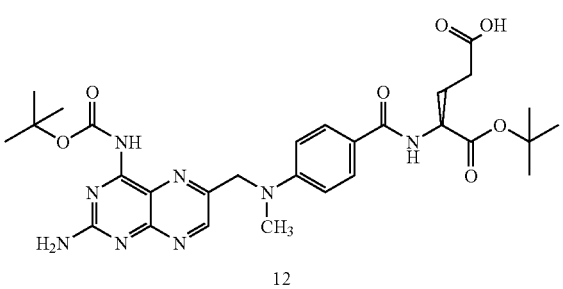
Scheme 3 illustrates an exemplary synthesis of a methotrexate-containing heterodimeric molecule covalently attached to purvalanol B, a potent inhibitor of human CDK2.
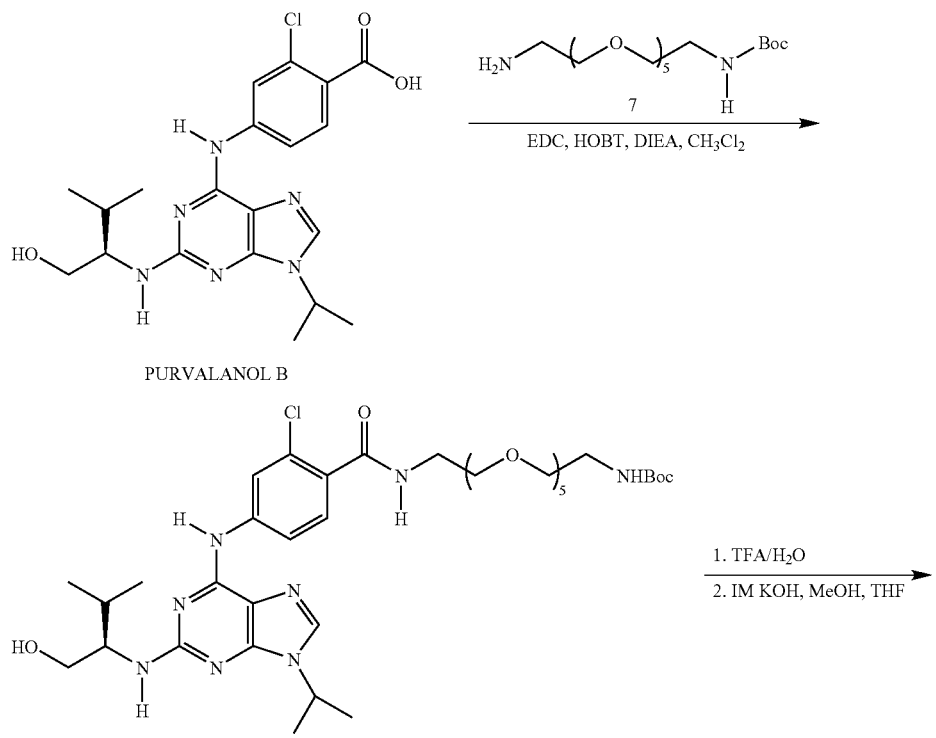

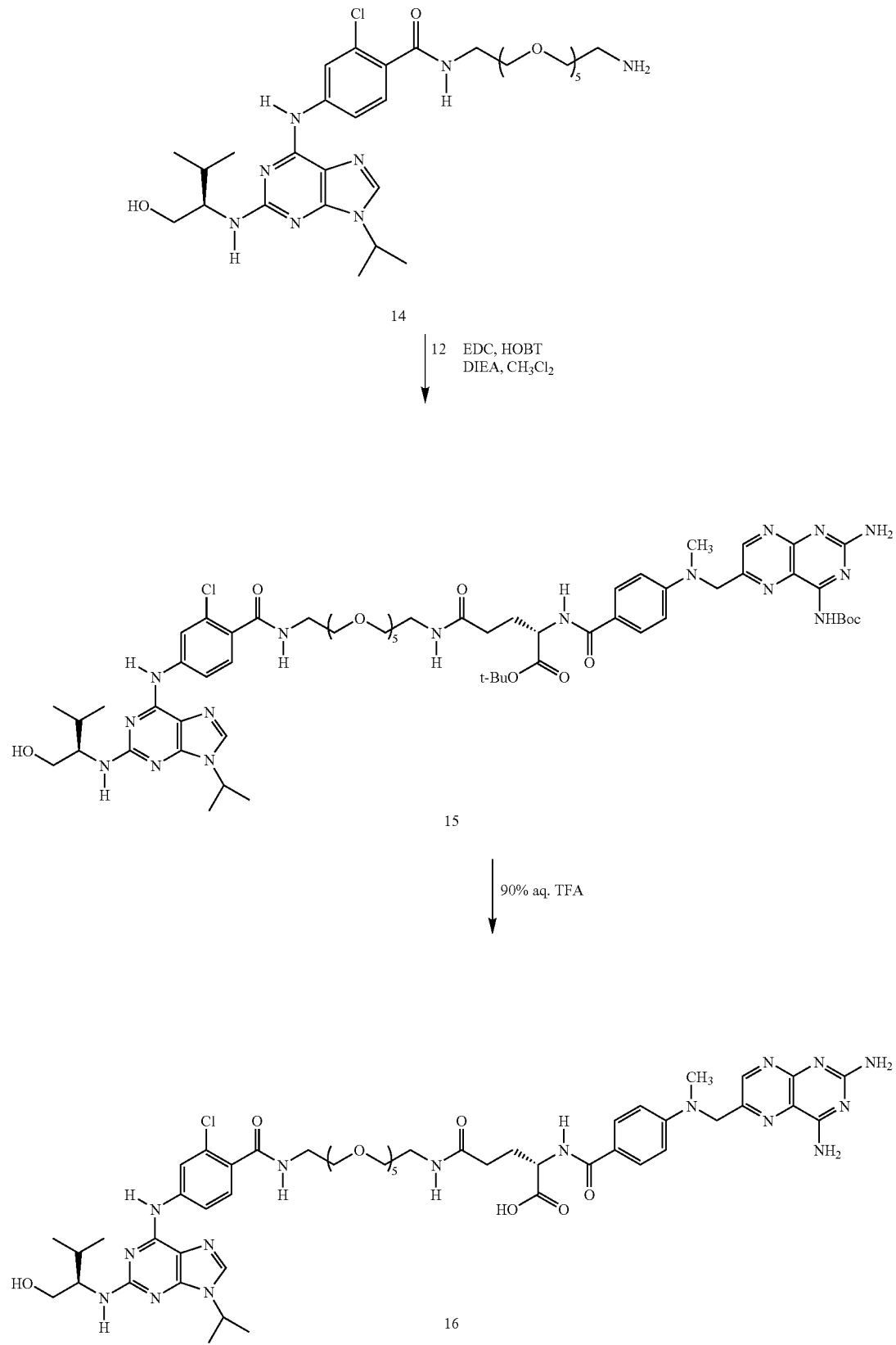

The following illustrates the Scheme 3 synthesis in further detail:

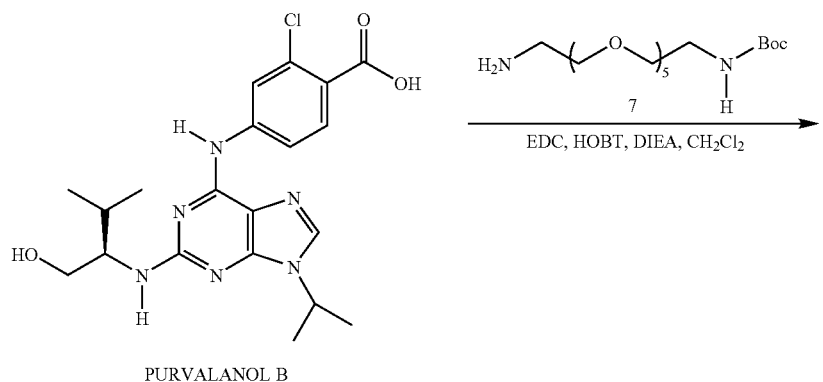

PURVALANOL B

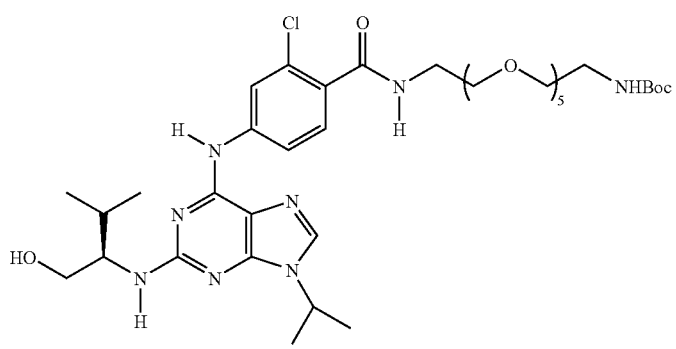

13

To a CH$_2$Cl$_2$ (10 mL) solution of Purvalanol B (100.0 mg, 0.23 mmol) and Boc-5-PEG diamine 7 (114.0 mg, 0.30 mmol) were added diisopropylethylamine (0.10 mL, 0.60 mmol) and HOBT hydrate (46.0 mg, 0.30 mmol) followed by EDC (57.0 mg, 0.30 mmol). The mixture was stirred for 18 hours and then diluted with 100 mL of CH$_2$Cl$_2$ and poured into a separatory funnel. The organic layer was washed with 100 mL portions of 10% citric acid, 1M aqueous NaOH, and brine. The organic layer was separated, dried with anhydrous sodium sulfate, filtered and concentrated under reduced pressure to give 183.0 mg of crude product. The product was of sufficient purity to be used directly in the next reaction 13.

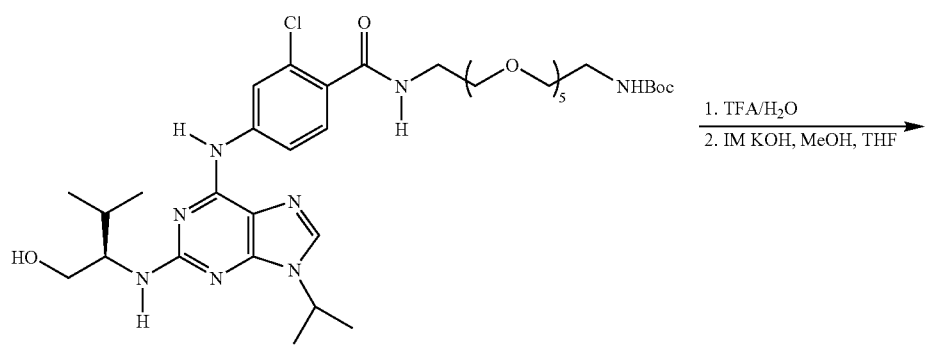

13

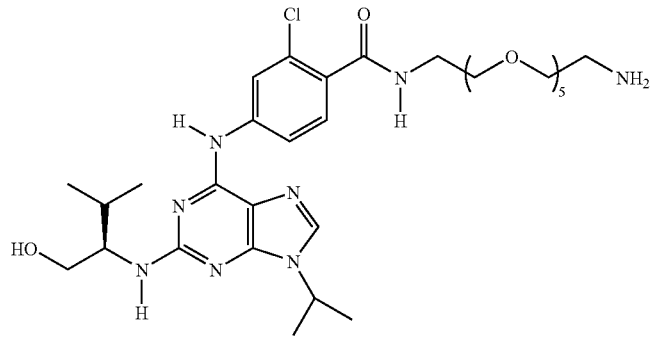

14

The Boc protected amine 13 (183.0 mg, 0.23 mmol) was treated with 90% aqueous trifluoroacetic acid with stirring for two hours. The solvent was then removed under reduced pressure to afford 296.0 mg of crude product. The material was diluted with 100 mL of CH$_2$Cl$_2$ and poured into a separatory funnel. The organic layer was washed with 100 mL portions of saturated aqueous sodium bicarbonate and brine. The organic layer was separated, dried with anhydrous sodium sulfate, filtered and concentrated under reduced pressure to give 147.2 mg of crude product which existed as a mixture of desired product and product that had been trifluoracetylated at the primary amine position. The mixture was dissolved in 6 mL of 1:1 THF/MeOH and then treated with 0.21 mL of 1M aqueous KOH. The reaction was stirred for 24 hours before being diluted with 100 mL of CH$_2$Cl$_2$ and poured into a separatory funnel. The organic layer was washed with 100 mL portions of saturated aqueous sodium bicarbonate and brine. The organic layer was separated, dried with anhydrous sodium sulfate, filtered and concentrated under reduced pressure to give 120.0 mg of crude product which was purified via reverse phase HPLC to yield 65.1 mg of product as the free base 14.

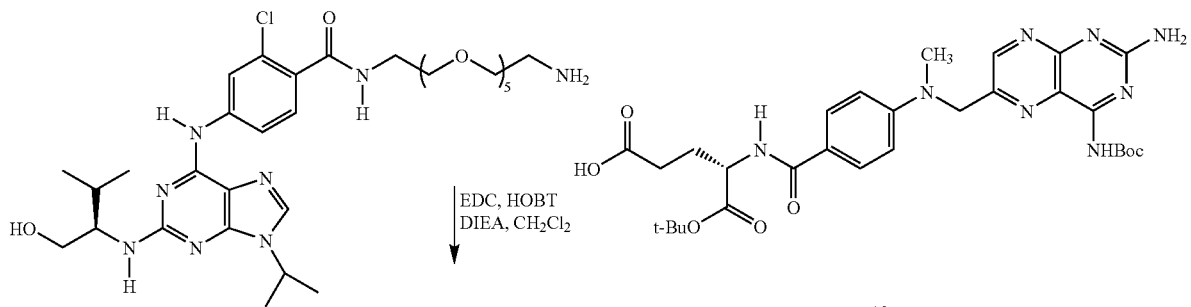

14

12

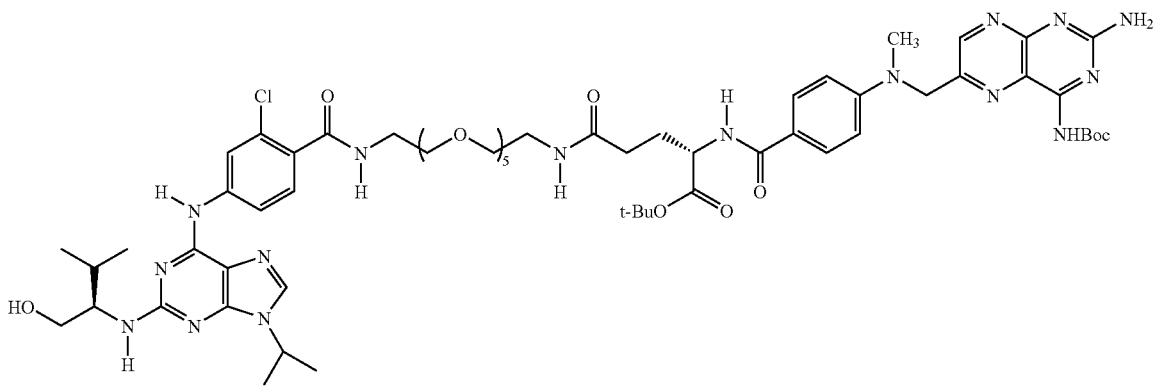

15

To a mixture of the amine 14 (65.1 mg, 0.09 mmol) and the acid 12 (68.5 mg, 0.11 mmol) were added diisopropylethylamine (0.06 mL, 0.32 mmol) and HOBT hydrate (16.8 mg, 0.11 mmol) followed by EDC (21.1 mg, 0.11 mmol). The mixture was stirred for 18 hours and then diluted with 100 mL of $CH_2Cl_2$ and poured into a separatory funnel. The organic layer was washed with 100 mL portions of 10% citric acid, saturated aqueous sodium bicarbonate, and brine. The organic layer was separated, dried with anhydrous sodium sulfate, filtered and concentrated under reduced pressure to give 183.0 mg of crude product 15 which was used without further purification.

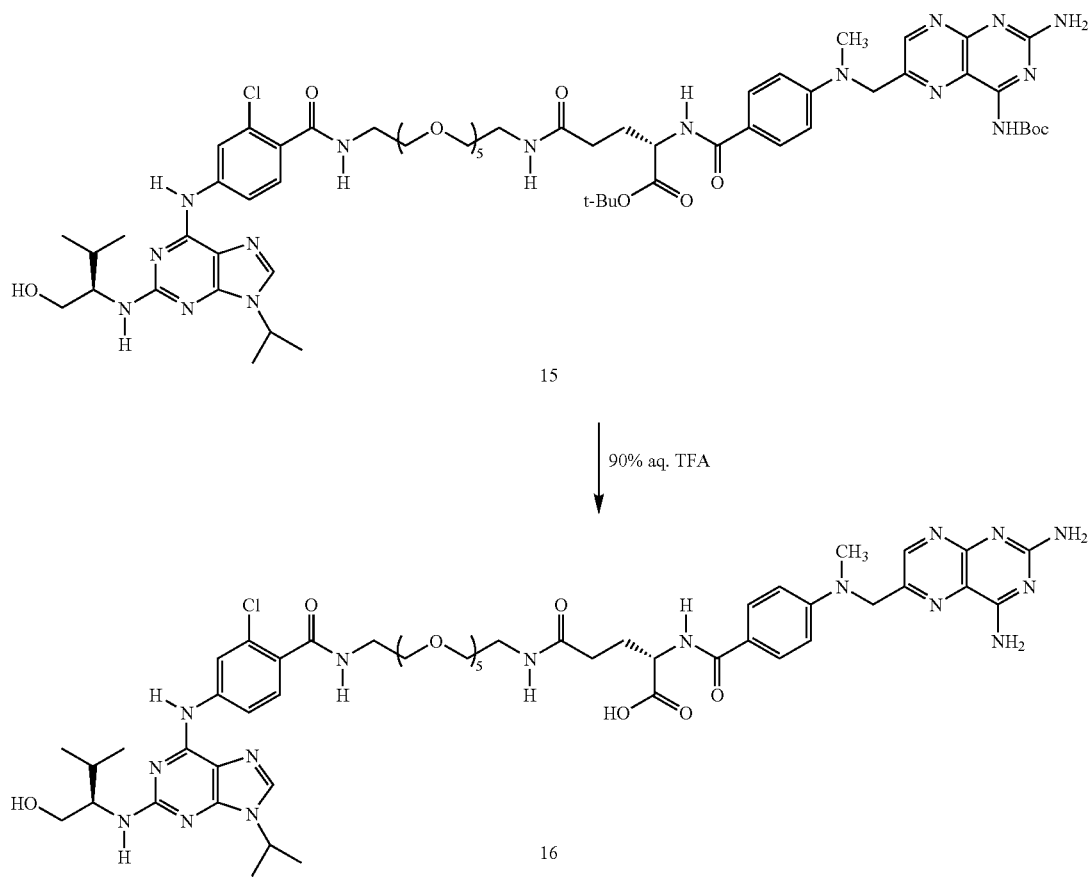

The Boc-t-Bu protected material 15 (141 mg, 0.09 mmol) was treated with 90% aqueous trifluoroacetic acid with stirring for two hours. The solvent was removed under reduced pressure and the residue purified via reverse phase HPLC to give 26.3 mg of product 16 after lyophilization.

d. Pharmaceutical Formulations

Ligands identified as inhibitors, agonists or antagonists in a three-hybrid assay utilizing the heterodimeric probes prepared as described herein can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the ligand that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of ligands. These salts can be prepared in situ during the final isolation and purification of the ligands, or by separately reacting a purified ligand in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", $J.$ $Pharm.$ $Sci.$ 66:1–19)

In other cases, the ligand useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of a ligand(s). These salts can likewise be prepared in situ during the final isolation and purification of the ligand(s), or by separately reacting the purified ligand(s) in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a ligand(s) with the carrier and, optionally, one or more accessory ingredients. In general, the formulations are prepared by uniformly and intimately bringing into association a ligand with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a ligand(s) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ligand(s) may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations for rectal or vaginal administration may be presented as a suppository, which may be prepared by mixing one or more ligand(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a ligand(s) include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to ligand(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a ligand(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The ligand(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a ligand(s) to the body. Such dosage forms can be made by dissolving or dispersing the agent in the proper medium. Absorption enhancers can also be used to increase the flux of the ligand across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more ligand(s) in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of ligand(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the ligand(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "ad ministered systemically," "peripheral administration" and "administered peripherally" as used herein mean the administration of a ligand, drug or other material other than directly into the central nervous system, such that it enters the patient's system and, thus, is subject to metabolism and other like processes, for example, subcutaneous administration.

These ligand(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the ligand(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

E. Examples

The following is a description of the synthesis of the hybrid ligands used herein. However, this description is to be understood as exemplary in nature, and shall in no way limit the scope of the compounds according to the immediate invention. The person skilled in the art will be readily able to envisage other synthetic routes to compounds as provided by the present invention. For example, without limitation, the building blocks $H_2N-CH_2-(CH_2-O-CH_2-O-)_n-CH_2-N_3$ with n=3, 6 and 12 are available from commercial sources (Toronto Research Chemicals Inc., Toronto, Calif.; Fluka, Buchs, Switzerland) and can be employed for the synthesis of compounds of the general structure MTX-L1-L2 with $L1=(-CH_2-O-CH_2)_n-$.

In the compounds used herein, a methotrexate-moiety is linked over 2 or more polyethylenglycol moieties as a linker to dexamethasone, or to compounds known to bind to or inhibit. CDKs. These potential or known CDK inhibitors (CDKi) may be linked to methotrexate via a linker in an orientation that preserves their activity towards inhibition of CDK's ($IC_{50}$ for CDK2 is approx. 180 nM), or in an orientation which abolishes this activity ($IC_{50}>10$ μM). For comparison to previous results using methotrexate linked to other compounds in a three-hybrid assay (Lin et al., J. Am. Chem. Soc. 2000, 122:4247–8), a hybrid ligand of methotrexate-linker-dexamethasone that uses a metadibenzothioester as linker (Mtx-mdbt-Dex) was employed. For the establishment of the effect of varying exclusively the linker, two-hybrid ligands were synthesized wherein methotrexate is linked to a compound with CDK inhibiting activity via a linker containing 3 or 5 polyethylene glycol units.

Except where explicitly stated, all chemical reactants and solvents used are available commercially from vendors the skilled artisan is well familiar with, for example Sigma-Aldrich (St. Louis, Mo., USA) and its subsidiaries.

Example 1

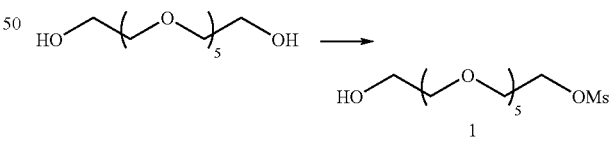

To a dry 500 ml round-bottom flask, equipped with a stir-bar, was added 22.5 g (97.4 mmol) of $Ag_2O$ followed by the addition of 150 ml of $CH_2Cl_2$ and 25.0 g of hexaethylene glycol (88.5 mmol) in 30 ml of $CH_2Cl_2$. The flask was then fitted with a pressure equalizing dropping funnel containing 8.7 ml (106.2 mmol) of methanesulfonyl chloride dissolved in 30 ml of $CH_2Cl_2$. The solution of methanesulfonyl chloride was then added dropwise over 30 minutes and the resulting solution stirred for 3 days. The mixture was then filtered through celite and then concentrated under reduced pressure to give 37.1 g of crude product as an oil. The material was then purified via silica gel column chromatography eluting with 10% methanol in ethyl acetate to give 16.66 g of the hydroxy-monomesylate 1 (52% yield).

Example 2

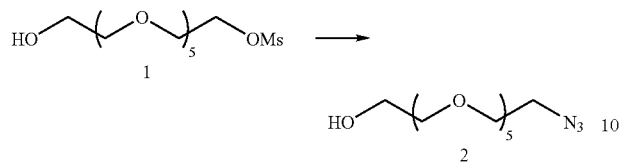

The 5-PEG hydroxy mesylate 1 (16.7 g, 46.2 mm ol) was placed in a 500 ml round-bottom flask, equipped with a stir-bar and jacketed condenser, and dissolved in 120 ml of DMF. Sodium azide (4.5 g, 69.3 mmol) was then added and the mixture heated to 110° C. for 3 hours. The reaction was then allowed to cool to room temperature and 75 ml of toluene was added. The solvent was then removed under reduced pressure and the resulting white solid was dissolved in 300 ml of ethyl acetate. The solid was removed by filtration and the resulting solution concentrated under reduced pressure to give 18.8 g of product 2 (100% yield) which was contaminated by a small amount of DMF (approximately 1:1 DMF to product).

Example 3

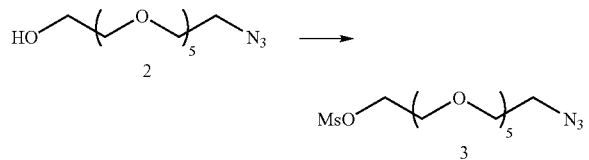

The 5-PEG Hydroxy Azide 2 (19.1 g, 52.1 mmol) and diisopropyl ethyl amine (13.6 ml, 78.2 mmol) were placed in a 1 L round-bottom flask, equipped with a magnetic stir-bar, and dissolved in 250 ml of $CH_2Cl_2$. The flask was then fitted with a pressure-equalizing dropping funnel containing 4.7 ml (57.3 mmol) of methanesulfonyl chloride dissolved in 50 ml of $CH_2Cl_2$. The solution of methanesulfonyl chloride was then added dropwise over 30 minutes and the resulting solution stirred for 2 hours. The resulting solution was then diluted with 300 ml of $CH_2Cl_2$ and washed with 500 ml of 1M HCl, 500 ml of saturated, aqueous sodium bicarbonate, and 500 ml of brine solution. The organic layer was separated, dried with anhydrous sodium sulfate, filtered and concentrated under reduced pressure to give 20.1 g of product 3 (100% yield).

Example 4

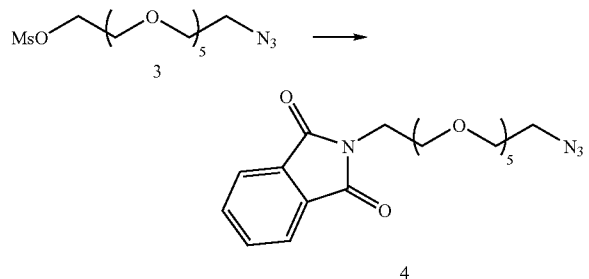

The 5-PEG Azide Mesylate 3 (20.1 g, 52.1 mmol) was dissolved in 200 ml of anhydrous DMSO in a 500 ml round-bottom flask that was equipped with a magnetic stir-bar and jacketed condenser. Then, 14.5 g (78.2 mmol) of potassium phthalimide was added and the solution warmed to 100° C. for 2 hours. The reaction solution was then allowed to cool to room temperature and the mixture diluted with 500 ml of ethyl acetate. The diluted solution was then transferred to a separatory funnel and washed two times with 500 ml of water and once with 500 ml of brine solution. The organic layer was separated, dried with anhydrous sodium sulfate, filtered and concentrated under reduced pressure to give 22.6 g of crude product. The material was then purified via silica gel column chromatography eluting with 50/50 ethyl acetate/hexanes followed by ethyl acetate to give 18.4 g of product 4 (81% yield).

Example 5

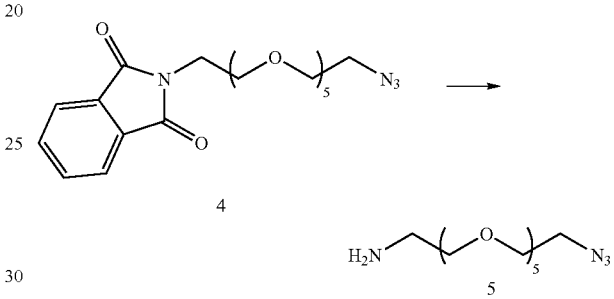

The 5-PEG phthalimide azide 4 (18.4 g, 42.2 mmol) was dissolved in 400 ml of 95% ethanol in a 1 L round-bottom flask that was equipped with a magnetic stir-bar. To the alcohol solution was then added 8.2 ml (168.8 mmol) of hydrazine hydrate and the mixture refluxed for 2 hours. The solution was then cooled to room temperature and filtered in order to remove a white solid. The filtrate was then concentrated under reduced pressure to a white solid which was dissolved in 500 ml of ethyl acetate. The organic layer was then washed five times with 300 ml of water. The aqueous layers were then combined and concentrated to give 12.6 g of product 5 (98% yield).

Example 6

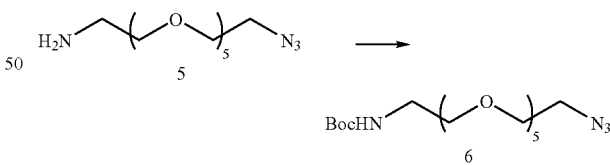

The 5-PEG amino azide 5 (3.53 g, 13.5 mmol) was dissolved in 100 ml of 2M aq. $Na_2CO_3$ in a 1 L round-bottom flask equipped with a magnetic stir-bar and pressure equalizing dropping funnel. Boc-anhydride was dissolved in 100 ml of dioxane in the dropping funnel and added slowly with vigorous stirring. The reaction was stirred for 48 hours before being diluted with 500 ml of ethyl acetate, transferred to a separatory funnel, and washed two times with 500 ml of water. The organic layer was separated, dried with anhydrous sodium sulfate, filtered and concentrated under reduced pressure to give 2.90 g (53% yield) of product 6.

Example 7

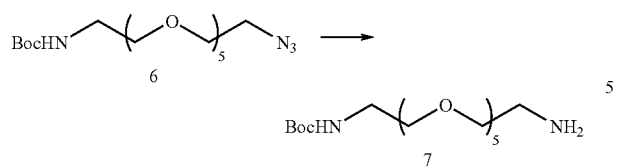

The 5-PEG-Boc-amino azide 6 (2.90 g, 8.0 mmol) was dissolved in 100 ml of ethyl acetate in a Parr bottle and 0.25 g of 10% Pd/C was added. The mixture was stirred under a balloon of hydrogen overnight. The mixture was then diluted with 200 ml of ethyl acetate and filtered through celite. The ethyl acetate was then removed under reduced pressure to give 2.41 g of crude product. The material was then purified via silica gel chromatography eluting with first a mixture of 1% NH$_4$OH/15% MeOH/84% CH$_2$Cl$_2$ followed by a mixture of 1% NH$_4$OH/25% MeOH/74% CH$_2$Cl$_2$ to give 1.37 g of material. The material was dissolved in toluene and then concentrated under reduced pressure to afford 1.21 g (40% yield) of product 7.

Example 8

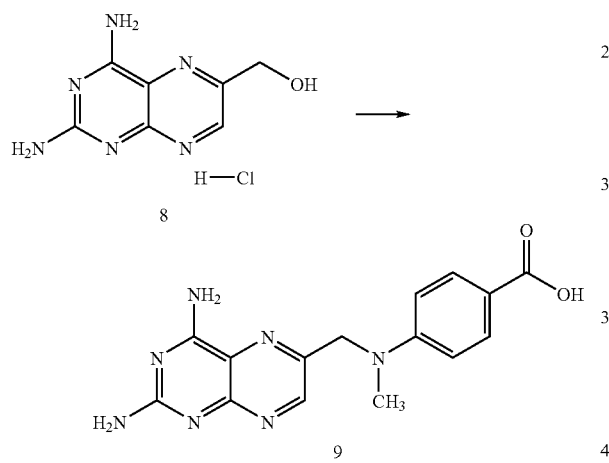

To a solution of pteridine 8 (5 g, 21.9 mmol) in DMA (50 ml) was added Ph$_3$P (17.2 g, 65.6 mmol). The reaction mixture was cooled to 0° C. Br$_2$ (3.4 ml, 65.6 mmol) was added dropwise to the reaction mixture at 0° C. The reaction was warmed to room temperature and stirred for 20 h. DIEA (11 ml), 60 mmol) was added to the reaction mixture followed by 4-methylamino benzoic acid (3.31 g, 21.9 mmol). The reaction mixture was heated to 60–70° C. and stirred for 24 h. The reaction mixture was cooled to room temperature and poured into excess 1 N NaOH solution. The resulting solids were filtered. The filtrate was extracted with Et$_2$O (3×). The aqueous layer was acidified to pH 3–4 with 1N HCl solution. The resulting solid was filtered and dried under vacuum at 50° C. overnight to give the 4.2 g of 9.

Example 9

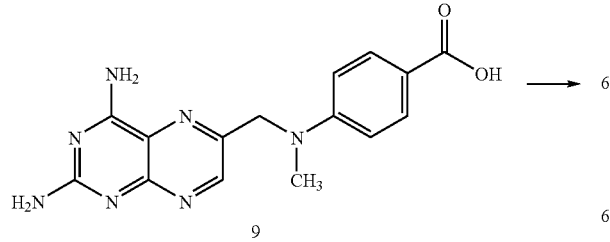

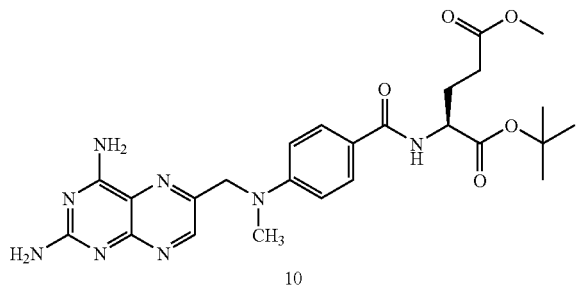

To a solution of 9 (3.3 g, 10.1 mmol) in DMF (340 ml) was added Et$_3$N (2.1 ml, 15.2 mmol) followed by diethylcyanophosphonate. (2.3 ml, 15.2 mmol). The reaction mixture was stirred at room temperature for 3 h. Et$_3$N (2.1 ml, 15.1 mmol) and the glutamic acid diester (2.57 g, 10.1 mmol) were added to the reaction mixture and the reaction was stirred at room temperature for 72 h. The solvents were removed under reduced pressure. The residue was dissolved in CH$_2$Cl$_2$ and the organic layer was washed with 1% NH$_4$OH (2×) and brine (2×). The organic layer was dried (MgSO$_4$) and concentrated. The crude residue was purified by silica gel chromatography (7/7/1 CH$_2$Cl$_2$/acetone/methanol to 7/7/2 CH$_2$Cl$_2$/acetone/methanol) to give 10 (2.6 g).

Example 10

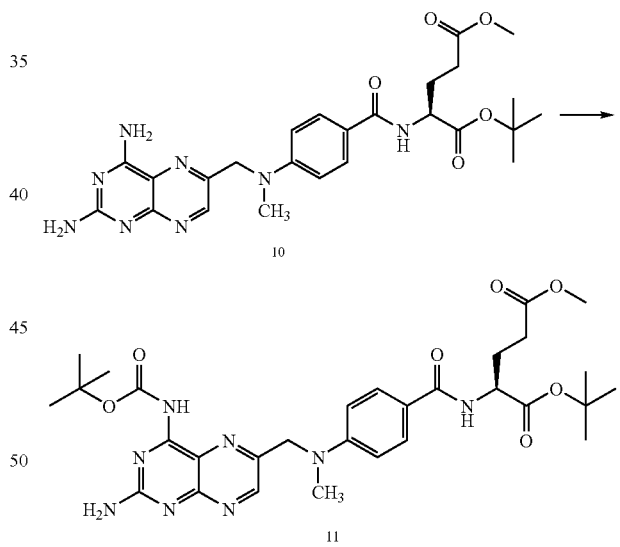

To a suspension of 10 (2.1 g, 4 mmol) in CH$_2$Cl$_2$ was added DIEA (1.1 ml, 6 mmol), DMAP (0.5 g, 4 mmol), followed by Boc$_2$O (0.89 g, 4.1 mmol). The reaction mixture became homogenous upon addition of the Boc$_2$O. The reaction was stirred at room temperature for 1 h, diluted with CH$_2$Cl$_2$ and washed with 1N HCl, sat. NaHCO$_3$ and brine. The organic layer was dried and concentrated. The crude product was purified by silica gel chromatography (7/7/0.5 CH$_2$Cl$_2$/acetone/methanol to 7/7/1 CH$_2$Cl$_2$/acetone/methanol) to give 910 mg of 11, 317 mg of the bis-Boc pteridine and 400 mg of 10.

Example 11
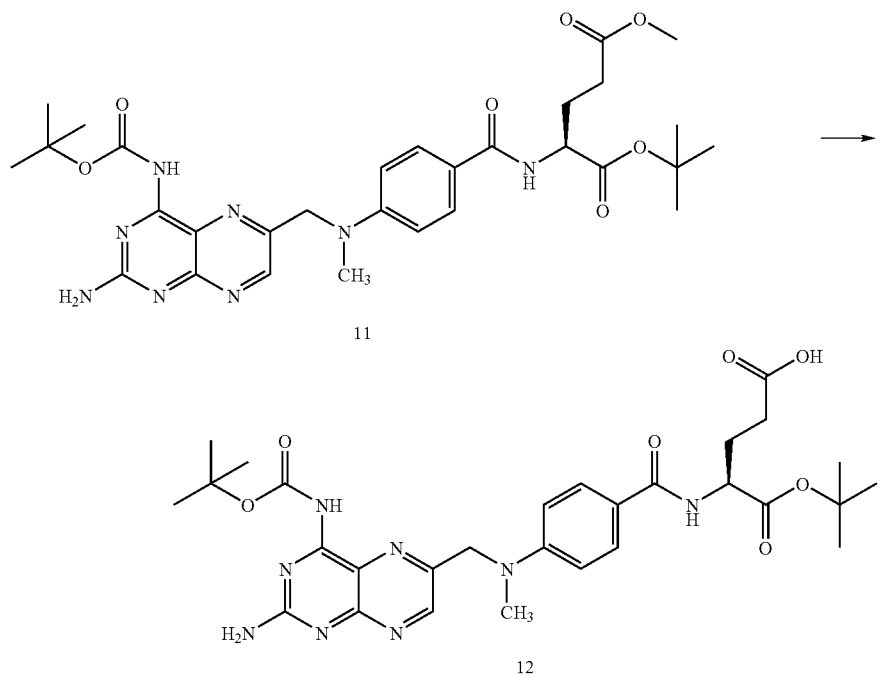
To a solution of 11 (850 mg, 1.36 mmol) in THF-MeOH (30 ml, 1:1), was added 2 M LiOH solution (2.75 ml, 5.5 mmol). The reaction mixture was stirred at room temperature for 3 h, poured into excess 1 N HCl solution and extracted with $CH_2Cl_2$. The organic extracts were dried and concentrated to give 12 (695 mg).
Example 12
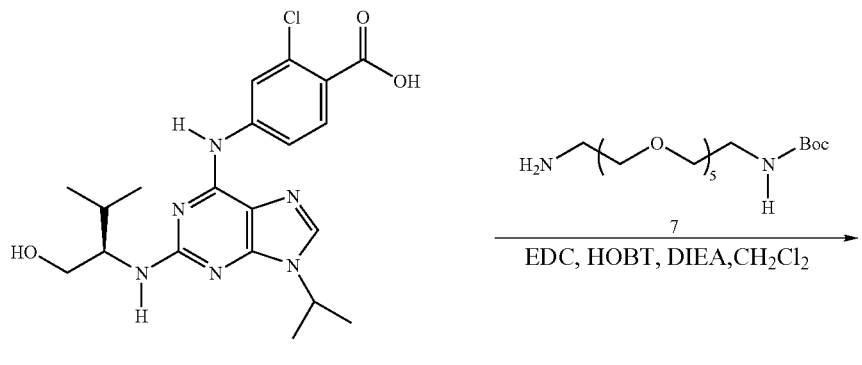
PURVALANOL B
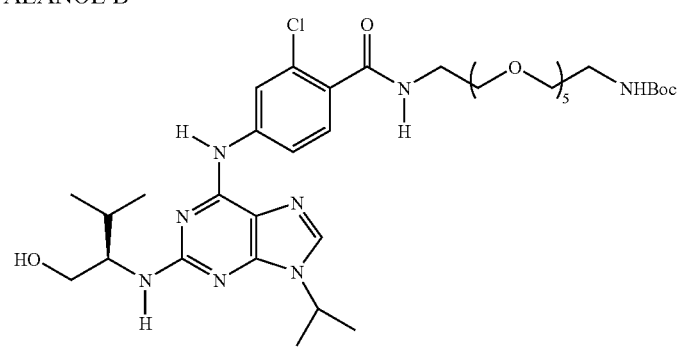
13

To a CH$_2$Cl$_2$ (10 mL) solution of Purvalanol B (100.0 mg, 0.23 mmol) and Boc-5-PEG diamine 7 (114.0 mg, 0.30 mmol) were added diisopropylethylamine (0.10 mL, 0.60 mmol) and HOBT hydrate (46.0 mg, 0.30 mmol) followed by EDC (57.0 mg, 0.30 mmol). The mixture was stirred for 18 hours and then diluted with 100 mL of CH$_2$Cl$_2$ and poured into a separatory funnel. The organic layer was washed with 100 mL portions of 10% citric acid, 1M aqueous NaOH, and brine. The organic layer was separated, dried with anhydrous sodium sulfate, filtered and concentrated under reduced pressure to give 183.0 mg of crude product. The product was of sufficient purity to be used directly in the next reaction 13.

The Boc protected amine 13 (183.0 mg, 0.23 mmol) was treated with 90% aqueous trifluroacetic acid with stirring for two hours. The solvent was then removed under reduced pressure to afford 296.0 mg of crude product. The material was diluted with 100 mL of CH$_2$Cl$_2$ and poured into a separatory funnel. The organic layer was washed with 100 mL portions of saturated aqueous sodium bicarbonate and brine. The organic layer was separated, dried with anhydrous sodium sulfate, filtered and concentrated under reduced pressure to give 147.2 mg of crude product which existed as a mixture of desired product and product that had been trifluoracetylated at the primary amine position. The mixture was dissolved in 6 mL of 1:1 THF/MeOH and then treated with 0.21 mL of 1M aqueous KOH. The reaction was stirred for 24 hours before being diluted with 100 mL of CH$_2$Cl$_2$ and poured into a separatory funnel. The organic layer was washed with 100 mL portions of saturated aqueous sodium bicarbonate and brine. The organic layer was separated, dried with anhydrous sodium sulfate, filtered and concentrated under reduced pressure to give 120.0 mg of crude product which was purified via reverse phase HPLC to yield 65.1 mg of product as the free base 14.

Example 13

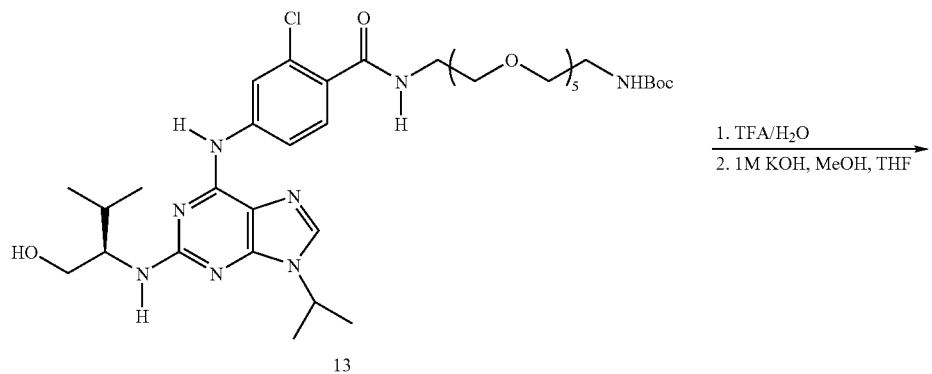

1. TFA/H$_2$O
2. 1M KOH, MeOH, THF

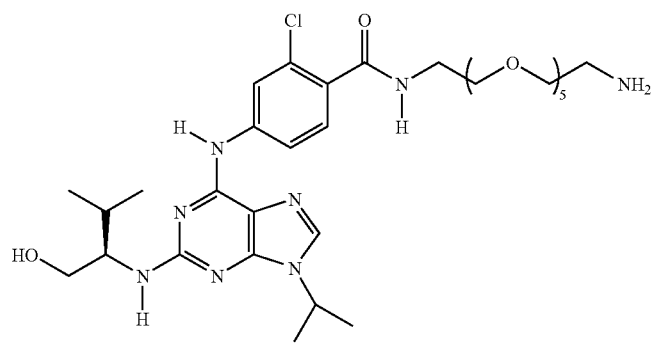

Example 14

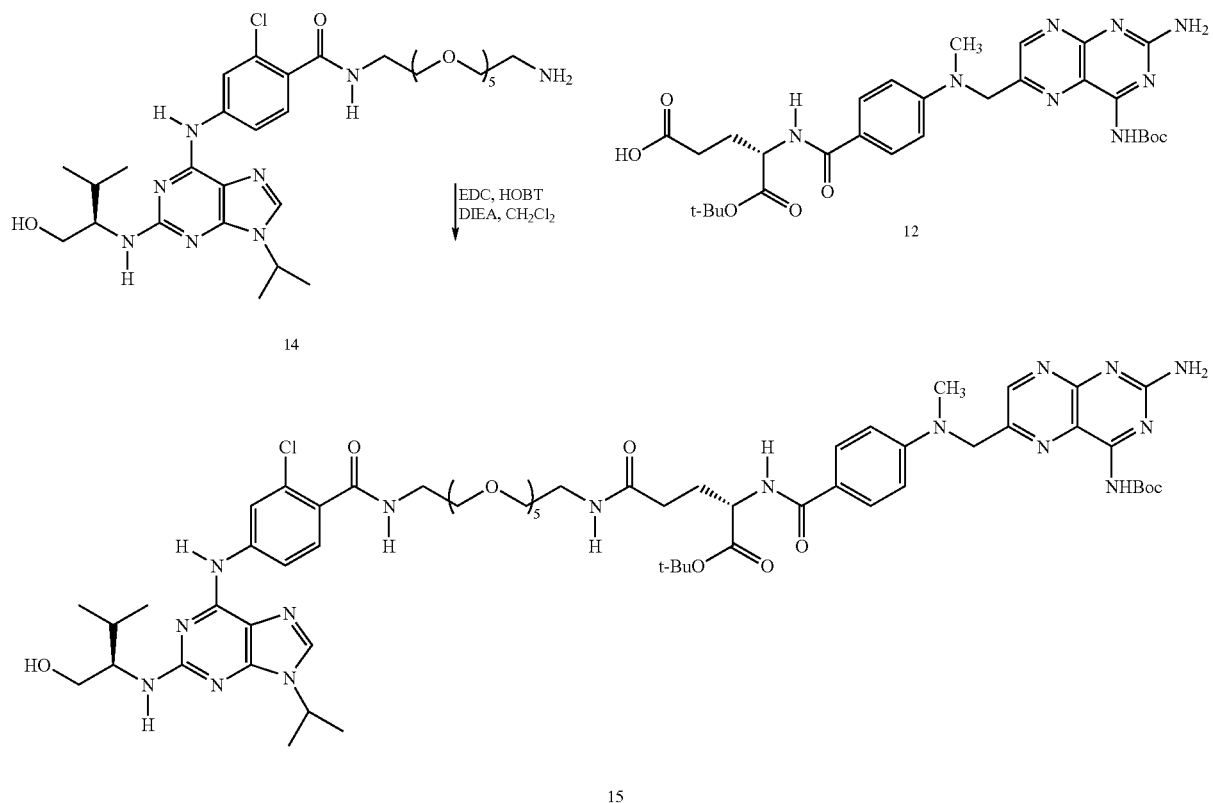

To a mixture of the amine 14 (65.1 mg, 0.09 mmol) and the acid 12 (68.5 mg, 0.1 mmol) were added diisopropylethylamine (0.06 mL, 0.32 mmol) and HOBT hydrate (16.8 mg, 0.11 mmol) followed by EDC (21.1 mg, 0.11 mmol). The mixture was stirred for 18 hours and then diluted with 100 mL of $CH_2Cl_2$ and poured into a separatory funnel. The organic layer was washed with 100 mL portions of 10% citric acid, saturated aqueous sodium bicarbonate, and brine. The organic layer was separated, dried with anhydrous sodium sulfate, filtered and concentrated under reduced pressure to give 183.0 mg of crude product 15 which was used without further purification.

Example 15

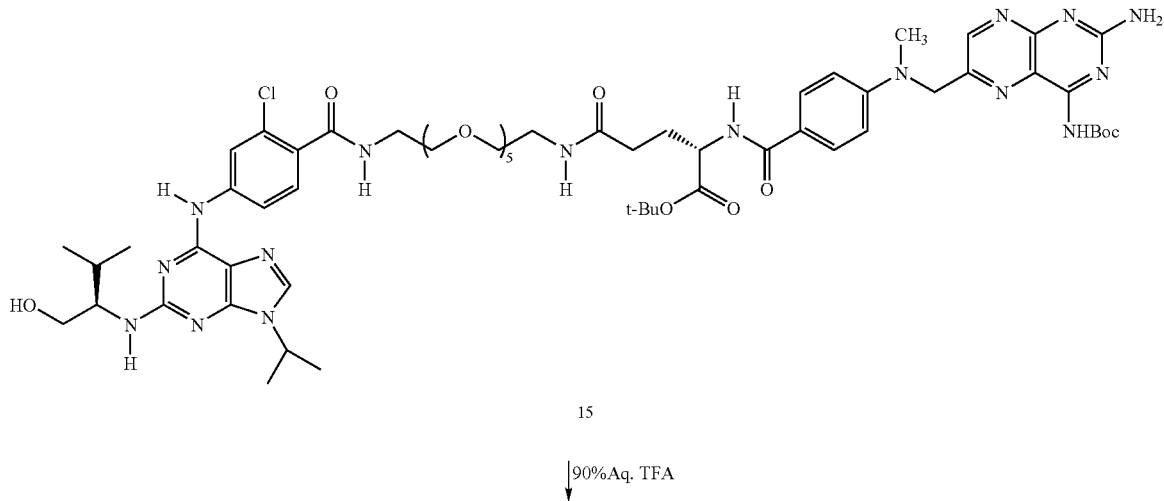

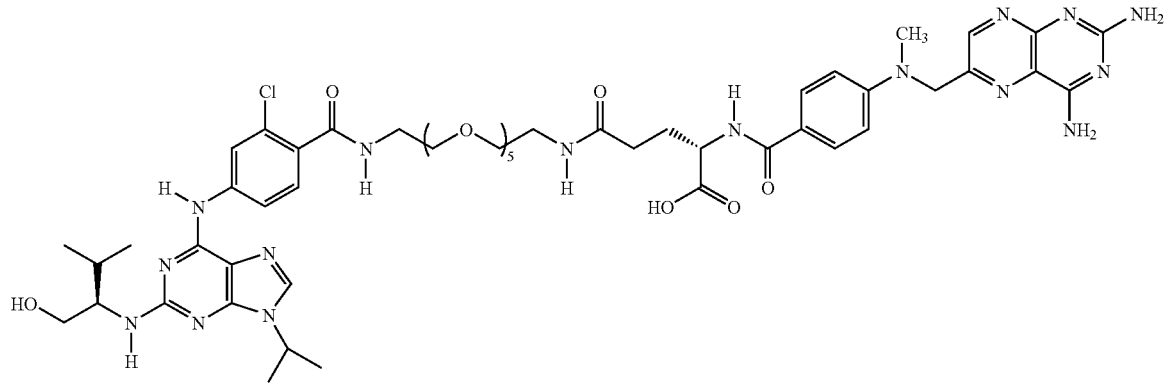

16

The Boc-t-Bu protected material 15 (141 mg, 0.09 mmol) was treated with 90% aqueous trifluoroacetic acid with stirring for two hours. The solvent was removed under reduced pressure and the residue purified via reverse phase HPLC to give 26.3 mg of product 16 after lyophilization.

D. References

1. Licitra, E. J. et al., Proc. Natl. Acad. Sci. USA, (1996), 93: 12817–12821
2. Vidal M. et al., Nuc. Ac. Res., (1999), 27(4): 919–929
3. Topcu Z. et al., Pharm. Res., (2000), 17(9): 1049–1055
4. Fields & Song Nature, (1989), 340: 245–6
5. Gyuris et al. Cell, (1993) 75: 791–803
6. Yang et al., Nuc. Ac. Res., (1995), 23, 1152–1156
7. Fields, et al., U.S. Pat. No. 5,468,614; Crabtree et al., U.S. Pat. No. 5,830,462, U.S. Pat. No. 5,869,337, U.S. Pat. No. 6,165,787; Fowlkes et al. WO 94/23025; Broach et al. WO 95/30012; Holt et al. WO 96/06097.

All of the references and publications cited herein are hereby incorporated by reference.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

TABLE 2

| Compound | Structure |
|---|---|
| 1 | 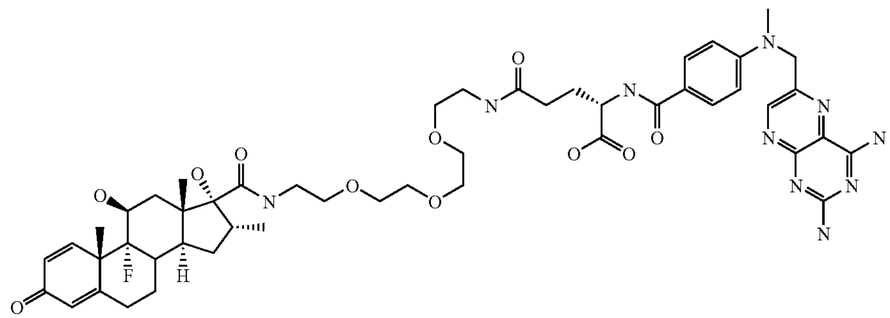 |
| 2 | 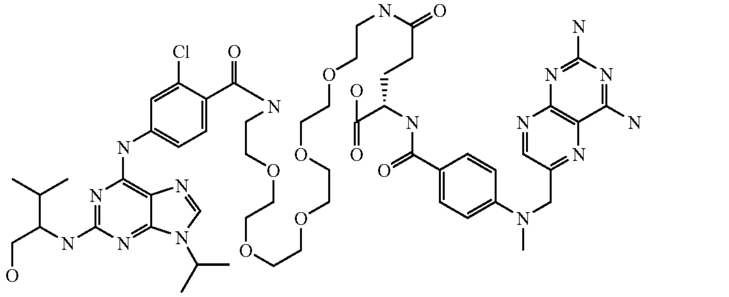 |

TABLE 2-continued

| Compound | Structure |
|---|---|
| 3 | 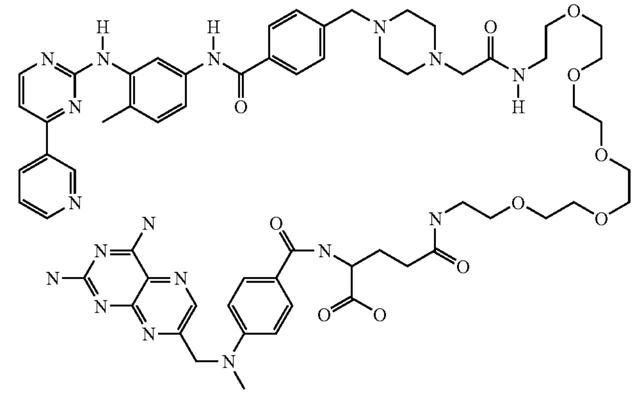 |
| 4 | 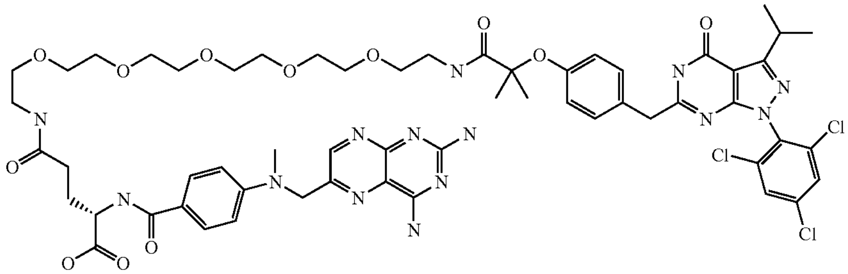 |
| 5 | 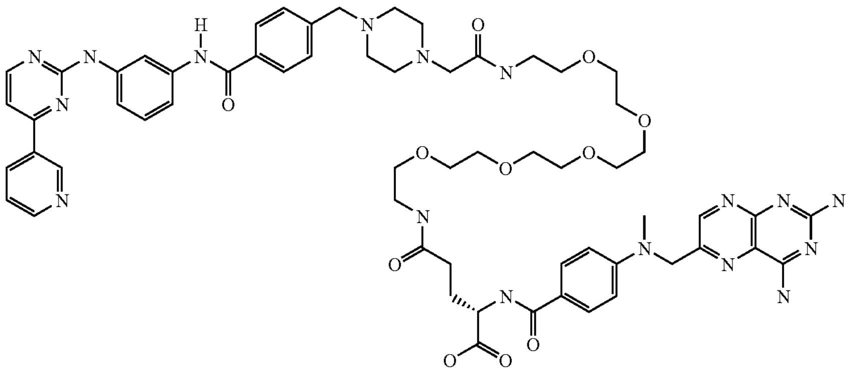 |
| 6 | 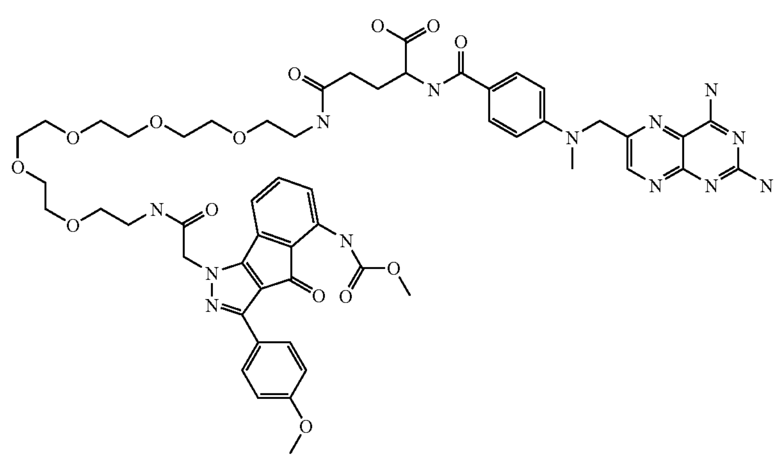 |

TABLE 2-continued
| Compound | Structure |
|---|---|
| 7 | 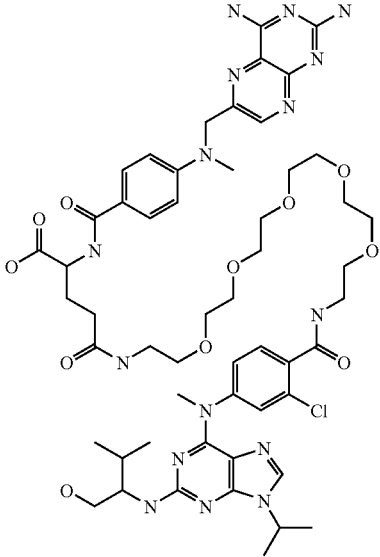 |
| 8 | 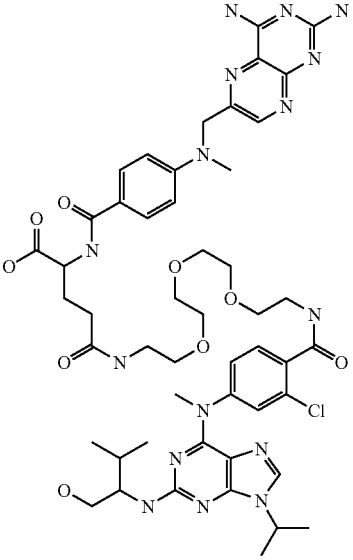 |
| 9 | 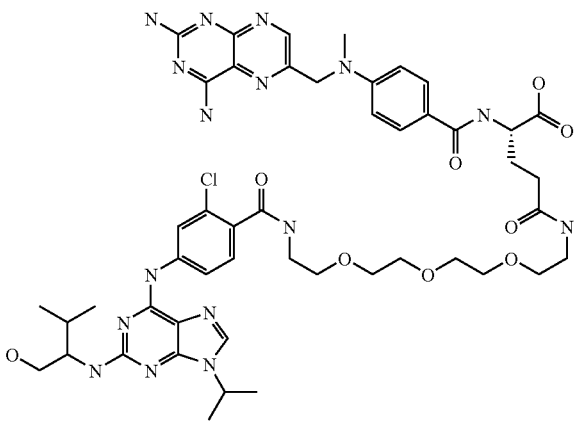 |

TABLE 2-continued
| Compound | Structure |
|---|---|
| 10 | 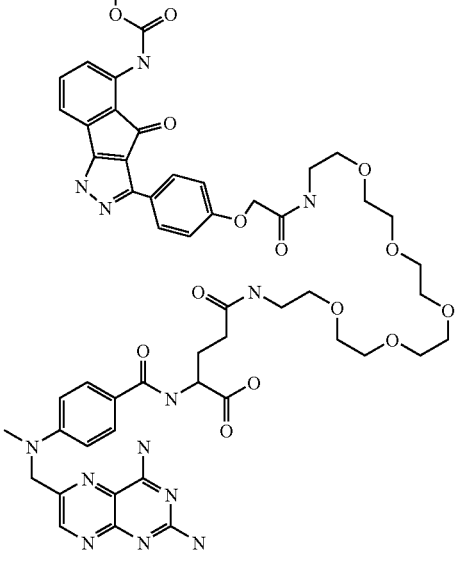 |
| 11 | 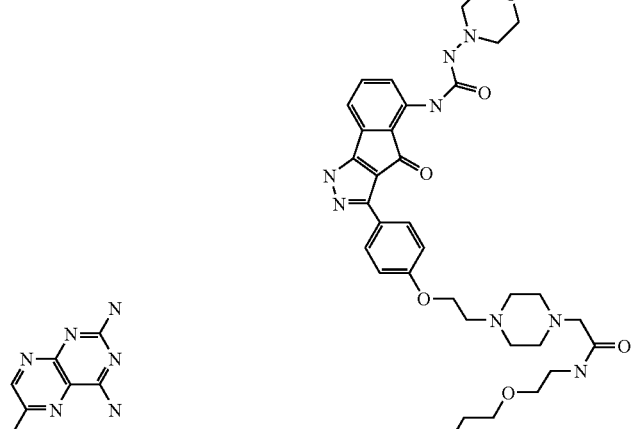 |

TABLE 2-continued

| Compound | Structure |
|---|---|
| 12 | 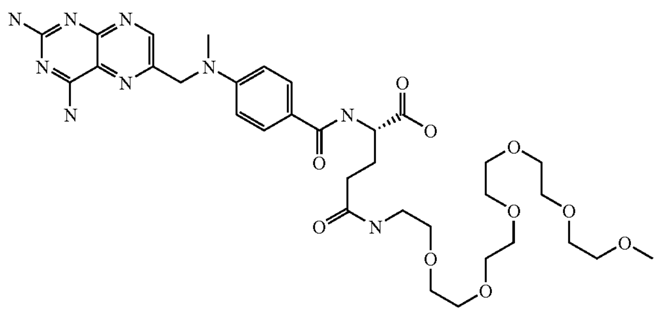 |
| 13 | 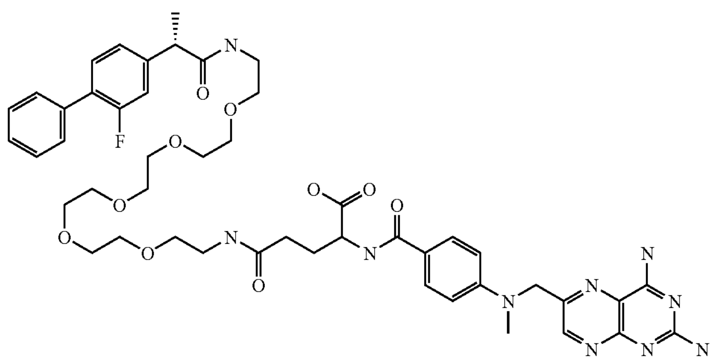 |
| 14 | 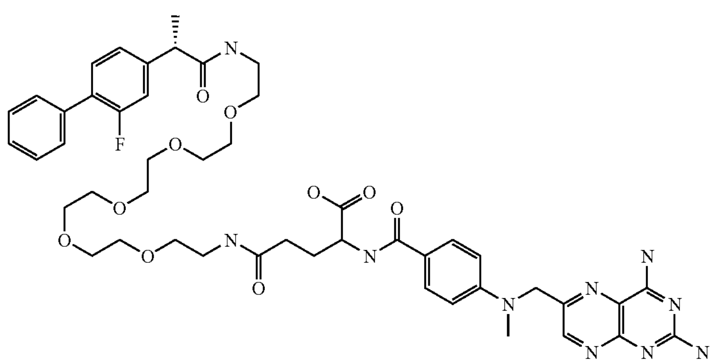 |
| 15 | 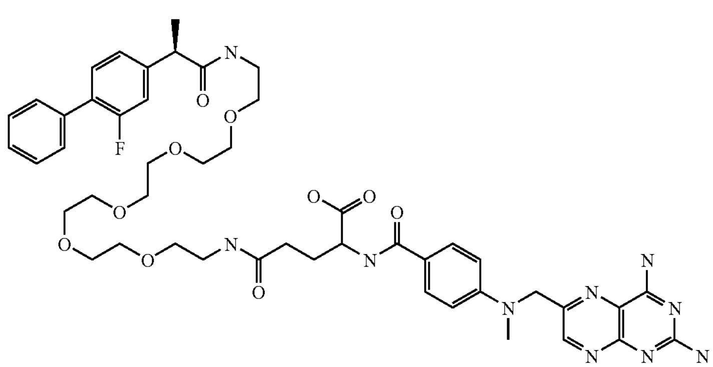 |

TABLE 2-continued
| Compound | Structure |
|---|---|
| 16 | 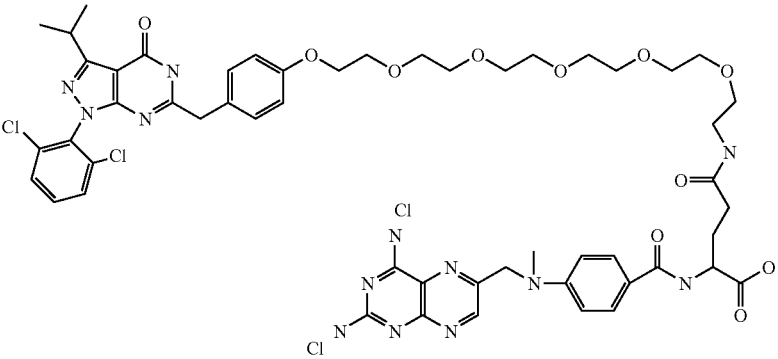 |
| 17 | 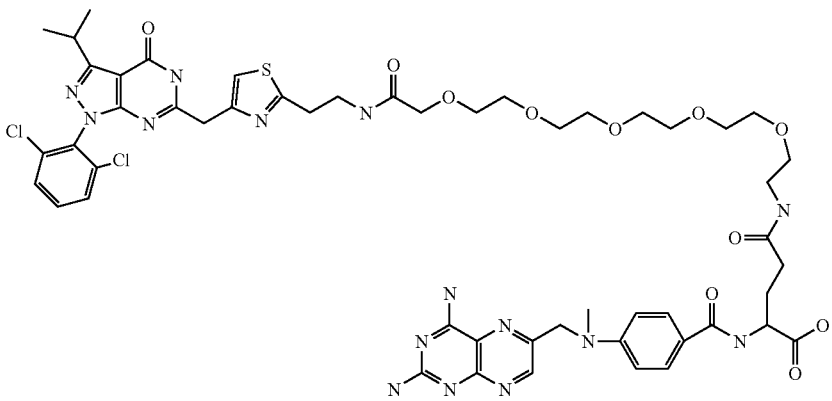 |
| 18 | 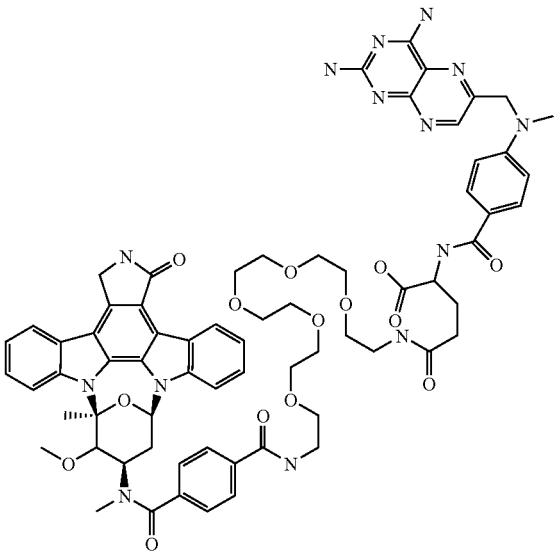 |

TABLE 2-continued

| Compound | Structure |
|---|---|
| 19 | 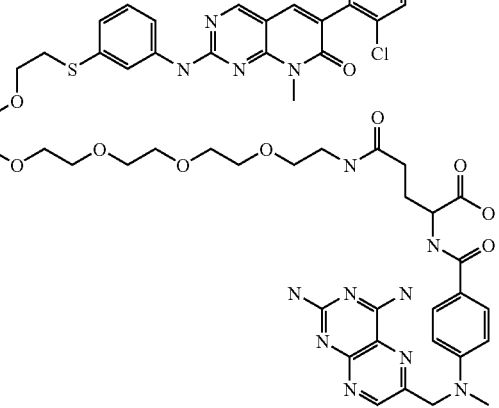 |
| 20 | 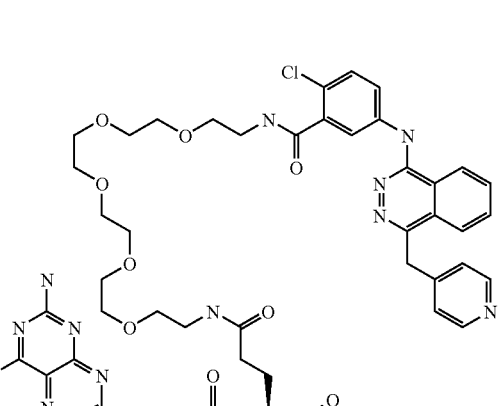 |

We claim:

1. A method of synthesizing the structure shown represented by Formula II:

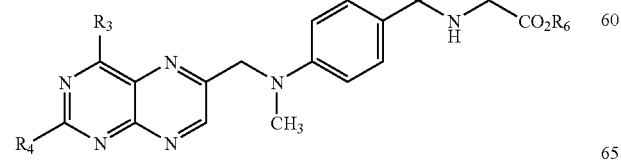

(II)

wherein $R_3$ represents NHZ;

$R_4$ represents $NH_2$;

Z represents t-Boc; and $R_6$ represents an alkyl, aryl, trialkylsilylalkyl, or an acid-labile carboxy-protecting group; comprising a. reacting the structure represented by IIa with $Boc_2O$, an alkyl amine base, and a nucleophilic catalyst in a suitable organic solvent

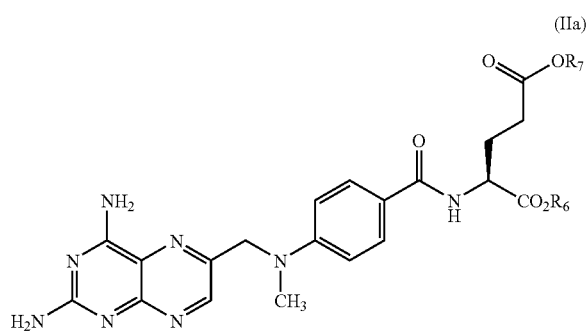

wherein $R_7$ represents an alkyl, aryl, trialkylsilylalkyl, or an acid-labile carboxy protecting group; and b. removing $R_7$ to yield the structure represented by Formula II.

2. The method of claim 1, wherein the organic solvent is dichloromethane.

3. The method of claim 1, wherein
$R_6$ represents $CH_3$, $^tBu$, Bn, or $CH_2$—$CH_2$—$SiMe_3$; and
$R_7$ represents hydrogen, $CH_3$, $^tBu$, Bn, or $CH_2$—$CH_2$—$SiMe_3$.

4. The method of claim 3, wherein $R_6$ represents $^tBu$, and $R_7$ represents a $CH_3$.

5. A compound having a structure of Formula II:

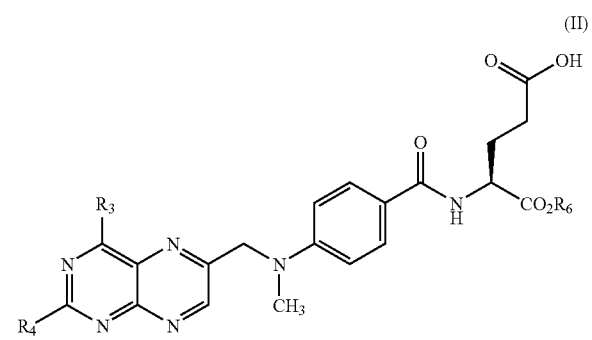

wherein $R_3$ represents NHZ;

$R_4$ represents $NH_2$;

Z represents t-Boc; and $R_6$ represents an alkyl, aryl, trialkylsilylalkyl or an acid-labile carboxy-protecting group.

* * * * *